United States Patent
McKinlay

(10) Patent No.: US 11,446,394 B2
(45) Date of Patent: *Sep. 20, 2022

(54) LIPID NANOPARTICLE FORMULATIONS COMPRISING LIPIDATED CATIONIC PEPTIDE COMPOUNDS FOR NUCLEIC ACID DELIVERY

(71) Applicant: NUTCRACKER THERAPEUTICS, INC., Emeryville, CA (US)

(72) Inventor: Colin James McKinlay, Emeryville, CA (US)

(73) Assignee: NUTCRACKER THERAPEUTICS, INC., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/347,539

(22) Filed: Jun. 14, 2021

(65) Prior Publication Data

US 2021/0369867 A1 Dec. 2, 2021

Related U.S. Application Data

(63) Continuation of application No. 17/279,460, filed as application No. PCT/US2019/053661 on Sep. 27, 2019.

(60) Provisional application No. 62/885,036, filed on Aug. 9, 2019, provisional application No. 62/738,717, filed on Sep. 28, 2018.

(51) Int. Cl.
| | |
|---|---|
| *A61K 48/00* | (2006.01) |
| *C07K 7/08* | (2006.01) |
| *C07K 7/06* | (2006.01) |
| *A61K 9/51* | (2006.01) |
| *A61K 47/54* | (2017.01) |
| *A61K 31/7105* | (2006.01) |
| *A61K 47/10* | (2017.01) |
| *C07K 2/00* | (2006.01) |

(52) U.S. Cl.
CPC ........ *A61K 48/0041* (2013.01); *A61K 9/5123* (2013.01); *A61K 9/5146* (2013.01); *A61K 31/7105* (2013.01); *A61K 47/10* (2013.01); *A61K 47/543* (2017.08); *C07K 2/00* (2013.01); *C07K 7/06* (2013.01); *C07K 7/08* (2013.01)

(58) Field of Classification Search
None
See application file for complete search history.

(56) References Cited

U.S. PATENT DOCUMENTS

| | | |
|---|---|---|
| 6,191,115 B1 | 2/2001 | Haviv et al. |
| 6,534,484 B1 | 3/2003 | Wheeler et al. |
| 6,586,410 B1 | 7/2003 | Wheeler et al. |
| 6,858,225 B2 | 2/2005 | Semple et al. |
| 7,341,738 B2 | 3/2008 | Semple et al. |
| 7,901,708 B2 | 3/2011 | MacLachlan et al. |
| 8,058,069 B2 | 11/2011 | Yaworski et al. |
| 8,492,359 B2 | 7/2013 | Yaworski et al. |
| 8,772,255 B2* | 7/2014 | Burkoth ............ A61K 47/44 514/44 A |
| 9,035,039 B2 | 5/2015 | Dhillon et al. |
| 9,062,021 B2 | 6/2015 | Budzik et al. |
| 9,364,435 B2 | 6/2016 | Yaworski et al. |
| 9,404,127 B2 | 8/2016 | Yaworski et al. |
| 9,446,132 B2 | 9/2016 | Stanton et al. |
| 9,504,651 B2 | 11/2016 | MacLachlan et al. |
| 9,518,272 B2 | 12/2016 | Yaworski et al. |
| 9,579,338 B2 | 2/2017 | Knopov et al. |
| 9,687,448 B2 | 6/2017 | Akinc et al. |
| 9,758,795 B2 | 9/2017 | Cullis et al. |
| 9,872,900 B2 | 1/2018 | Ciaramella et al. |
| 9,878,042 B2 | 1/2018 | Yaworski et al. |
| 10,143,758 B2 | 12/2018 | Guild et al. |
| 10,300,018 B2 | 5/2019 | Adami et al. |
| 10,358,647 B2 | 7/2019 | Minomi et al. |
| 10,799,602 B2 | 10/2020 | Baumhof |
| 10,808,252 B2 | 10/2020 | Lizasoain Hernandez et al. |
| 10,821,186 B2 | 11/2020 | Manoharan et al. |
| 10,822,368 B2 | 11/2020 | DeRosa et al. |
| 10,829,760 B2 | 11/2020 | Lee |
| 10,844,377 B2 | 11/2020 | Khvorova et al. |
| 10,864,162 B2 | 12/2020 | Kim et al. |

(Continued)

FOREIGN PATENT DOCUMENTS

| | | | |
|---|---|---|---|
| EP | 3318248 B1 | 4/2019 | |
| EP | 2833869 B1 | 10/2020 | |

(Continued)

OTHER PUBLICATIONS

Murphy et al., A combinatorial approach to the discovery of efficient cationicpeptoid reagents for gene delivery (PNAS, 1998, 95: 1517-1522) (Year: 1998).*

(Continued)

*Primary Examiner* — Arthur S Leonard
(74) *Attorney, Agent, or Firm* — Marshall, Gerstein & Borun LLP

(57) ABSTRACT

The present disclosure relates to lipid mixtures comprising lipidated cationic peptide compounds, such as tertiary amino lipidated and/or PEGylated cationic peptide compounds or lipitoids, for nucleic acid delivery. More specifically, the present disclosure relates to lipid nanoparticle formulations comprising lipidated cationic peptide compounds and other lipid components including structural lipid, phospholipid and shielding lipids. The present disclosure also relates to methods of preparing and using the lipid mixtures.

26 Claims, 11 Drawing Sheets

(56) References Cited

U.S. PATENT DOCUMENTS

| | | |
|---|---|---|
| 10,888,626 B2 | 1/2021 | Guild et al. |
| 10,933,127 B2 | 3/2021 | Ciaramella et al. |
| 10,940,207 B2 | 3/2021 | DeRosa et al. |
| 10,941,395 B2 | 3/2021 | Yin et al. |
| 2003/0203865 A1 | 10/2003 | Harvie et al. |
| 2011/0053829 A1 | 3/2011 | Baumhof et al. |
| 2011/0230397 A1 | 9/2011 | Carriero et al. |
| 2014/0142044 A1 | 5/2014 | Burke, Jr. et al. |
| 2019/0032087 A1 | 1/2019 | Cullis et al. |
| 2019/0192690 A1 | 6/2019 | Guild et al. |
| 2019/0216730 A1 | 7/2019 | Heartlein et al. |
| 2020/0069594 A1 | 3/2020 | Sood et al. |
| 2021/0009629 A1 | 1/2021 | DeRosa et al. |

FOREIGN PATENT DOCUMENTS

| | | |
|---|---|---|
| EP | 2871178 B1 | 12/2020 |
| EP | 2155351 B1 | 2/2021 |
| EP | 2858679 B1 | 2/2021 |
| EP | 3569711 B1 | 2/2021 |
| WO | WO-2005060697 A2 | 7/2005 |
| WO | 2012000104 A1 | 1/2012 |
| WO | WO-2018064755 A1 | 4/2018 |
| WO | 2018107061 A1 | 6/2018 |

OTHER PUBLICATIONS

Kowalski, et al. "Delivering the Messenger: Advances in Technologies for Therapeutic mRNA Delivery", Molecular Therapy, ePub Feb. 2019, 27(4), pp. 710-728.

Lobo et al., Structure/Function Analysis of Peptoid/Lipitoid:DNA Complexes, Journal of Pharmaceutical Sciences, 2003, 92(9), 1905-1918.

Simon et al., Peptoids: A modular approach to drug discovery, Proc. Natl. Acad. Sci. USA, 1992, 89, 9367-9371.

Utku et al., A Peptidomimetic SiRNA Transfection Reagent for Highly Effective Gene Silencing, Molecular BioSystems, 2006, 2(6-7), 312-317.

* cited by examiner

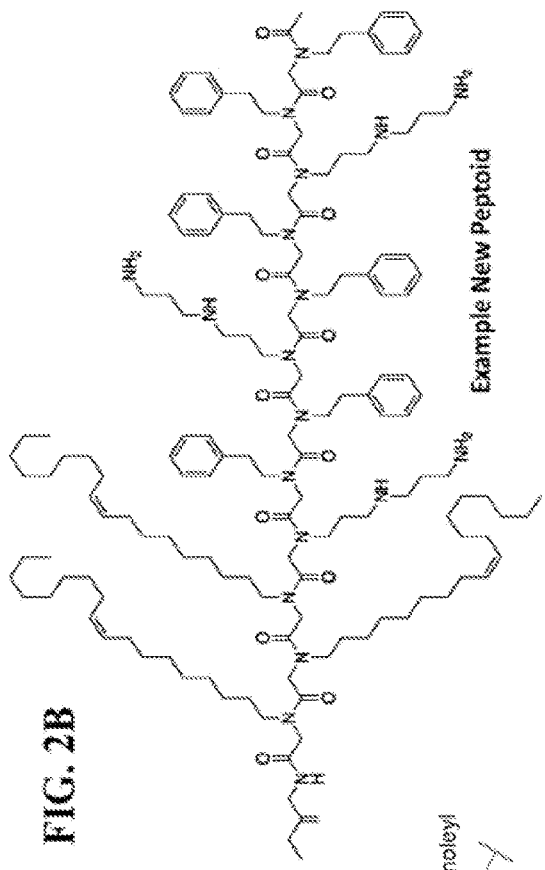
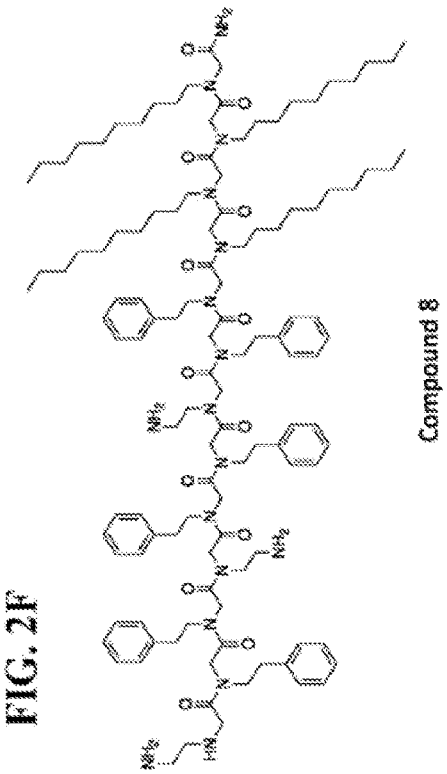
FIG. 2A  FIG. 2B  FIG. 2F
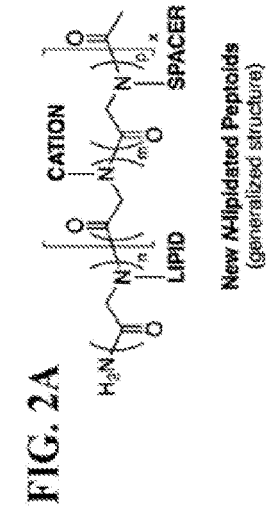
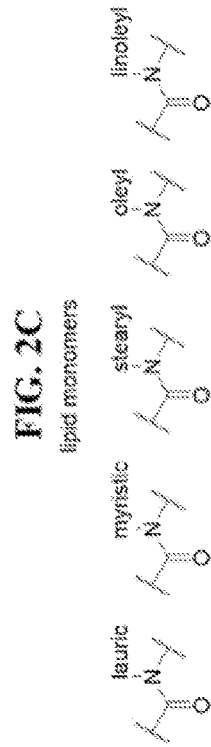
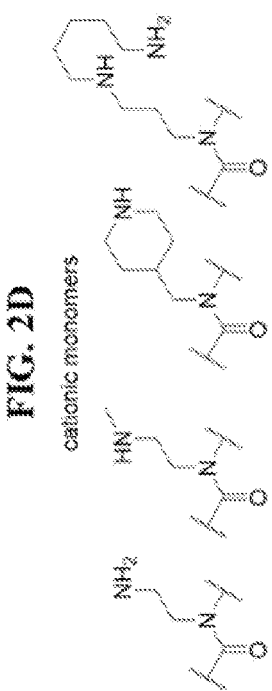
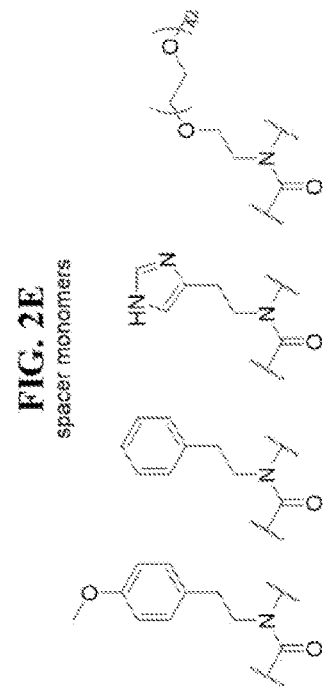
FIG. 2C FIG. 2D FIG. 2E

| Total Lipid:mRNA mass ratio | Mass % Lipitoid (cholesterol:DOPE = 0.5:1) | | | | | | Mass % Lipitoid (cholesterol:DOPE = 1:1) | | | | | |
|---|---|---|---|---|---|---|---|---|---|---|---|---|
| | 20% | 40% | 50% | 60% | 70% | 80% | 20% | 40% | 50% | 60% | 70% | 80% |
| 8:1 | 337 | 3378 | 6172 | 4394 | 3671 | 3610 | 219 | 1704 | 4348 | 2973 | 4167 | 2290 |
| 7:1 | 101 | 7187 | 10183 | 10010 | 10336 | 8285 | 117 | 6142 | 8148 | 10035 | 8205 | 7991 |
| 6:1 | 66 | 5945 | 10907 | 10271 | 10814 | 8440 | 117 | 7702 | 9563 | 9941 | 8052 | 6314 |
| 5:1 | 21 | 2021 | 4521 | 6644 | 7482 | 4330 | 81 | 2399 | 4468 | 6494 | 5706 | 3235 |

| Total Lipid:mRNA mass ratio | Mass % Lipitoid (cholesterol:DOPE = 1.5:1) | | | | | | Mass % Lipitoid (cholesterol:DOPE = 2:1) | | | | | |
|---|---|---|---|---|---|---|---|---|---|---|---|---|
| | 20% | 40% | 50% | 60% | 70% | 80% | 20% | 40% | 50% | 60% | 70% | 80% |
| 8:1 | 57 | 2400 | 4463 | 5641 | 6472 | 5273 | 69 | 838 | 2136 | 4672 | 4225 | 3168 |
| 7:1 | 103 | 2634 | 3911 | 4819 | 4973 | 4851 | 100 | 440 | 1760 | 2015 | 2541 | 821 |
| 6:1 | 36 | 1182 | 3736 | 5446 | 5771 | 3753 | 50 | 547 | 784 | 1611 | 1524 | 429 |
| 5:1 | 40 | 1285 | 1325 | 3637 | 4551 | 2334 | 30 | 433 | 985 | 2261 | 2709 | 1665 |

| cholesterol: DOPE ratio | |
|---|---|
| 0.5:1 | 1:1 |
| 1.5:1 | 2:1 |

FIG. 8A

LIPID NANOPARTICLE FORMULATIONS COMPRISING LIPIDATED CATIONIC PEPTIDE COMPOUNDS FOR NUCLEIC ACID DELIVERY

CROSS-REFERENCE TO RELATED APPLICATIONS

This application is a continuation of U.S. patent application Ser. No. 17/279,460 filed on Mar. 24, 2021, which is a national stage application under 35 U.S.C. § 371 of International Application No. PCT/US2019/053661, filed internationally on Sep. 27, 2019, which claims priority to and the benefit of U.S. Provisional Patent Application No. 62/738,717, filed on Sep. 28, 2018, and U.S. Provisional Patent Application No. 62/885,036, filed on Aug. 9, 2019, the disclosures of each of which are incorporated herein by reference in their entireties.

FIELD

The present disclosure relates generally to multicomponent lipid compositions comprising complexes of lipidated cationic peptide compounds and other lipid components with polyanionic compounds. More specifically, the present disclosure relates to multicomponent lipid formulations, wherein the lipidated cationic peptide compounds comprise tertiary amino lipidated and/or PEGylated cationic peptide compounds and/or lipitoids. The present disclosure also relates to methods of preparing the multicomponent lipid compositions described herein and methods of using the lipid compositions for the delivery of nucleic acids to cells.

BACKGROUND

Gene therapy remains a promising technology that is expected to revolutionize the field of medicine. In current practice, however, the ability to deliver nucleic acid material to a patient's cells in a reproducible and efficient manner has been a major hurdle to the viability and, thus also, the widespread adoption of gene therapeutics. This critical requirement has been achieved with varying success by a number of different approaches, including for example, the use of viral vectors, or via non-viral methods utilizing single (standalone) compound delivery vehicles or multicomponent liposomal formulations for charge complexation with the nucleic acid material. Although viral vectors typically demonstrate more efficient and selective delivery of nucleic acid material to cells than non-viral compositions, non-viral approaches are preferred for easier large-scale production and reduced host immunogenicity.

Consequently, efforts to develop non-viral delivery vehicles and formulations with improved delivery efficiency are ongoing. However, despite the positive outlook for both of the non-viral approaches detailed above, there still remains much room for improvement in terms of enabling broader flexibility of non-viral compositions for the desired application or, at the very least, greater simplicity in optimization of existing delivery vehicles.

As the insertion of genetic material into cells for practicable therapeutic applications will strongly depend upon the type of nucleic acid to be delivered for each situation, there still remains a need for new delivery vehicles and/or formulations which have the flexibility support the delivery of various types of nucleic acid material to a range of different targets and which can be more readily optimized for any given genetic cargo and/or cellular target.

BRIEF SUMMARY

The present disclosure provides multicomponent lipid compositions comprising lipidated cationic peptide compounds for the delivery of nucleic acids with improved efficiency.

In one aspect, the present disclosure provides a composition, comprising complexes of:

one or more polyanionic compounds; and
lipid components, wherein the lipid components comprise:
(i) optionally one or more structural lipids;
(ii) one or more phospholipids;
(iii) one or more shielding lipids; and
(iv) one or more lipidated cationic peptide compounds, wherein the one or more lipidated cationic peptide compounds are selected from the group consisting of:
(a) one or more tertiary amino lipidated and/or PEGylated cationic peptide compounds of formula (1) or salts thereof:

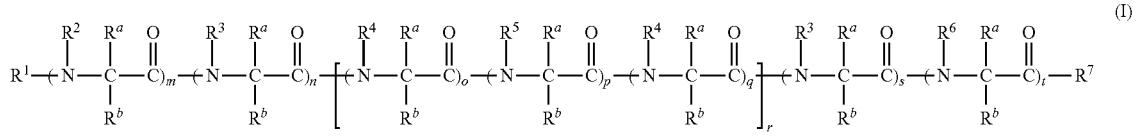

(I)

wherein:
m is an integer from 0 to 10;
n is an integer from 0 to 5;
s is an integer from 0 to 5;
t is an integer from 0 to 10;
wherein at least one of m, n, s, and t is nonzero;
r is an integer from 1 to 20;
each o is independently an integer 0, 1, or 2;
each q is independently an integer 0, 1, or 2;
each p is independently an integer 1 or 2;
$R^1$ is —H, alkyl, alkylaryl, —$COR^{1a}$ or a lipid moiety, wherein $R^{1a}$ is —H, —OH, alkyl, aryl, alkylaryl, —O-alkyl, or —O-alkylaryl;
each $R^2$ is independently an ethylene glycol moiety of the formula
—$CH_2CH_2O(CH_2CH_2O)_uCH_3$, and wherein each u is independently an integer from 2 to 200;
each $R^3$ is independently a lipid moiety;
each $R^4$ is independently a neutral spacer moiety or a lipid moiety;
each $R^5$ is independently a cationic moiety;
each $R^6$ is independently an ethylene glycol moiety of the formula
—$CH_2CH_2O(CH_2CH_2O)_vCH_3$, and wherein each v is independently an integer from 2 to 200;

$R^7$ is —H, alkyl, acyl, —OH, —OR$^{7a}$, —NH$_2$, —NHR$^{7a}$, or a lipid moiety, wherein R$^{7a}$ is alkyl, acyl, or a lipid moiety; and each R$^a$ and R$^b$ are independently —H, $C_1$-$C_4$-alkyl, or a side chain moiety found on a naturally- or non-naturally-occurring amino acid;

(b) one or more lipitoids of formula (II):

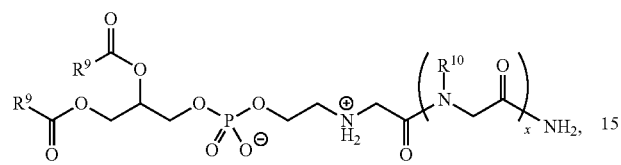

wherein:
x is a integer from 1 to 100;
each R$^9$ is independently a lipid moiety; and
each R$^{10}$ is independently a cationic or neutral spacer moiety;
and
(c) any combination thereof.

In some embodiments of this aspect, the composition comprises 40-80% w/w one or more lipidated cationic peptide compounds of the total weight of the lipid components. In certain embodiments, the composition comprises 40-70% w/w one or more lipidated cationic peptide compounds of the total weight of the lipid components.

In certain embodiments, which may be combined with one or more of the preceding embodiments, the one or more lipidated cationic peptide compounds are one or more tertiary amino lipidated and/or PEGylated cationic peptide compounds of the formula (I) or salts thereof. In certain embodiments, which may be combined with one or more of the preceding embodiments, at least one of n or s is nonzero. In still other embodiments, which may be combined with any of the previous embodiments, the one or more tertiary amino lipidated and/or PEGylated cationic peptide compound comprises a block of N-lipidated amino acid residues, wherein at least one of n and s is at least 2, at least 3, or at least 4, optionally, 2, 3, or 4. In other embodiments of the foregoing embodiments, which may be combined with any of the other foregoing embodiments, each R$^3$ is independently $C_4$-$C_{22}$-alkyl or $C_4$-$C_{22}$-alkenyl, and wherein the $C_4$-$C_{22}$-alkenyl is optionally mono- or poly-unsaturated. In other embodiments, each R$^3$ is independently $C_8$-$C_{12}$ alkyl. In still yet other embodiments, each R$^3$ is independently selected from the group consisting of 2-ethylhex-1-yl, caproyl, oleyl, stearyl, linoleyl, myristyl, and lauryl.

In some embodiments of the present aspect, at least one of the one or more tertiary amino lipidated and/or PEGylated cationic peptide compounds comprises a cationic domain comprising at least two cationic amino acid residues having cationic moieties R$^5$. In other embodiments, which may be combined with one or more of any of the previous embodiments, each R$^5$ is independently aminoalkyl, alkylaminoalkyl, aminoalkylaminoakyl, guanidinoalkyl, N-heterocyclylalkyl or N-heteroaryl. In certain embodiments, which may be combined with any of the foregoing embodiments, each R$^5$ is independently selected from the group consisting of:

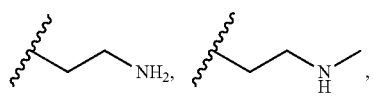

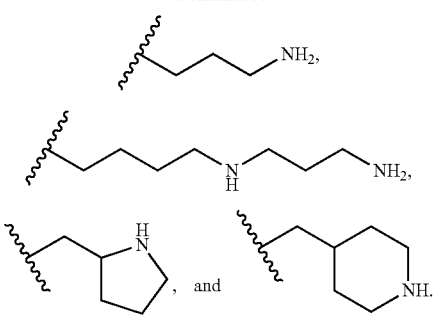

In still other embodiments, each R$^5$ is

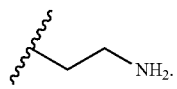

In yet other embodiments of the present aspect, each neutral spacer moiety R$^4$ is independently a $C_1$-$C_4$-alkyl substituted by cycloalkyl, heterocyclylalkyl, alkylaryl, arylalkyl, alkylheteroaryl, heteroarylalkyl, alkoxy, alkoxyalkyl, or hydroxyalkyl, wherein each cycloalkyl, heterocyclylalkyl, alkylaryl, arylalkyl, alkylheteroaryl, heteroarylalkyl, alkoxy, alkoxyalkyl, or hydroxyalkyl is optionally substituted with one or more substituents —OH, halo, or alkoxy. In some embodiments, which may be combined with one or more of any of the preceding embodiments, each neutral spacer moiety R$^4$ is independently selected from the group consisting of:

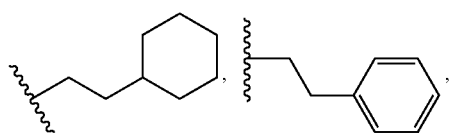

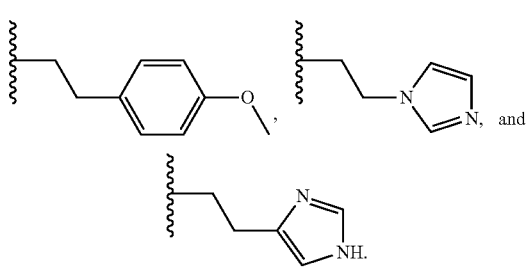

In certain embodiments, each neutral spacer moiety R$^4$ is

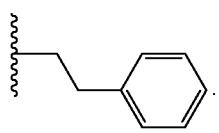 [SMILES: *CCc1ccccc1]

In yet further embodiments, which may be combined with one or more of any of the previous embodiments, at least one of the one or more tertiary amino lipidated and/or PEGylated cationic peptide compounds comprises a cationic domain comprising at least two amino acid residues having $R^5$ cationic moieties and wherein each of the at least two cationic amino acid residues within the cationic domain are separated by at least one amino acid residue having a neutral spacer or lipid moiety $R^4$. In some embodiments of the present aspect, which may be combined with one or more of any of the foregoing embodiments, at least one of the one or more tertiary amino lipidated and/or PEGylated cationic peptide compounds comprises at least one trimer subunit —$R^{cation}$—$R^{neutral}$—$R^{neutral}$, and wherein $R^{cation}$ is an amino acid residue comprising a cationic moiety $R^5$ and each $R^{neutral}$ is an amino acid residue comprising a neutral spacer moiety $R^4$. In certain embodiments of any of the foregoing embodiments, each cationic moiety $R^5$ is

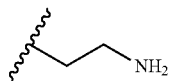

and each neutral spacer moiety $R^4$ is

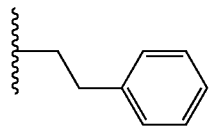

In some embodiments of this aspect, which may be combined with any one or more of the previous embodiments, when m is an integer from 0 to 3, each u is independently an integer from 20 to 200, optionally from 30 to 50; and when m is an integer from 4 to 10, each u is independently an integer from 2 to 10. In other embodiments of this aspect, which may be combined with any one or more of the previous embodiments, when t is an integer from 0 to 3, each v is independently an integer from 30 to 50; when t is an integer from 4 to 10, each v is independently an integer from 2 to 10. In still yet further embodiments of this aspect, m is 1, and u is an integer from 40 to 45; or t is 1, and v is an integer from 40 to 45.

In other embodiments of this aspect, which may be combined with any one or more of the previous embodiments, $R^a$ and $R^b$ are independently selected from the group consisting of —H and —$CH_3$. In certain other embodiments of this aspect, which may be combined with any one or more of the previous embodiments, $R^a$ and $R^b$ are —H.

In other embodiments of the present aspect, the one or more lipidated cationic peptide compounds are one or more lipitoids of formula (II). In certain embodiments, the one or more lipitoids of formula (II) are Lipitoid 1.

In still other embodiments of this aspect, which may be combined with any one or more of the previous embodiments, the composition comprises 0-40% w/w one or more structural lipids of the total weight of the lipid components. In yet other embodiments, the composition comprises 0-25% w/w one or more structural lipids of the total weight of the lipid components. In still further embodiments, the one or more structural lipid are selected from the group consisting of cholesterol, fecosterol, sitosterol, ergosterol, campesterol, stigmasterol, brassicasterol, tomatidine, ursolic acid, alpha-tocopherol, and mixtures thereof. In certain embodiments, the one or more structural lipids is cholesterol.

In some embodiments of the present aspect, which may be combined with any one or more of the preceding embodiments, the composition comprises 10-60% w/w one or more phospholipids of the total weight of the lipid components. In other embodiments, the composition comprises 20-40% w/w one or more phospholipids of the total weight of the lipid components. In some embodiments, which may be combined with any of the preceding embodiments, the one or more phospholipids are selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C 16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and any mixtures thereof. In certain embodiments, the one or more phospholipids is 1,2-dioleoyl-sn-glycero-3-phosphoethanolamine (DOPE).

In still further embodiments, which may be combined with any one or more of the preceding embodiments, the composition comprises 1-5% w/w one or more shielding lipids of the total weight of the lipid components. In some embodiments of the preceding embodiment, the one or more shielding lipids are one or more PEG lipids selected from the group consisting of a PEG-modified phosphatidylethanolamine, a PEG-modified phosphatidic acid, a PEG-modified ceramide, a PEG-modified di alkyl amine, a PEG-modified diacylglycerol, a PEG-modified dialkylglycerol, and mixtures thereof. In certain embodiments, the one or more shielding lipid is 1,2-dimyristoyl-rac-glycero-3-methoxypolyethylene glycol-2000 (DMG-PEG2000).

In still yet other embodiments of this aspect, the one or more shielding lipids comprises one or more tertiary amino lipidated and/or PEGylated cationic peptide compounds of formula (I) or salts thereof:

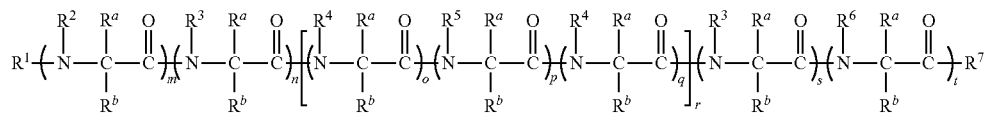

(I)

wherein:

m is an integer from 0 to 10;

n is an integer from 0 to 5;

s is an integer from 0 to 5;

t is an integer from 0 to 10;
  wherein at least one of m and t is nonzero;

r is an integer from 1 to 20;

each o is independently an integer 0, 1, or 2;

each q is independently an integer 0, 1, or 2;

each p is independently an integer 1 or 2;

$R^1$ is —H, alkyl, alkylaryl, —$COR^{1a}$ or a lipid moiety, wherein $R^{1a}$ is —H, —OH, alkyl, aryl, alkylaryl, —O-alkyl, or —O-alkylaryl;

each $R^2$ is independently an ethylene glycol moiety of the formula
  —$CH_2CH_2O(CH_2CH_2O)_uCH_3$, and wherein each u is independently an integer from 2 to 200;

each $R^3$ is independently a lipid moiety;

each $R^4$ is independently a neutral spacer moiety or a lipid moiety;

each $R^5$ is independently a cationic moiety;

each $R^6$ is independently an ethylene glycol moiety of the formula
  —$CH_2CH_2O(CH_2CH_2O)_vCH_3$, and wherein each v is independently an integer from 2 to 200;

$R^7$ is —H, alkyl, acyl, —OH, —$OR^{7a}$, —$NH_2$, —$NHR^{7a}$, or a lipid moiety, wherein $R^{7a}$ is alkyl, acyl, or a lipid moiety; and each $R^a$ and $R^b$ are independently —H, $C_1$-$C_4$-alkyl, or a side chain moiety found on a naturally- or non-naturally-occurring amino acid.

In yet other embodiments of the present aspect wherein the one or more shielding lipids comprises one or more tertiary amino lipidated and/or PEGylated cationic peptide compounds, when m is an integer from 0 to 3, each u is independently an integer from 20 to 200, optionally from 30 to 50; and when m is an integer from 4 to 10, each u is independently an integer from 2 to 10. In still yet other embodiments wherein the one or more shielding lipids comprises one or more tertiary amino lipidated and/or PEGylated cationic peptide compounds, which may be combined with one or more of any of the previous embodiments, the composition comprises one or more tertiary amino lipidated and/or PEGylated cationic peptide compounds wherein when t is an integer from 0 to 3, each v is independently an integer from 30 to 50; when t is an integer from 4 to 10, each v is independently an integer from 2 to 10. In certain embodiments, which may be combined with any of the preceding embodiments, m is 1, and u is an integer from 40 to 45; or t is 1, and v is an integer from 40 to 45.

In still other embodiments of the present aspect, the lipid components comprise by total weight of the lipid components:

40-70% w/w one or more lipidated cationic peptide compounds;

0-25% w/w cholesterol;

20-40% w/w 1,2-dioleoyl-sn-glycero-3-phosphoethanolamine (DOPE); and 1-5% w/w 1,2-dimyristoyl-rac-glycero-3-methoxypolyethylene glycol-2000 (DMG-PEG2000).

In certain embodiments, which may be combined with any one or more of the preceding embodiments, the mass ratio of cholesterol to DOPE is between 0.5:1 and 1:1.

In yet other embodiments of the present aspect, which may be combined with one or more of any of the preceding embodiments, the one or more polyanionic compounds comprises a nucleic acid. In some embodiments of the present aspect, which may be combined with one or more of any of the previous embodiments, the one or more polyanionic compounds comprises a nucleic acid and wherein the nucleic acid is an mRNA encoding a polypeptide. In certain embodiments of the present aspect, which may be combined with one or more of any of the preceding embodiments, the one or more polyanionic compounds comprises a nucleic acid and wherein the nucleic acid is an mRNA encoding a protein. In still yet another embodiment of the present aspect, which may be combined with one or more of any of the preceding embodiments, the mass ratio of the lipid components to the one or more polyanionic compounds is between 2:1 and 25:1. In certain embodiments, the mass ratio of the lipid components to the one or more polyanionic compounds is between 5:1 and 10:1.

In some embodiments, which may be combined with any one of the preceding embodiments, the composition further comprises one or more small molecule active agents or drug substance.

In yet another aspect of the present disclosure, provided herein are delivering a polyanionic compound to a cell comprising contacting the cell with the composition of the preceding aspect in any and all of its various embodiments. In certain embodiments of this aspect, the contacting is by endocytosis. In other embodiments of this aspect, which may be combined with the preceding aspect, the cell is contacted in vivo or in vitro. In certain embodiments of this aspect that include a nucleic acid encoding a polypeptide, which may be combined with either or both of the preceding embodiments, the cell expresses the polypeptide after being contacted with the composition. In still further embodiments that include a nucleic acid encoding a protein, which may be combined with one or more of the preceding embodiments, the cell expresses the protein after being contacted with the composition.

An additional aspect of this disclosure provides methods of preparing the compositions of the preceding aspect relating to compositions and any and all of its various embodiments, by combining one or more lipidated cationic peptide compounds, one or more phospholipids, one or more shielding lipids, and optionally one or more structural lipids with one or more polyanionic compounds. In an embodiment of this aspect, the compositions are formed by contacting a solution comprising comprising the one or more lipidated cationic peptide compounds, one or more phospholipids, one or more shielding lipids, and optionally one or more structural lipids with a solution comprising the one or more polyanionic compounds.

DESCRIPTION OF THE FIGURES

FIGS. 2A-2F show tertiary amino lipidated cationic peptoids generally. FIG. 2A shows the generalized structure for the tertiary amino lipidated peptoids. FIG. 2B shows an exemplary tertiary amino lipidated cationic peptoid. FIG. 2C shows exemplary lipid monomers. FIG. 2D shows exemplary cationic monomers. FIG. 2E shows exemplary spacer monomers and a polyethylene glycol monomer. FIG. 2F shows exemplary tertiary amino lipidated cationic peptoid compound 8.

FIG. 3A shows the generalized acylation reaction of a resin-bound secondary amine to acylating agent bromoacetic acid. FIG. 3B shows the reaction of the resulting acylation product with a suitable amine via nucleophilic displacement to produce the corresponding N-substituted amino acid residue. FIG. 3C and FIG. 3D show successive iterations of the acylation and nucleophilic displacement reactions to produce the desired resin-bound cationic peptide compound. FIG. 3E shows cleavage of the cationic peptide compound from the solid resin support to provide the free peptide.

FIG. 6A and FIG. 6B show the mean bioluminescence observed in the HeLa cells treated with the formulations 1-36 (FIG. 6A) and 37-72 (FIG. 6B).

FIG. 7A and FIG. 7B show the mean bioluminescence observed 6 hours after administration s with the formulations 1-36 (FIG. 7A) and 37-72 (FIG. 7B).

FIGS. 8A-8B depict bioluminescence measured in in vitro and in vivo assays for the delivery of Fluc mRNA using multicomponent lipid formulations of Lipitoid 1 with cholesterol, DOPE and DMG-PEG2000. FIG. 8A shows a plot of the observed bioluminescence signal (RLU) for an in vitro transfection survey of HeLa cells using ninety-six different multicomponent lipid formulations complexed with Fluc mRNA. FIG. 8B depicts a bar graph of the in vitro bioluminescence intensity (RLU) recorded in HeLa cells treated with Fluc mRNA alone, or Fluc mRNA formulated with commercially available lipid nanoparticle kit, with Lipitoid 1, with Lipitoid Formulation A and with Lipitoid Formulation B.

DETAILED DESCRIPTION

Figure 1:
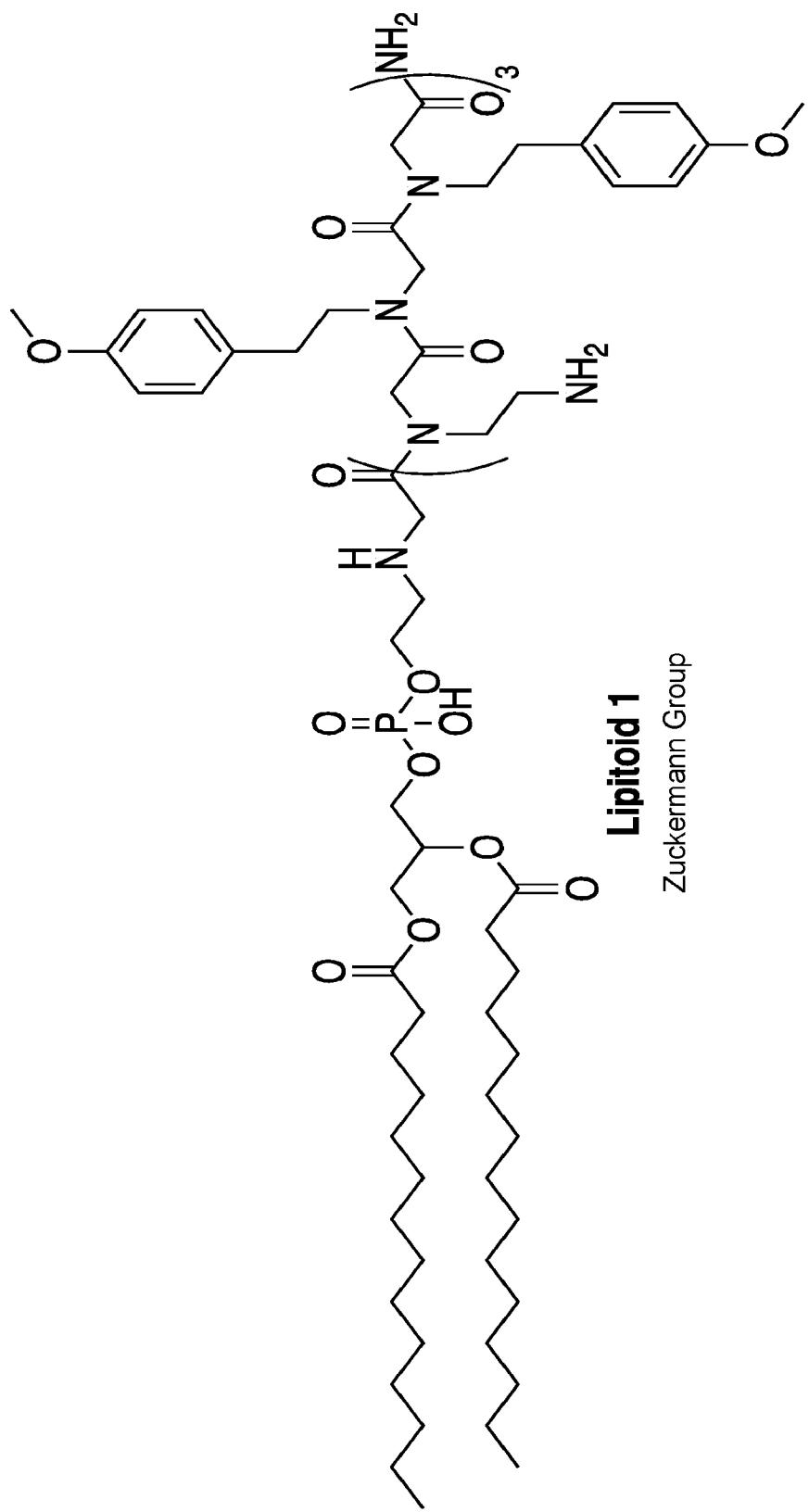
FIG. 1 shows an exemplary secondary amine phospholipidated cationic peptide "Lipitoid 1".

The following description sets forth exemplary methods, parameters and the like. It should be recognized, however, that such description is not intended as a limitation on the scope of the present disclosure but is instead provided as a description of exemplary embodiments.

The present disclosure provides multicomponent lipid compositions comprising complexes of lipidated cationic peptide compounds in combination with further lipid components, such as structural lipids, phospholipids, and shielding lipids, for the delivery of nucleic acids. The multicomponent lipid compositions and complexes therein may include cationic peptide-phospholipid conjugates, also known as lipitoids, or N-substituted cationic peptide compounds that are N-substituted with lipid moieties and/or (oligo- and/or poly)ethylene glycol moieties (referred to herein as tertiary amino lipidated and/or PEGylated cationic peptide compounds) as the cationic peptide compounds.

As described herein, the multicomponent lipid compositions comprising lipitoids and/or tertiary amino lipidated and/or PEGylated cationic peptide compounds exhibit highly efficient delivery of nucleic acid material into cells that exceeds the efficiency observed for other commercially available lipid nanoparticle formulations (i.e., from a kit) or standalone agents (e.g., Lipitoid 1 alone). Interestingly, it was further observed that lipid compositions of the present disclosure still achieved successful delivery of nucleic acids without the inclusion of structural lipids, "Alkenyl" as used herein refers to an unsaturated linear or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). The alkenyl group may be in "cis" or "trans" configurations, or alternatively in "E" or "Z" configurations. Particular alkenyl groups are those having 2 to 20 carbon atoms (a "$C_2$-$C_{20}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

The term "alkyl" refers to and includes saturated linear and branched univalent hydrocarbon structures and combination thereof, having the number of carbon atoms designated (i.e., $C_1$-$C_{10}$ means one to ten carbons). Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"). Examples of alkyl include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkylene" as used herein refers to the same residues as alkyl, but having bivalency. Particular alkylene groups are those having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), butylene (—$CH_2CH_2CH_2CH_2$—), and the like.

"Alkynyl" as used herein refers to an unsaturated linear or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

The term "aryl" refers to and includes polyunsaturated aromatic hydrocarbon groups. Aryl may contain additional fused rings (e.g., from 1 to 3 rings), including additionally fused aryl, heteroaryl, cycloalkyl, and/or heterocyclyl rings. In one variation, the aryl group contains from 6 to 14 annular carbon atoms. Examples of aryl groups include, hut are not limited to, phenyl, naphthyl, biphenyl, and the like.

"Carbonyl" refers to the group C═O.

"Complex" as used herein includes any chemical association between two or more molecules, which may be mediated by ionic interactions, hydrogen bonding, van der Waals interactions, metal-ligand coordination, other chemical forces, and combinations of one or more of the foregoing. The complexes may form higher order structures including, for example, polyplexes, coacervate complexes, nanocomplexes, nanoparticles, and microparticles.

The term "cycloalkyl" refers to and includes cyclic univalent hydrocarbon structures, which may be fully saturated, mono- or polyunsaturated, but which are non-aromatic, having the number of carbon atoms designated (e.g., $C_1$-$C_{10}$ means one to ten carbons). Cycloalkyl can consist of one ring, such as cyclohexyl, or multiple rings, such as adamantly, but excludes aryl groups. A cycloalkyl comprising more than one ring may be fused, spiro or bridged, or combinations thereof. A preferred cycloalkyl is a cyclic hydrocarbon having from 3 to 13 annular carbon atoms. A more preferred cycloalkyl is a cyclic hydrocarbon having from 3 to 8 annular carbon atoms (a "$C_3$-$C_8$ cycloalkyl"). Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like.

"Halo" or "halogen" refers to elements of the Group 17 series having atomic number 9 to 85. Preferred halo groups include fluoro, chloro, bromo and iodo. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halo; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl. Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

The term "heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. A heteroaryl group can be attached to the remainder of the molecule at an annular carbon or at an annular heteroatom. Heteroaryl may contain additional fused rings (e.g., from 1 to 3 rings), including additionally fused aryl, heteroaryl, cycloalkyl, and/or heterocyclyl rings. Examples of heteroaryl groups include, but are not limited to, pyridyl, pyrimidyl, thiophenyl, furanyl, thiazolyl, and the like.

The term "heterocycle" or "heterocyclyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl or heteroaryl. Examples of heterocyclyl groups include, but are not limited to, tetrahydropyranyl, dihydropyranyl, piperidinyl, piperazinyl, pyrrolidinyl, thiazolinyl, thiazolidinyl, tetrahydrofuranyl, tetrahydrothiophenyl, 2,3-dihydrobenzo[b]thiophen-2-yl, 4-amino-2-oxopyrimidin-1(2H)-yl, and the like.

"Oxo" refers to the moiety ═O.

"Thiocarbonyl" refers to the group C═S.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 2 to 5, 3 to 5, 2 to 3, 2 to 4, 3 to 4, 1 to 3, 1 to 4 or 1 to 5 substituents.

The term "substituted" refers to the replacement of one or more hydrogen atoms of a moiety with a monovalent or divalent radical. "Optionally substituted" indicates that the moiety may be substituted or unsubstituted. Suitable substituent groups include, for example, hydroxyl, nitro, amino (e.g., —$NH_2$ or dialkyl amino), imino, cyano, halo (such as F, Cl, Br, I), haloalkyl (such as —$CCl_3$ or —$CF_3$), thio, sulfonyl, thioamido, amidino, imidino, oxo, oxamidino, methoxamidino, imidino, guanidino, sulfonamido, carboxyl, formyl, alkyl, alkoxy, alkoxy-alkyl, alkylcarbonyl, alkylcarbonyloxy (—OCOR), aminocarbonyl, arylcarbonyl, aralkylcarbonyl, carbonylamino, heteroarylcarbonyl, heteroaralkyl-carbonyl, alkylthio, aminoalkyl, cyanoalkyl, carbamoyl (—NHCOOR- or —OCONHR-), urea (—NHCONHR-), aryl and the like, where R is any suitable group, e.g., alkyl or alkylene. In some embodiments, the optionally substituted moiety is optionally substituted only with select radicals, as described. In some embodiments, the above groups (e.g., alkyl groups) are optionally substituted with, for example, alkyl (e.g., methyl or ethyl), haloalkyl (e.g., —CCl$_3$, —CH$_2$CHCl$_2$ or —CF$_3$), cycloalkyl (e.g., —C$_3$H$_5$, —C$_4$H$_7$, —C$_5$H$_9$), amino (e.g., —NH$_2$ or dialkyl amino), alkoxy (e.g., methoxy), heterocycloalkyl (e.g., as morpholine, piperazine, piperidine, azetidine), hydroxyl, and/or heteroaryl (e.g., oxazolyl). In some embodiments, a substituent group is itself optionally substituted. In some embodiments, a substituent group is not itself substituted. The group substituted onto the substitution group can be, for example, carboxyl, halo, nitro, amino, cyano, hydroxyl, alkyl, alkenyl, alkynyl, alkoxy, aminocarbonyl, —SR, thioamido, —SO$_3$H, —SO$_2$R or cycloalkyl, where R is any suitable group, e.g., a hydrogen or alkyl.

In one aspect, the present disclosure provides compositions comprising complexes, wherein the complexes comprise one or more polyanionic compounds and three or more lipid components. In some embodiments of the foregoing, the complexes comprise one or more polyanionic compounds, one or more lipidated cationic peptide compounds, and two or more other lipid components.

In some embodiments wherein the compositions and complexes comprising one or more lipidated cationic peptide compounds with one or more polyanionic compounds and/or non-anionic compounds further comprise two or more lipid components (such as the phospholipids, structural lipids, and/or shielding lipids described herein), the compositions may be described as a lipid formulation. In certain embodiments wherein the composition comprises two or more lipid components, the lipid composition may be described as a multicomponent lipid formulation. In certain embodiments wherein the complex comprises a lipidated cationic peptide compound, a polyanionic compound, a phospholipid, a structural lipid, and a shielding lipid, the composition comprises a lipid nanoparticle. In still other embodiments wherein the composition comprises a lipid nanoparticle complex, the composition may be characterized as a lipid nanoparticle (LNP) composition.

In some embodiments, the compositions of the present disclosure comprise complexes of one or more polyanionic compounds, and lipid components, wherein the lipid components comprise optionally one or more structural lipids; one or more phospholipids, one or more shielding lipids, and one or more lipidated cationic peptide compounds. In some embodiments, the compositions of the present disclosure comprise complexes of one or more polyanionic compounds, and lipid components, wherein the lipid components comprise one or more phospholipids, one or more shielding lipids, and one or more lipidated cationic peptide compounds. In other embodiments, the compositions comprise complexes of one or more polyanionic compounds, and lipid components, wherein the lipid components comprise one or more structural lipids; one or more phospholipids, one or more shielding lipids, and one or more lipidated cationic peptide compounds.

Lipidated Cationic Peptide Compounds

The compositions of the present disclosure comprise complexes, wherein the complexes comprise one or more polyanionic compounds, and lipid components, wherein the lipid components comprise optionally one or more structural lipids; one or more phospholipids; one or more shielding lipids; and one or more lipidated cationic peptide compounds.

By virtue of their positive charge, the lipidated cationic peptide compounds in the complexes and composition can form complexes with counterbalance the negative charge on the polyanionic cargoes, thus promoting uptake of the cargoes into the target cell. The lipidated cationic peptide compounds as described herein have a net zero charge or a net positive charge. In some embodiments wherein the complex or composition comprises one or more cationic compounds, the one or more cationic compounds independently have a net zero charge or a net positive charge. In certain embodiments, the one or more lipidated cationic peptide compounds independent have a net positive charge of at least +1. It should be recognized that the net charge present on the one or more cationic compounds may vary depending upon environmental conditions. For example, in some embodiments, the one or more cationic compounds independently have a stable, net positive charge at physiologically relevant pH ranges. For example, physiological pH is at least about 5.5 and typically at least about 6.0. More typically, physiological pH is at least about 6.5. Usually, physiological pH is less than about 8.5 and typically less than about 8.0. More typically, physiological pH is less than about 7.5.

The lipidated cationic peptide compounds utilized in the compositions as provided herein may include cationic peptoid-phospholipid conjugate constructs, also known as lipitoids, or N-substituted cationic peptide compounds possessing lipid moieties and/or (oligo- and/or poly)ethylene glycol moieties throughout the peptide backbone, herein referred to as tertiary amino lipidated and/or PEGylated cationic peptide compounds. In some embodiments, the compositions of the present disclosure comprise complexes comprising one or more tertiary amino lipidated and/or PEGylated cationic peptide compounds. In other embodiments, the compositions comprise complexes comprising one or more lipitoids. In still other embodiments, the compositions comprise complexes comprising one or more tertiary amino lipidated and/or PEGylated cationic peptide compounds, one or more lipitoids, or any combinations thereof.

Tertiary Amino Lipidated and/or PEGylated Cationic Peptide Compounds

In some embodiments, the complexes and compositions of the present disclosure comprise one or more tertiary amino lipidated and/or PEGylated cationic peptide compounds. The tertiary amino lipidated and/or PEGylated cationic peptide compounds are peptide chains comprising N-substituted amino acid residues. The tertiary amino lipidated and/or PEGylated cationic peptide compounds of the present disclosure comprise an oligopeptide backbone, wherein the oligopeptide backbone comprises repeating subunits of N-substituted cationic amino acid residues optionally interleaved with N-substituted neutral ("spacer") and/or lipid amino acid residues. The oligopeptide backbone is further capped at the N- and/or C-terminus by amino acid residues that are N-substituted with lipid moieties ("N-lipidated") and/or N-substituted with oligoethylene glycol and/or polyethylene glycol ("N-PEGylated").

In some embodiments, provided herein is a tertiary amino lipidated and/or PEGylated cationic peptide compound of formula (I) or a salt thereof:

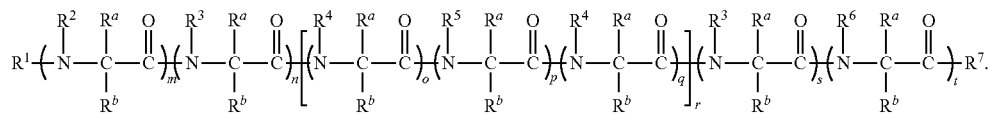

(I)

In some embodiments, the tertiary amino lipidated and/or PEGylated cationic peptide compound may be characterized by a total number of amino acid residues present in the peptide compound, wherein each amino acid residue is represented by the general structure —(NR—CR$^a$R$^b$—C(O))—. In some embodiments, the total number of amino acid residues is between 2 and 40 amino acid residues, between 2 and 30 amino acid residues, between 3 and 25 amino acid residues, between 5 and 20 amino acid residues, or between 7 and 15 amino acid residues. In certain embodiments, the tertiary amino lipidated and/or PEGylated cationic peptide compound comprises between 5 and 20 amino acid residues. In certain embodiments, the total number of amino acid residues is the sum of m, n, s, t, and [rx(o+p+q)].

In other embodiments, the tertiary amino lipidated and/or PEGylated cationic peptide compound has a net zero charge or a net positive charge. In certain embodiments wherein the tertiary amino lipidated and/or PEGylated cationic peptide compound is a tertiary amino lipidated cationic peptide compound, the tertiary amino lipidated cationic peptide compound has a net positive charge of at least +1. In other embodiments wherein the tertiary amino lipidated and/or PEGylated cationic peptide compound is a tertiary amino PEGylated cationic peptide compound or a tertiary amino lipidated and PEGylated cationic peptide compound, the cationic peptide compound has a net zero charge (i.e., is charge neutral) or a net positive charge. In some embodiments wherein the tertiary amino lipidated and/or PEGylated cationic peptide compound is a tertiary amino PEGylated cationic peptide compound or a tertiary amino lipidated and PEGylated cationic peptide compound, the cationic peptide compound has a net positive charge of +1. In certain embodiments, the tertiary amino lipidated and/or PEGylated cationic peptide compound has a net positive charge of (rxp)+.

In certain embodiments, the amino acid residues of the cationic peptide compounds described herein are N-substituted variants of naturally-occurring amino acids or non-naturally occurring amino acids, wherein the carbon side chains are represented by R$^a$ and R$^b$. The amino acid residues may be present in either D- or L-configurations. In addition, it should be recognized that the substitution of the N-position of amino acid residues may restrict free rotation of the amide bond. As such, the tertiary amino lipidated and/or PEGylated cationic peptide compounds of the present disclosure may also exist in various rotational isomeric conformations (rotamers).

In some embodiments, each R$^a$ and each R$^b$ are independently a side chain moiety found on naturally- or non-naturally-occurring amino acids. As used herein, the term "naturally-occurring amino acid" refers to Gly, Ala, Val, Leu, Ile, Ser, Thr, Cys, Met, Asp, Glu, Asn, Gln, Lys, Arg, Phe, Tyr, His, or Trp. The term "non-naturally-occurring amino acid" refers to amino acids typically not found in nature, including, for example, D-isomers of naturally-occurring amino acids, 2-aminoadipic acid, 2-aminobutyric acid, norvaline, norleucine, and ornithine. In certain embodiments, each R$^a$ and R$^b$ are independently —H, —CH$_3$, or

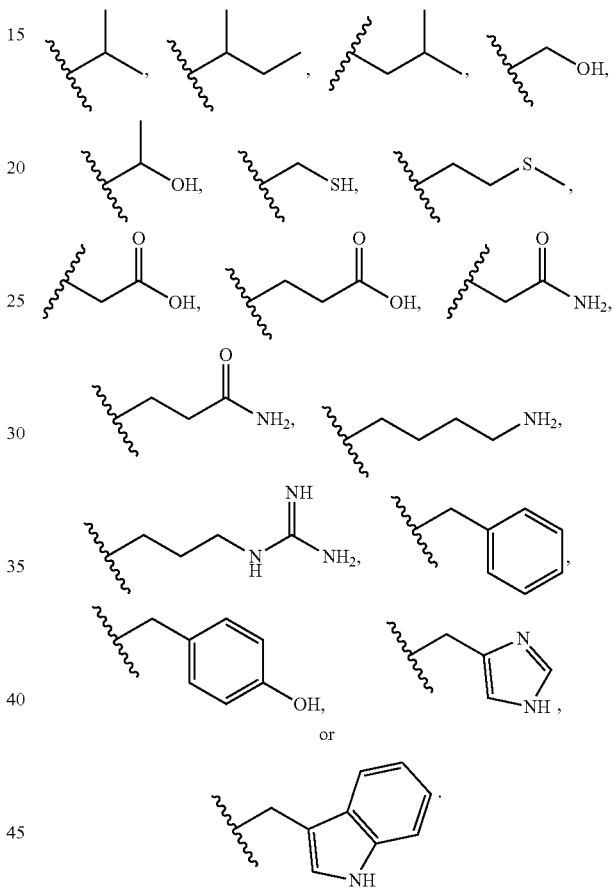

In other embodiments, each R$^a$ and each R$^b$ are independently —H or C$_1$-C$_4$-alkyl. In certain embodiments, each R$^a$ and each R$^b$ are independently —H or CH$_3$. In other embodiments, R$^a$ and R$^b$ are —H. In embodiments wherein R$^a$ and R$^b$ are —H, the tertiary amino lipidated and/or PEGylated cationic peptide compounds may also be referred to as N-lipidated and/or PEGylated polyglycine compounds or N-lipidated and/or PEGylated peptoid compounds. In certain embodiments, each R$^a$ and each R$^b$ is independently —H, C$_1$-C$_4$-alkyl, or a side chain moiety found on a naturally- or non-naturally-occurring amino acid.

Oligopeptide Backbone, or Repeating Subunits, and Structural Motifs

As described herein, the tertiary amino lipidated and/or PEGylated cationic peptide compounds may be useful for complexation with polyanionic compounds, such as nucleic acids, and for the delivery of such polyanionic compounds into cells. The tertiary amino lipidated and/or PEGylated cationic peptide compounds of the present disclosure comprise an oligopeptide backbone of repeating subunits of N-substituted cationic amino acid residues optionally interleaved with N-substituted neutral spacer amino acid residues and/or N-lipidated amino acid residues, as shown in the fragment of formula (I) below:

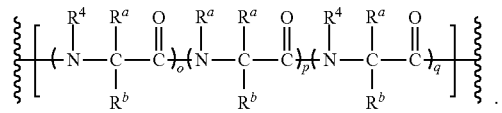

The cationic amino acid residues in the repeating subunits of the oligopeptide backbone confer positive charge to the compounds of the present disclosure, which allows for favorable electrostatic interaction with and charge neutralization of polyanionic species like nucleic acids. The interleaving of neutral or lipidated amino acid residues in between the cationic residues allows for greater control over the spatial distribution of positive charge throughout the tertiary amino lipidated and/or PEGylated cationic peptide compounds, which enables improved complexation of the cationic peptide compounds to polyanionic species having specific lengths, charge distributions and/or conformations.

In the oligopeptide backbone, r represents the number of repeating subunits of cationic and neutral and/or lipidated amino acid residues in the tertiary amino lipidated and/or PEGylated cationic peptide compound. In some embodiments, r is an integer from 1 to 25. In certain embodiments, r is an integer from 1 to 20. In other embodiments, r is an integer from 1 to 15. In some embodiments, r is an integer from 1 to 5. In certain embodiments, r is an integer from 2 to 4.

It should be recognized that each subunit r may or may not strictly be identical to the other subunits within the entire tertiary amino lipidated and/or PEGylated cationic peptide compound. For example, within a tertiary amino lipidated and/or PEGylated cationic peptide compound, each subunit r may comprise cationic amino acid residues, and optionally also neutral and/or lipidated amino acid residues, that are independently chosen with respect to the cationic and neutral and/or lipidated amino acid residues present in other subunits.

Cationic Moieties

Each repeating subunit of the tertiary amino lipidated and/or PEGylated cationic peptide compounds of the present disclosure comprises at least one cationic amino acid residue. The cationic amino acid residues provide the positive charge that enables the peptide compounds described herein to form electrostatic complexes with nucleic acids or other polyanionic compounds, by interaction with negative charges on the nucleic acids or polyanionic compounds. Complexation of nucleic acids partially or fully shields the negative charge of the nucleic acid and facilitates transport through the lipid membrane of cells and into the cell interior.

Within each subunit r, p represents the number of cationic amino acid residues present in that subunit. In some embodiments, each p is independently an integer 1 or 2. In certain embodiments, p is 1.

Each cationic amino acid residue comprises a cationic moiety $R^5$ at the N-position. It should be recognized that each cationic moiety $R^5$ may not only be independently selected within the repeating subunit of the cationic peptide compounds but also throughout the oligopeptide backbone.

A cationic moiety as described herein may be a substituent that has a stable, net positive charge at physiologically relevant pH ranges. For example, physiological pH is at least about 5.5 and typically at least about 6.0. More typically, physiological pH is at least about 6.5. Usually, physiological pH is less than about 8.5 and typically less than about 8.0. More typically, physiological pH is less than about 7.5. A cationic moiety may be characterized, for example, by a threshold $pK_a$ value for a functional group present in the moiety that is sufficient to produce a positive charge at physiological pH. In certain embodiments, the cationic moiety has a $pK_a$ value of at least 7.5. In other embodiments, the cationic moiety has a $pK_a$ between physiological pH and a more acidic pH, for example pH 4.5-5.5. In additional embodiments, substituents with multiple independent $pK_a$ values are used.

It should be recognized that the tertiary amino lipidated and/or PEGylated cationic peptide compounds described herein may comprise multiple cationic moieties along the oligopeptide backbone in close proximity to one another. When multiple cationic moieties are present along the oligopeptide backbone, the protonated or deprotonated state of certain cationic moieties may influence the $pK_a$ values of other cationic moieties in close proximity. By this mechanism, the $pK_a$ of a particular cationic moiety in the cationic peptide compounds described herein may be altered with respect to its $pK_a$ value as measured in isolation. For example, protonation of one amine in the oligopeptide backbone, having a $pK_a$~8, may lower the $pK_a$ value of a nearby cationic moiety to $pK_a$~5-6 from a normal value of ~7.5.

The capability of the tertiary amino lipidated and/or PEGylated cationic peptide compounds of the present disclosure to accommodate multiple cationic moieties at varying proximity to one another enables these cationic peptide compounds, and any complexes thereof, to respond with high sensitivity to variations in physiological pH. The sensitivity of these compounds and their complexes to changes in physiological pH may be important for facilitating delivery and release of nucleic acids into the cytosol following endosomal transport (endosome compartment pH ~4.5 to 5.5).

Cationic, or positively charged, moieties may include, for example, nitrogen-based substituents, such as those containing the following functional groups: amino, guanidino, hydrazido, and amidino. These functional groups can be either aromatic, saturated cyclic, or aliphatic. In some embodiments, each $R^5$ is independently aminoalkyl, alkylaminoalkyl, aminoalkylaminoakyl, guanidinoalkyl, N-heterocyclylalkyl, or N-heteroaryl. In other embodiments, each $R^5$ is independently

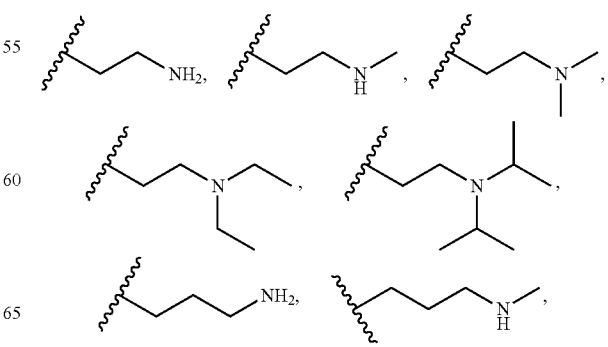

-continued

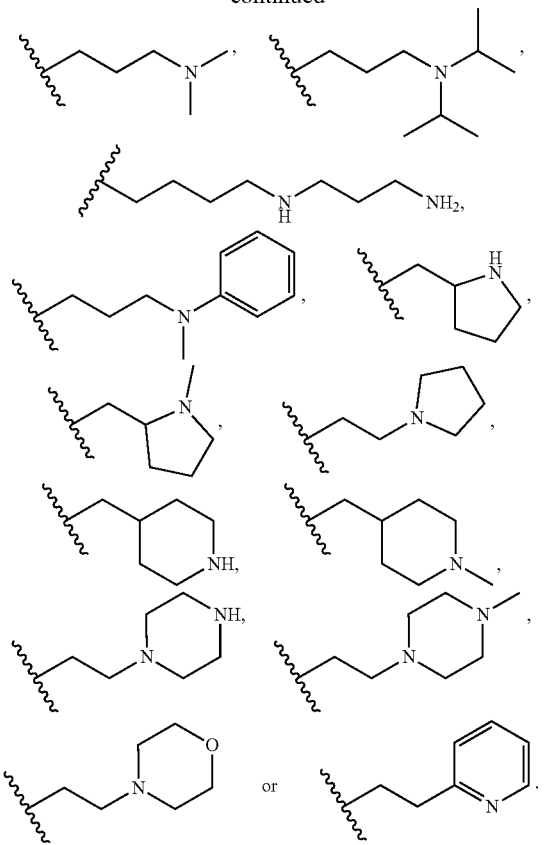

In certain embodiments, each $R^5$ is independently selected from the group consisting of:

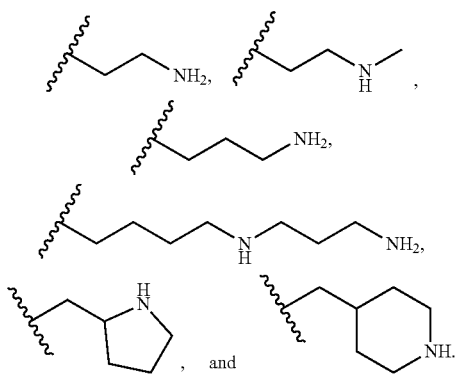

In still other embodiments, each $R^5$ is

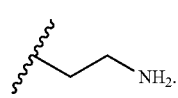

In yet further embodiments wherein a cationic residue is the terminal residue of the entire peptide compound, additional cationic moieties $R^5$ which are which are not compatible with the synthesis or deprotection conditions (such as acid-labile linkers) or for which a suitable protecting group strategy is not available (e.g. polyamines) may be utilized.

For example, in some embodiments, the cationic moiety $R^5$ of the terminal cationic residue is a polyamine. In some embodiments wherein $R^5$ of the terminal residue is a polyamine, the polyamine is

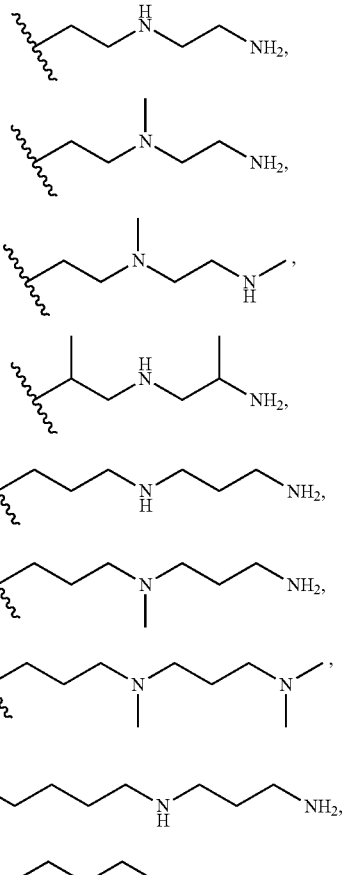

In certain embodiments, the polyamine is selected from the group consisting of

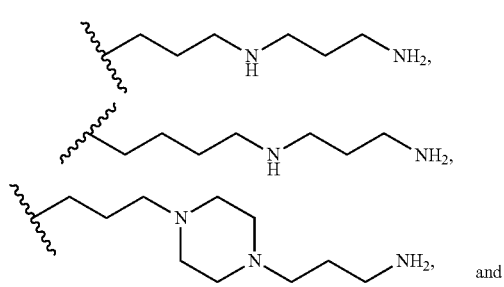

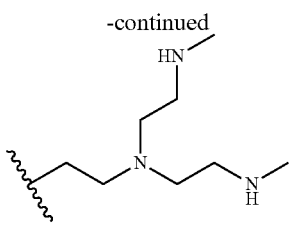

In other embodiments, the cationic moiety $R^5$ of the terminal cationic residue is a hydroxyalkyl, a hydroxyether, an alkoxyalkyl, or a hydroxylheteroalkyl. In certain embodiments, the cationic moiety $R^5$ of the terminal cationic residue is

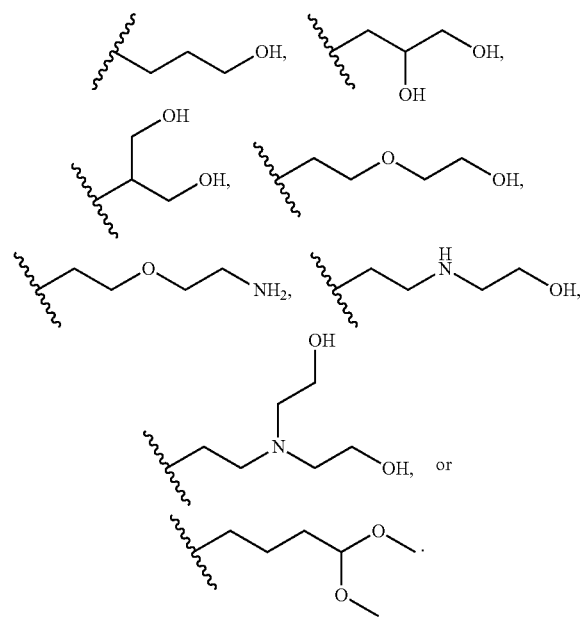

In still further embodiments, the cationic moiety $R^5$ of the terminal cationic residue is

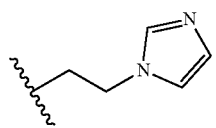

It should be further recognized that an unsubstituted nitrogen atom in the peptide chain, that is, wherein $R^5$ is hydrogen, may also serve as an ionizable cationic moiety under physiological conditions. In some embodiments, the cationic moiety $R^5$ is a hydrogen atom.

Neutral Spacer Moieties

Within the oligopeptide backbone of tertiary amino lipidated and/or PEGylated cationic peptide compounds, the cationic amino acid residues may be optionally interleaved with neutral spacer amino acid residues, possessing a neutral spacer moiety at the N-position. The neutral amino acid residues may be useful to modulate the spatial distribution of the positive charge in the tertiary amino lipidated and/or PEGylated cationic peptide compounds for improved electrostatic interactions with the polyanionic compounds, including polynucleotides, to be complexed with the cationic peptide compounds.

In each repeating subunit of the tertiary amino lipidated and/or PEGylated cationic peptide compounds, a neutral amino acid residue may present on either N- or C-terminal end of the cationic amino acid residue as one or more $R^4$ groups. In some embodiments wherein a subunit r comprises a neutral spacer moiety $R^4$, the corresponding o and/or q for each neutral spacer moiety present represent the respective numbers of neutral spacer residues bonded to the N- and C-terminal ends of the cationic amino acid residue(s) within the subunit r. In some embodiments, each o is independently an integer 0, 1, or 2. In other embodiments, each q is independently an integer 0, 1, or 2.

Each neutral spacer amino acid residue comprises a neutral spacer moiety $R^4$ at the N-position. As with the cationic moieties described herein, it should be recognized that each neutral spacer moiety $R^4$ is independently selected within the repeating subunit of the cationic peptide compounds as well as amongst the repeating subunits r of the oligopeptide backbone.

It should also be recognized that neutral spacer moieties may include any substituents that are neutral, or have zero net charge, at physiologically relevant pH ranges. In some embodiments, each neutral moiety $R^4$ is independently a $C_1$-$C_4$-alkyl substituted by cycloalkyl, heterocyclylalkyl, alkylaryl, arylalkyl, alkylheteroaryl, heteroarylalkyl, alkoxy, alkoxyalkyl, or hydroxyalkyl, wherein each cycloalkyl, heterocyclylalkyl, alkylaryl, arylalkyl, alkylheteroaryl, heteroarylalkyl, alkoxy, alkoxyalkyl, or hydroxyalkyl is optionally substituted with one or more substituents —OH, halo, or alkoxy. In still some embodiments, each neutral spacer moiety $R^4$ is independently selected from the group consisting of:

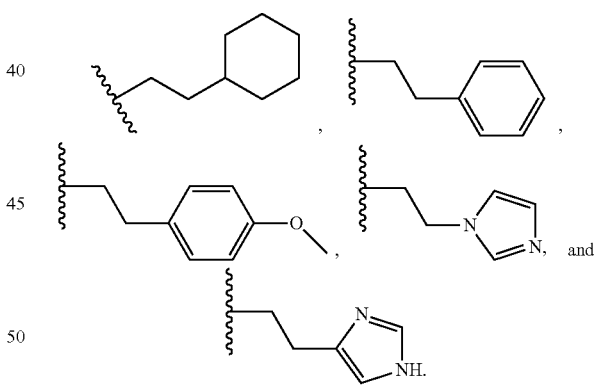

In certain embodiments, each neutral spacer moiety $R^4$ is

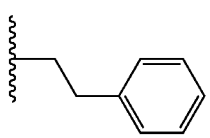

Lipid Moieties

In addition to the optional interleaving of neutral amino acid residues with cationic amino acid residues within the oligopeptide backbone of tertiary amino lipidated and/or PEGylated cationic peptide compounds, N-lipidated amino acid residues, possessing a lipid moiety at the N-position, may also optionally be interleaved with the cationic (and optional neutral spacer) amino acid residues. In some embodiments wherein the tertiary amino lipidated and/or PEGylated cationic peptide compound comprises N-lipidated amino acid residues, the tertiary amino lipidated and/or PEGylated cationic peptide compound is N-lipidated. Similar to the neutral amino acid residues, the N-lipidated amino acid residues within the oligopeptide backbone may be useful to modulate the spatial distribution of the positive charge in the tertiary amino lipidated and/or PEGylated cationic peptide compounds as well as augment their lipophilicity for improved encapsulation of polyanionic materials and endocellular delivery. The spacing of lipids along the peptoid backbone may also influence the lipid fluidity/crystallinity which is known to influence cellular uptake and endosomal release.

As with the neutral spacer residues, in each repeating subunit of the tertiary amino lipidated and/or PEGylated cationic peptide compounds, the N-lipidated amino acid residue may present on either N- or C-terminal end or both ends of the cationic amino acid residue as one or more $R^4$ groups. In some embodiments wherein a subunit r comprises a lipid moiety $R^4$, the corresponding o and/or q for each lipid moiety present may also represent the respective numbers of lipidated residues bonded to the N- and C-terminal ends of the cationic amino acid residue(s) within the subunit r. In some embodiments, each o is independently an integer 0, 1, or 2. In other embodiments, each q is independently an integer 0, 1, or 2.

Each N-lipidated amino acid residue comprises a lipid moiety $R^4$ at the N-position. As with the cationic and neutral moieties described herein, it should be recognized that each lipid moiety $R^4$ is independently selected within the repeating subunit of the cationic peptide compounds as well as amongst the repeating subunits r of the oligopeptide backbone.

Suitable lipid moieties may include, for example, optionally substituted branched or straight chain aliphatic moieties, or optionally substituted moieties derived from natural lipid compounds, including fatty acids, sterols, and isoprenoids.

In some embodiments, the lipid moieties may include branched or straight chain aliphatic moieties having from about 6 to about 50 carbon atoms or from about 10 to about 50 carbon atoms, optionally comprising one or more heteroatoms, and optionally comprising one or more double or triple bonds (i.e., saturated or mono- or poly-unsaturated). In certain embodiments, the lipid moieties may include optionally substituted aliphatic, straight chain or branched moieties, each hydrophobic tail independently having from about 8 to about 30 carbon atoms or from about 6 to about 30 carbon atoms. In certain embodiments, the lipid moieties may include, for example, aliphatic carbon chains derived from fatty acids and fatty alcohols. In some embodiments, each lipid moiety $R^4$ is independently $C_8$-$C_{24}$-alkyl or $C_8$-$C_{24}$-alkenyl, wherein the $C_8$-$C_{24}$-alkenyl is optionally mono- or poly-unsaturated. In some embodiments, each lipid moiety $R^4$ is a $C_6$-$C_{18}$ alkyl or $C_6$-$C_{18}$ alkenyl. In certain embodiments, each lipid moiety $R^4$ is $C_8$-$C_{12}$ alkyl. In still other embodiments, each lipid moiety $R^4$ is a $C_{10}$-alkyl, such as n-decyl. In other embodiments, each lipid moiety $R^4$ is independently selected from the group consisting of 2-ethylhex-1-yl, caproyl, oleyl, stearyl, linoleyl, myristyl, and lauryl.

In yet other embodiments which may be combined with any of the preceding embodiments, each lipid moiety $R^4$ is independently

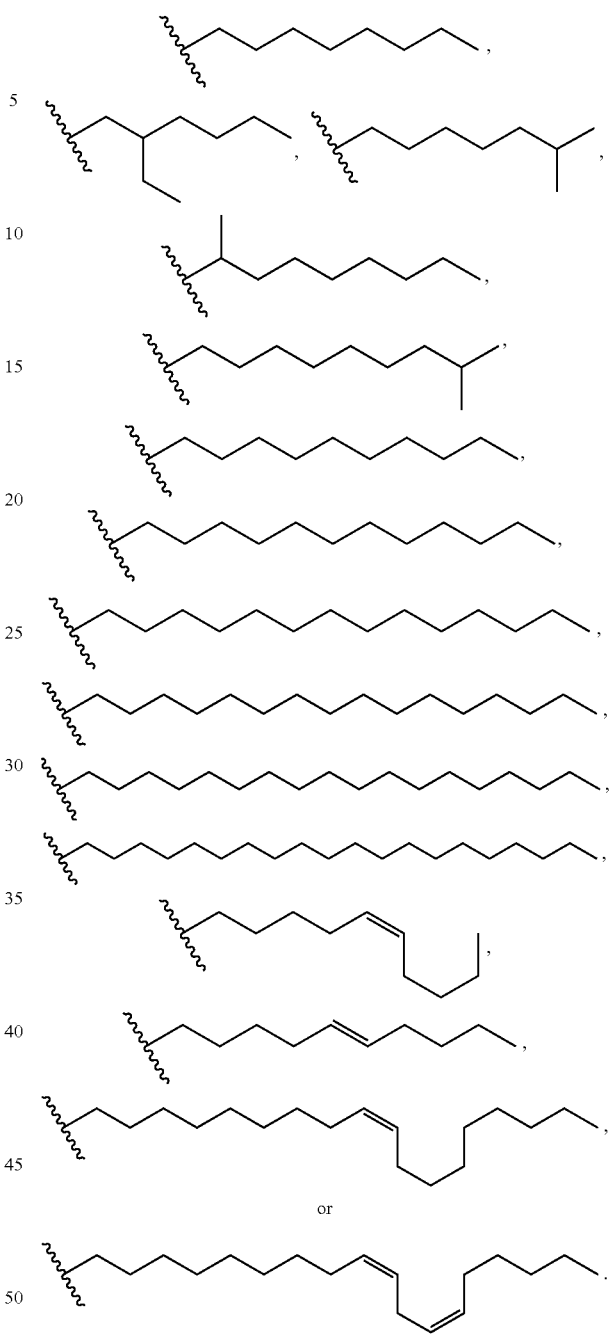

In still yet other embodiments which may be combined with any of the preceding embodiments, each lipid moiety $R^4$ is independently a lipid of the formula

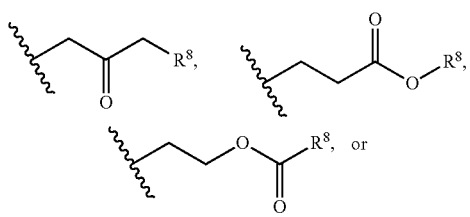

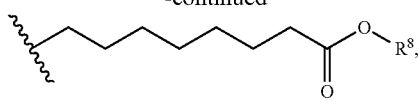

wherein $R^8$ is a branched or straight chain aliphatic moieties having from about 6 to about 50 carbon atoms or from about 10 to about 50 carbon atoms, optionally comprising one or more heteroatoms, and optionally comprising one or more double or triple bonds. In certain embodiments, each lipid moiety $R^4$ is independently

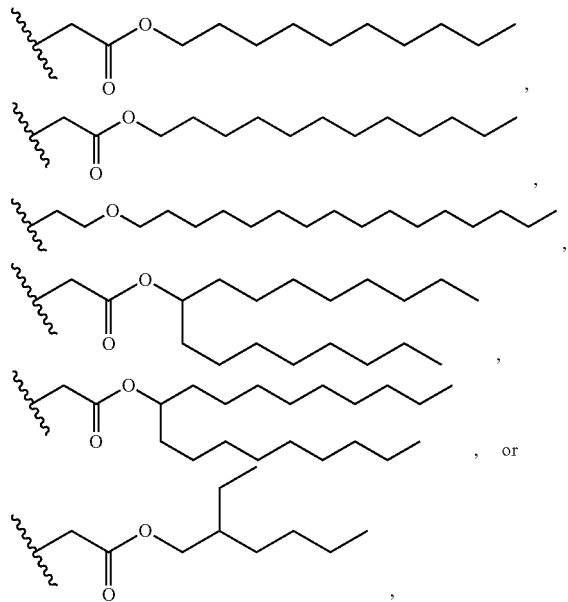

Natural lipid moieties employed in the practice of the present invention can be derived from, for example, phospholipids, glycerides (such as di- or tri-glycerides), glycosylglycerides, sphingolipids, ceramides, and saturated and unsaturated sterols, isoprenoids, and other like natural lipids.

Other suitable lipid moieties may include lipophilic carbocyclic or aromatic groups such as optionally substituted aryl, cycloalkyl, cycloalkylalkyl, or arylalkyl moieties, including for example naphthalenyl or ethylbenzyl, or lipids comprising ester functional groups including, for example, sterol esters and wax esters. In still other embodiments, the lipid moiety $R^4$ is

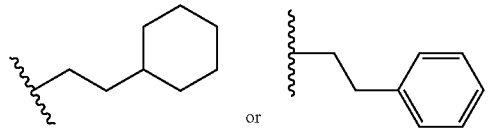

Structural Motifs

In some embodiments, the tertiary amino lipidated and/or PEGylated cationic peptide compounds of the present disclosure may comprise particular sequences or arrangements of the cationic, neutral spacer, and lipidated amino acid residues with respect to one another, which can be described similar to the various classifications of linear copolymers (random, block, alternating, periodic, stereoblock, etc.).

For example, in some embodiments wherein the tertiary amino lipidated and/or PEGylated cationic compounds comprise generic moieties $R^{cation}$, $R^{neutral}$, and $R^{lipid}$, the amino acid residues may be arranged in random sequences, in alternating sequences or block sequences. It should be understood that the representations of $R^{cation}$ and $R^{neutral}$ are equivalent to amino acid residues comprising a cationic moiety $R^5$ and neutral moiety $R^4$, respectively. The generic moiety $R^{lipid}$ may be understood to include both amino acid residues having a lipid moiety $R^4$ and lipid moiety $R^3$, depending upon the position of the N-lipidated residue in the tertiary amino lipidated and/or PEGylated cationic peptide compounds.

One example of an alternating sequence of the cationic and neutral spacer amino acid residues may be represented by $R^{cation}$—$R^{neutral}$—$R^{cation}$—$R^{neutral}$, or $R^{neutral}$—$R^{cation}$—$R^{neutral}$—$R^{cation}$. Another example of an alternating sequence of cationic and lipidated amino acid residues may be represented by $R^{cation}$—$R^{lipid}$—$R^{cation}$—$R^{lipid}$ or $R^{neutral}$—$R^{cation}$—$R^{neutral}$—$R^{cationic}$. Some examples of a block sequence may be represented by $R^{cation}$—$R^{cation}$—$R^{cation}$—$R^{neutral}$—$R^{neutral}$—$R^{neutral}$, $R^{neutral}$—$R^{neutral}$—$R^{neutral}$—$R^{cation}$—$R^{cation}$—$R^{cation}$, $R^{cation}$—$R^{cation}$—$R^{cation}$—$R^{lipid}$—$R^{lipid}$—$R^{lipid}$, or $R^{lipid}$—$R^{lipid}$—$R^{lipid}$—$R^{cation}$—$R^{cation}$—$R^{cation}$. In still some embodiments, the cationic moieties, neutral spacer moieties and lipidated moieties may be arranged in block sequences and alternating sequences for different repeating subunit segments within the overall oligopeptide compound. For example, in some embodiments, there may be repeating motifs of larger oligomer units, such as $R^{cation}$—$R^{neutral}$—$R^{neutral}$—$R^{cation}$—$R^{neutral}$—$R^{neutral}$, within the cationic peptide compound. In other embodiments, the cationic peptide compound may comprise a block of N-lipidated residues combined with a block of alternating cationic and neutral residues.

As described herein, the tertiary amino lipidated and/or PEGylated cationic peptides of the present disclosure comprise at least one cationic amino acid residue having a cationic moiety $R^5$. In some embodiments, the backbone of the tertiary amino lipidated and/or PEGylated cationic peptide compound comprises a "cationic domain" or "cationic block". The cationic domain may be understood broadly as a segment of sequential amino acid residues within the oligopeptide chain having a plurality of cationic moieties $R^5$, e.g., at least two cationic residues. In some embodiments, the tertiary amino lipidated and/or PEGylated cationic peptide compound comprises a cationic domain wherein the cationic domain comprises at least two, at least three or at least four cationic amino acid residues.

The cationic domain may include, for example, a block of amino acid residues having a plurality of $R^5$ cationic moieties in a contiguous, linear sequence (e.g., $R^5R^5R^5$ or $R^{cation}R^{cation}R^{cation}$). In some embodiments, the tertiary amino lipidated and/or PEGylated cationic peptide compound comprises a "cationic domain", wherein the tertiary amino lipidated and/or PEGylated cationic peptide compound comprises at least two, at least three, or at least four contiguous amino acid residues having $R^5$ cationic moieties.

In other embodiments, the "cationic domain" may include a block of adjacent amino acid residues wherein the plurality of cationic residues feature additional non-cationic (i.e., neutral or lipidated) residues spaced in between two cationic residues, such that none of the cationic residues within the block and directly bonded to another cationic residue. For example, in some embodiments, the tertiary amino lipidated and/or PEGylated cationic peptide compound comprises a "cationic domain", wherein the cationic domain comprises at least two cationic amino acid residues having a cationic moiety $R^5$, and wherein each of the at least two cationic amino acid residues within the cationic domain are separated by at least one or at least two amino acid residues having a neutral spacer or lipid moiety $R^4$. In some embodiments, the non-cationic residues are interleaved at regularly spaced intervals of uniform length between two cationic residues within the cationic domain. In some embodiments wherein the cationic domain comprises non-cationic residues interleaved between cationic residues, the cationic domain may be described as a domain comprising repeating (dimer, trimer, tetramer, etc.) subunits. These subunits may include but are not limited to —$R^{cation}R^{neutral}$—, —$R^{cation}R^{neutral}R^{neutral}$—, —$R^{cation}R^{lipid}$—, —$R^{cation}R^{lipid}R^{lipid}$—, —$R^{cation}R^{neutral}R^{lipid}$—, or —$R^{cation}R^{lipid}R^{neutral}$—. In other embodiments, the non-cationic residues are interspersed between two cationic residues within the cationic domain with varying numbers of non-cationic residues between each pair of cationic residues. In certain embodiments wherein the cationic domain comprises non-cationic residues interspersed between cationic residues, each pair of cationic residues are independently separated by at least one non-cationic residue.

In some embodiments wherein the tertiary amino lipidated and/or PEGylated cationic peptide compound comprises a cationic domain, each $R^5$ is

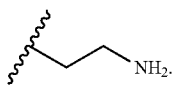

In other embodiments wherein the tertiary amino lipidated and/or PEGylated cationic peptide comprises a cationic domain, each cationic moiety $R^5$ is

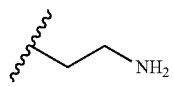

and each neutral spacer moiety is

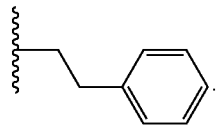 [SMILES: *CCc1ccccc1]

In certain embodiments wherein the tertiary amino lipidated and/or PEGylated cationic peptide comprises a cationic domain comprising one or more dimer or trimer subunits, each cationic moiety $R^5$ is

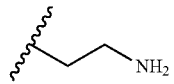

and each neutral spacer moiety is

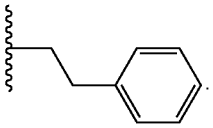 [SMILES: *CCc1ccccc1]

In still other embodiments, the tertiary amino lipidated and/or PEGylated cationic peptide comprises a cationic domain comprising one or more trimer subunits —$R^{cation}R^{neutral}R^{neutral}$—, each cationic moiety $R^5$ is

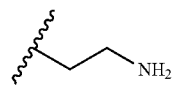

and each neutral spacer moiety is

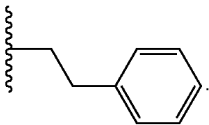 [SMILES: *CCc1ccccc1]

As described herein, the tertiary amino lipidated and/or PEGylated cationic peptide compounds of the present disclosure may comprise one or more different cationic moieties ($R^{cation1}$, $R^{cation2}$, $R^{cation3}$, etc.), one or more different neutral spacer moieties ($R^{neutral1}$, $R^{neutral2}$, $R^{neutral3}$, etc.), and/or one or more different lipid moieties ($R^{lipid1}$, $R^{lipid2}$, $R^{lipid3}$, etc.). It should be recognized that the above examples of sequences or arrangements of the generic cationic and neutral spacer amino acid residues are not intended to be limiting to the peptide compounds of the present disclosure. The cationic, neutral spacer, and lipid moieties, which may be present in random, alternating or block sequences as generally described above, may also be present in particular sequences of individual cationic moieties, neutral moieties, and lipid moieties within a larger block or alternating structural motif. For example, some exemplary arrangements of residues may include but are not limited to the following:
$R^{cation1}R^{neutral1}R^{neutral1}R^{lipid1}R^{cation1}R^{neutral1}R^{neutral1}R^{lipid1}R^{cation1}R^{neutral1}R^{neutral1}$,
$R^{cation1}R^{neutral1}R^{neutral1}R^{cation1}R^{neutral1}R^{neutral1}R^{cation1}R^{neutral1}R^{neutral1}R^{lipid1}R^{lipid1}$,
$R^{lipid1}R^{cation1}R^{neutral1}R^{lipid1}R^{cation1}R^{neutral1}R^{lipid2}R^{cation2}R^{neutral2}R^{lipid2}R^{cation2}R^{neutral2}$,
$R^{lipid1}R^{lipid2}R^{lipid3}R^{lipid4}R^{neutral1}R^{neutral2}R^{cation1}R^{neutral1}R^{neutral2}R^{lipid1}R^{lipid2}R^{lipid3}R^{lipid4}$, or
$R^{lipid1}R^{lipid2}R^{lipid1}R^{lipid2}R^{cation1}R^{neutral1}R^{cation1}R^{neutral1}R^{lipid1}R^{lipid2}R^{lipid1}R^{lipid2}$.

Side Chain Functionalization and Peptide Conjugate Compounds

As described above, the oligopeptide backbone principally comprises amino acid residues having a side chain moiety found on naturally- or non-naturally-occurring amino acids ($R^a$ and $R^b$) with cationic, neutral spacer, or lipid moieties at the N-positions ($R^4$ and $R^5$).

In one aspect, the $R^a$, $R^b$, $R^4$, and $R^5$ groups of the tertiary amino lipidated and/or PEGylated cationic peptide compounds of the present disclosure may further comprise reactive linker groups that can be used to covalently bond to a therapeutic agent and/or targeting element, such as a small molecule or antibody. These additional functionalities may also comprise cationic groups which are not compatible with the synthesis or deprotection conditions (such as acid-labile linkers) or for which a suitable protecting group strategy is not available (ex. polyamines). The reactive group(s) can, for example, be appended to an existing side chain $R^a$ and/or $R^b$ or to the cationic moiety at $R^5$, neutral spacer or lipid moiety at $R^4$ at the N-position through chemical methods known in the art. Alternatively, if the $R^a$, $R^b$, $R^4$, or $R^5$ group with the desired reactive moiety is commercially obtainable as the corresponding free amine, the corresponding free amine can be incorporated during the general synthesis of peptide chain (e.g., during submonomer synthesis).

In some embodiments, the tertiary amino lipidated and/or PEGylated cationic peptide comprises one or more amino acid residues comprising a reactive group or linker group. Suitable reactive groups may include but are not limited to esters, amides, isocyanates, thiols or "click" chemistry compatible moieties (e.g., azido, alkynyl).

In another aspect, the present disclosure further provides as a cationic compound a tertiary amino lipidated and/or PEGylated cationic peptide compound, wherein the peptide compound is covalently bound, or conjugated, to a therapeutic agent and/or targeting element. In certain embodiments, the therapeutic agent and/or targeting element is a small molecule, a peptide sequence, an antibody or an antibody fragment, an aptamer, a mono- or oligo-saccharide (e.g., galactose), or a glycan.

Linker groups or linkages that are sensitive to or labile under certain physiological conditions environments may be useful to enable targeted delivery to certain organs or cells followed by selective release of the therapeutic agent and/or polyanionic material in(to) the cell. Moreover, labile linkages may also promote elimination and clearance of the tertiary amino lipidated and/or PEGylated cationic compounds from the cell (or organ, or whole body) following delivery of polyanionic material. In certain embodiments, the linker group is selected such that the covalent bond between the tertiary amino lipidated and/or PEGylated cationic peptide compound and the therapeutic agent or targeting element is hydrolytically labile, chemically labile, pH labile, photolabile, thermally labile, or enzymatically cleavable.

Terminal (Capping) Residues and Protecting End Groups

As described herein, the tertiary amino lipidated and/or PEGylated cationic peptide compounds of the present disclosure comprise an oligopeptide backbone that is capped at its N- and/or C-terminus by amino acid residues that are N-substituted with lipid moieties ("N-lipidated") and/or N-substituted with oligoethylene glycol and/or polyethylene glycol ("N-PEGylated"). The N-lipidation of the cationic peptide compounds confers favorable lipophilicity to the compounds as well as any complexes formed between the compounds and polyanionic species. N-PEGylation provides greater control over particle formation and aggregation in vivo. The terminal amino and carboxylic acid moieties of the N- and C-terminus may be further capped with protecting end groups.

As described herein, the tertiary amino lipidated and/or PEGylated cationic peptide compounds may comprise amino acid residues that are N-lipidated and/or N-PEGylated. The cationic peptide compounds provided herein comprise at least one amino acid residue that is N-lipidated or N-PEGylated. In some embodiments, the tertiary amino lipidated and/or PEGylated cationic peptide compound is a tertiary amino lipidated cationic peptide compound. In other embodiments, the tertiary amino lipidated and/or PEGylated cationic peptide compound is a tertiary amino PEGylated cationic peptide compound. In still yet other embodiments, the tertiary amino lipidated and/or PEGylated cationic peptide compounds of the present disclosure comprise both N-lipidated and N-PEGylated amino acid residues. In some embodiments, the tertiary amino lipidated and/or PEGylated cationic peptide compound is a tertiary amino lipidated and PEGylated cationic peptide compound.

Lipid Moieties

As described above, the tertiary amino lipidated and/or PEGylated cationic peptide compounds may comprise amino acid residues at the N-terminus and/or the C-terminus, wherein the amino acid residues are N-substituted with a lipid moiety, or "N-lipidated". The incorporation of N-lipidated amino acid residues at the N- and/or C-terminus of the cationic peptide compounds described herein increase the lipophilicity of the compounds. The increased lipophilicity of the cationic peptide compounds enhances their affinity for hydrophobic environments, such as the lipid bilayer of the cell membrane, thus increasing the propensity of the tertiary amino lipidated and/or PEGylated cationic peptide compounds, and any complexes thereof with polyanionic compounds, to be transported into the cell.

In some embodiments, the tertiary amino lipidated and/or PEGylated cationic peptide compound is N-lipidated. In some embodiments, the tertiary amine lipidated and/or PEGylated cationic peptide compounds of the present disclosure comprise N-lipidated amino acid residues at the N-terminus. In other embodiments, the tertiary amine lipidated and/or PEGylated cationic peptide compounds of the present disclosure comprise N-lipidated amino acid residues at the C-terminus. In certain embodiments, the tertiary amine lipidated and/or PEGylated cationic peptide compounds of the present disclosure comprise N-lipidated amino acid residues at the N- and C-termini.

In some embodiments, the number of N-lipidated amino acid residues at the N-terminus of the cationic peptide compounds described herein is represented by n. In other embodiments, the number of N-lipidated amino acid residues at the N-terminus of the cationic peptide compounds described herein is represented by s.

In some embodiments, n is an integer from 0 to 8. In certain embodiments, n is an integer from 0 to 5. In other embodiments, n is an integer 0, 1, 2, 3, 4, 5, 6, or 7. In yet other embodiments, n is an integer 1, 2, 3, or 4. In some embodiments, s is an integer from 0 to 8. In certain embodiments, s is an integer from 0 to 5. In other embodiments, s is an integer 0, 1, 2, 3, 4, 5, 6, or 7. In still other embodiments, s is an integer 1, 2, 3, or 4. In some embodiments wherein the tertiary amino lipidated and/or PEGylated cationic peptide compound is N-lipidated, at least one of n or s is nonzero. In some embodiments, n is nonzero. In other embodiments, s is nonzero. In certain embodiments, both n and s are nonzero.

In some embodiments, the sum of n and s is an integer from 1 to 8, from 2 to 7, or from 4 to 6. In other embodiments, the sum of n and s is at least 2, at least 3, or at least 4.

In some embodiments, the tertiary amino lipidated and/or PEGylated cationic peptide compound comprises a block of N-lipidated residues, or "N-lipid block" wherein the tertiary amino lipidated and/or PEGylated cationic peptide compound comprises at least two, at least three, or at least four N-lipidated residues adjacent to one another (e.g., $R^{lipid}R^{lipid}R^{lipid}$). In some embodiments, the tertiary amino lipidated and/or PEGylated cationic peptide compound comprises a block of N-lipidated residues, wherein n is at least 2, at least 3, or at least 4. In other embodiments, the tertiary amino lipidated and/or PEGylated cationic peptide compound comprises a block of N-lipidated residues wherein s is at least 2, at least 3, or at least 4.

The N-lipidated amino acid residues in the tertiary amino lipidated and/or PEGylated cationic peptides of the present disclosure are N-substituted with lipid moieties $R^3$. Lipid moieties of the present disclosure may include hydrophobic or lipophilic moieties that are neutral (i.e., having no charge or a net charge of zero). The lipid moieties of the tertiary amino lipidated and/or PEGylated cationic compounds described herein may be either naturally or synthetically derived. Each $R^3$ is independently a lipid moiety, which may be the same or different. In some embodiments, each $R^3$ is the same. In other embodiments, each $R^3$ is different.

It should be recognized that particular sequences or arrangements of N-lipidated amino acid residues may be especially useful for improving complexation with and delivery of nucleic acids. For example, in some embodiments wherein the tertiary amino lipidated and/or PEGylated cationic compounds comprise a set of mixed N-lipidated amino acid residues having one of two different lipid moieties $R^{3a}$ and $R^{3b}$, the N-lipidated amino acid residues may be arranged on either N- or C-terminus in an alternating or block sequences. One example of an alternating sequence of N-lipidated amino acid residues may be represented by $R^{3a}$—$R^{3b}$—$R^{3a}$—$R^{3b}$ or $R^{3b}$—$R^{3a}$—$R^{3b}$—$R^{3a}$. An example of a block sequence may be represented by $R^{3a}$—$R^{3a}$—$R^{3b}$—$R^{3b}$ or $R^{3b}$—$R^{3b}$—$R^{3a}$—$R^{3a}$. In other embodiments, the sequence of N-lipidated amino acid residues may be ordered at random. It should be recognized that the above examples of sequences or arrangements of two N-lipidated amino acid residues are not intended to be limiting. Moreover, the tertiary amino lipidated and/or PEGylated cationic peptide compounds of the present disclosure may comprise two or more different lipid moieties of $R^3$, which may be present in random, alternating or block sequences as generally described above.

Suitable lipid moieties may include, for example, optionally substituted branched or straight chain aliphatic moieties, or optionally substituted moieties derived from natural lipid compounds, including fatty acids, sterols, and isoprenoids.

In some embodiments, the lipid moieties may include branched or straight chain aliphatic moieties having from about 6 to about 50 carbon atoms or from about 10 to about 50 carbon atoms, optionally comprising one or more heteroatoms, and optionally comprising one or more double or triple bonds (i.e., saturated or mono- or poly-unsaturated). In certain embodiments, the lipid moieties may include optionally substituted aliphatic, straight chain or branched moieties, each hydrophobic tail independently having from about 8 to about 30 carbon atoms or from about 6 to about 30 carbon atoms. In certain embodiments, the lipid moieties may include, for example, aliphatic carbon chains derived from fatty acids and fatty alcohols. In some embodiments, each $R^3$ is independently $C_8$-$C_{24}$-alkyl or $C_8$-$C_{24}$-alkenyl, wherein the $C_8$-$C_{24}$-alkenyl is optionally mono- or poly-unsaturated. In some embodiments, each $R^3$ is a $C_6$-$C_{18}$ alkyl or $C_6$-$C_{18}$ alkenyl. In certain embodiments, each $R^3$ is $C_8$-$C_{12}$ alkyl. In still other embodiments, each $R^3$ is a $C_{10}$-alkyl, such as n-decyl. In some embodiments, each $R^3$ is independently selected from the group consisting of 3-ethylhex-1-yl, caprylyl, caproyl, oleyl, stearyl, linoleyl, myristyl, and lauryl. In other embodiments, each $R^3$ is independently selected from the group consisting of oleyl, stearyl, linoleyl, myristyl, and lauryl.

In yet other embodiments which may be combined with any of the preceding embodiments, each $R^3$ is independently

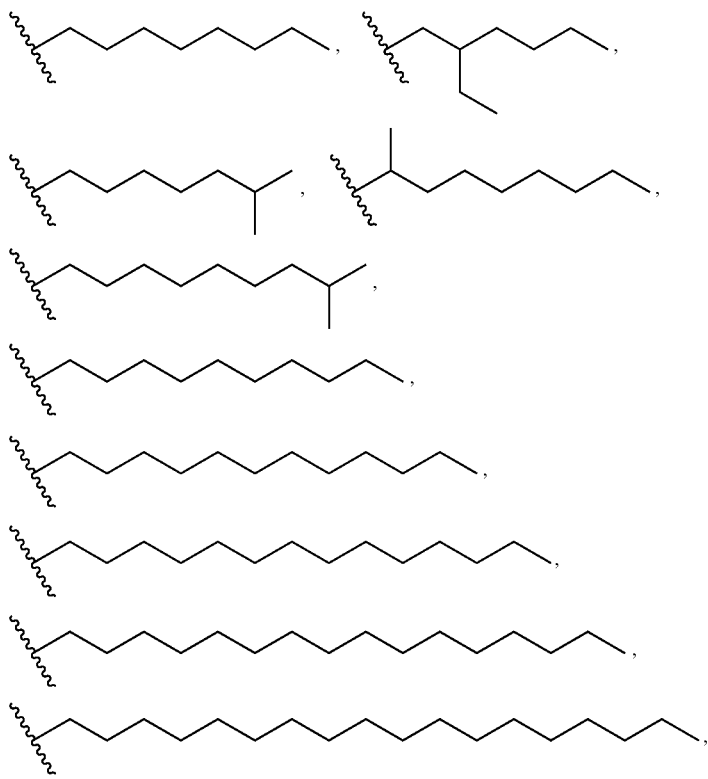

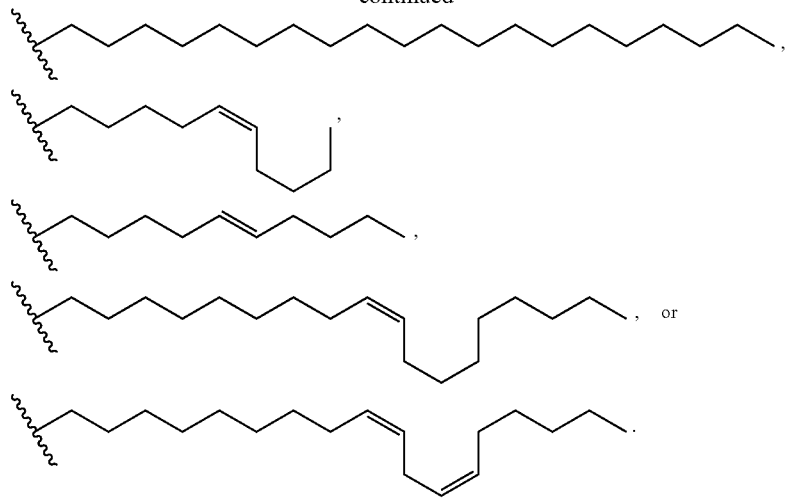

In still yet other embodiments which may be combined with any of the preceding embodiments, each $R^3$ is independently a lipid of the formula

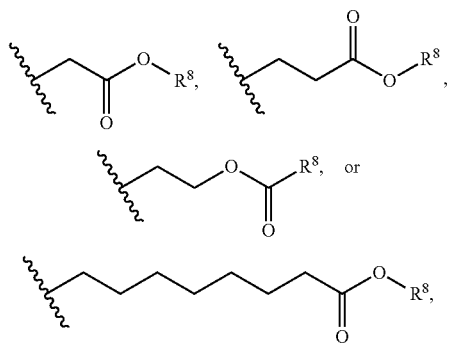

wherein $R^8$ is a branched or straight chain aliphatic moieties having from about 6 to about 50 carbon atoms or from about 10 to about 50 carbon atoms, optionally comprising one or more heteroatoms, and optionally comprising one or more double or triple bonds. In certain embodiments, each $R^3$ is independently

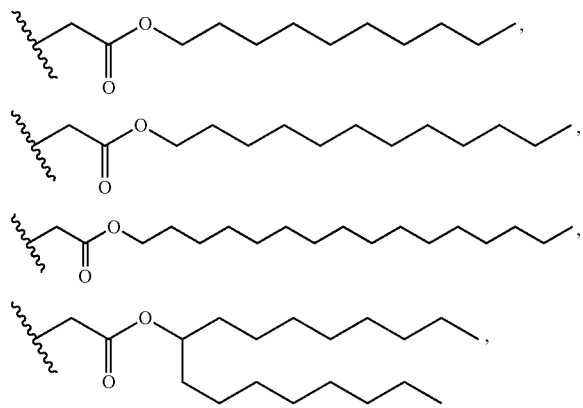

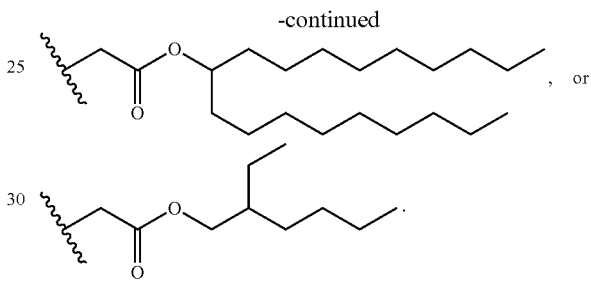

Natural lipid moieties employed in the practice of the present invention can be derived from, for example, phospholipids, glycerides (such as di- or tri-glycerides), glycosylglycerides, sphingolipids, ceramides, and saturated and unsaturated sterols, isoprenoids, and other like natural lipids.

Other suitable lipid moieties may include lipophilic carbocyclic or aromatic groups such as optionally substituted aryl, cycloalkyl, cycloalkylalkyl, or arylalkyl moieties, including for example naphthalenyl or ethylbenzyl, or lipids comprising ester functional groups including, for example, sterol esters and wax esters. In still other embodiments, the lipid moiety $R^4$ is

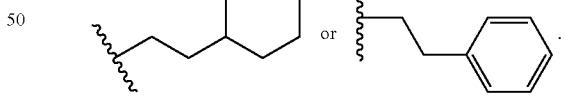

Ethylene Glycol Moieties

The tertiary amino lipidated and/or PEGylated cationic peptides of the present disclosure may comprise capping amino acid residues at the N- and/or C-terminus which are N-substituted by oligomers or polymers of ethylene glycol, that is, N-substituted with oligoethylene glycol and/or polyethylene glycol. The incorporation of oligo- and/or polyethylene glycol moieties into the tertiary amino lipidated and/or PEGylated cationic peptide compounds described herein may facilitate particle stability of complexes formed with nucleic acids and prevent particle aggregation in vivo.

It should be recognized that the term "PEGylated" is used herein to describe cationic peptide compounds comprising terminal amino acid residues which may be N-substituted with oligoethylene glycol, or polyethylene glycol, or a combination thereof. In some embodiments, the tertiary amino lipidated and/or PEGylated cationic peptide compounds provided herein are N-PEGylated.

In some embodiments, the tertiary amino lipidated and/or PEGylated cationic peptide compound comprises N-PEGylated amino acid residues at the N-terminus, as shown in the fragment of Formula (I) below:

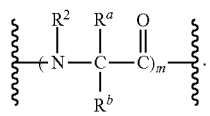

In certain embodiments wherein the tertiary amino lipidated and/or PEGylated cationic peptide compound comprises N-PEGylated amino acid residues at the N-terminus, m represents the number of N-PEGylated amino acid residues at the N-terminus, and each $R^2$ is independently an ethylene glycol moiety of the formula $-CH_2CH_2O(CH_2CH_2O)_uR^{2a}$, wherein $R^{2a}$ is $-H$ or $C_1$-$C_4$-alkyl. In some embodiments, $R^{2a}$ is $-H$, $-CH_3$, or $CH_2CH_3$. In certain embodiments, $R^{2a}$ is $-H$. In other embodiments, $R^{2a}$ is $-CH_3$. In still yet other embodiments, $R^{2a}$ is $-CH_2CH_3$.

In some embodiments, m is an integer from 0 to 10, an integer from 0 to 3, or an integer from 4 to 10. In some embodiments, each u is independently an integer from 2 to 200, an integer 2 to 100, an integer from 2 to 50, an integer from 50 to 200, an integer from 50 to 100, an integer from 100 to 200, or an integer from 150 to 200.

In certain embodiments, m is an integer from 0 to 3, and each u is an integer from 20 to 200, or optionally from 30 to 50. In certain embodiments, m is an integer from 0 to 3, and u is an integer from 40 to 45. In still yet other embodiments, m is 1, and u is an integer from 40 to 45. In other embodiments, m is an integer from 4 to 10, and each u is an integer from 2 to 10. In certain embodiments, m is an integer from 4 to 10, and u is an integer from 2 to 5. In still yet other embodiments, m is an integer from 7 to 10, and u is 3.

In some embodiments, the tertiary amino lipidated and/or PEGylated cationic peptide compound comprises N-PEGylated amino acid residues at the C-terminus, as shown in the fragment of Formula (I) below:

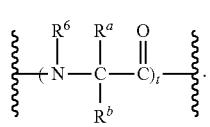

In certain embodiments wherein the tertiary amino lipidated and/or PEGylated cationic peptide compound comprises N-PEGylated amino acid residues at the C-terminus, t represents the number of N-PEGylated amino acid residues at the N-terminus, and each $R^6$ is independently an ethylene glycol moiety of the formula $-CH_2CH_2O(CH_2CH_2O)_uR^{6a}$, wherein $R^{6a}$ is $-H$ or $C_1$-$C_4$-alkyl. In some embodiments, $R^{6a}$ is $-H$, $-CH_3$, or $CH_2CH_3$. In certain embodiments, $R^{6a}$ is $-H$. In other embodiments, $R^{6a}$ is $-CH_3$. In still yet other embodiments, $R^{6a}$ is $-CH_2CH_3$.

In some embodiments, t is an integer from 0 to 10, an integer from 0 to 3, or an integer from 4 to 10. In some embodiments, each u is independently an integer from 2 to 200, an integer 2 to 100, an integer from 2 to 50, an integer from 50 to 200, an integer from 50 to 100, an integer from 100 to 200, or an integer from 150 to 200.

In some embodiments, t is an integer from 0 to 3, and each v is an integer from 30 to 50. In certain embodiments, t is an integer from 0 to 3, and v is an integer from 40 to 45. In still yet other embodiments, t is 1, and v is an integer from 40 to 45. In other embodiments, t is an integer from 4 to 10, and each v is an integer from 2 to 10. In certain embodiments, t is an integer from 4 to 10, and v is an integer from 2 to 5. In still yet other embodiments, t is an integer from 7 to 10, and v is 3.

In some embodiments wherein the tertiary amino lipidated and/or PEGylated cationic peptide compound is N-PEGylated, at least one of III or t is nonzero. In some embodiments, m is nonzero. In other embodiments, t is nonzero. In certain embodiments, both m and t are nonzero.

N-Lipidated and/or N-PEGylated

As described herein, the tertiary amino lipidated and/or PEGylated cationic peptide compounds of the present disclosure may comprise amino acid residues that are N-lipidated and/or N-PEGylated. The cationic peptide compounds provided herein comprise at least one amino acid residue that is N-lipidated or N-PEGylated. In some embodiments of the tertiary amino lipidated and/or PEGylated cationic peptide compound, at least one of m, n, s, or t is nonzero.

In some embodiments, the tertiary amino lipidated and/or PEGylated cationic peptide compound is a tertiary amino lipidated cationic peptide compound wherein at least one of n and s is nonzero. In certain embodiments, both n and s are nonzero. In still certain embodiments, the tertiary amino lipidated and/or PEGylated cationic peptide compound of formula (I) is a tertiary amino lipidated cationic peptide compound of formula (Ia):

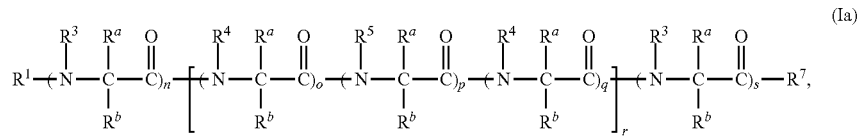

wherein at least one of n and s is nonzero, and wherein $R^1$, $R^3$, $R^4$, $R^5$, $R^7$, $R^a$, $R^b$, o, p, q, and r are as defined for formula (I). In certain embodiments of the compound of formula (Ia), both n and s are nonzero.

In other embodiments, the tertiary amino lipidated and/or PEGylated cationic peptide compound is a tertiary amino PEGylated cationic peptide compound wherein at least one of m and t is nonzero. In certain embodiments, both m and t are nonzero. In certain embodiments, both m and t are nonzero. In other embodiments, the tertiary amino lipidated and/or PEGylated cationic peptide compound of formula (I) is a tertiary amino PEGylated cationic peptide compound of formula (Ib):

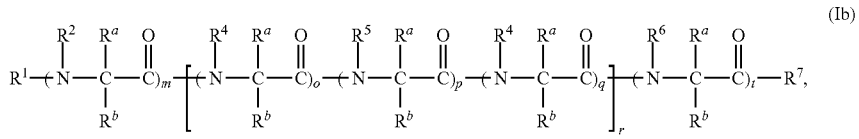

(Ib)

wherein at least one of m and t is nonzero, and wherein $R^1$, $R^2$, $R^4$, $R^5$, $R^6$, $R^7$, $R^a$, $R^b$, o, p, q, and r are as defined for formula (I). In certain embodiments of the compound of formula (Ib), both in and t are nonzero.

In still yet other embodiments, the tertiary amino lipidated and/or PEGylated cationic peptide compounds of the present disclosure comprise both N-lipidated and N-PEGylated amino acid residues. In some embodiments, the tertiary amino lipidated and/or PEGylated cationic peptide compound is a tertiary amino lipidated and PEGylated cationic peptide compound. In certain embodiments wherein the tertiary amino lipidated and/or PEGylated cationic peptide compound is a tertiary amino lipidated and PEGylated cationic peptide compound, at least one of in and t is nonzero and at least one of n and s is nonzero.

In still further embodiments, the tertiary amino lipidated and/or PEGylated cationic peptide compound of formula (I) is a tertiary amino lipidated and PEGylated cationic peptide compound of formula (Ic):

oligoethylene glycol or polyethylene glycol moiety, wherein $R^{1a}$ is —H, —OH, alkyl, aryl, alkylaryl, —O-alkyl, —O-alkylaryl, or a lipid moiety. In certain embodiments, $R^1$ is —H, alkyl, alkylaryl, —COR$^{1a}$, or a lipid moiety, wherein $R^{1a}$ is —H, —OH, alkyl, aryl, alkylaryl, —O-alkyl, or —O-alkylaryl. In certain embodiments wherein $R^1$ is a lipid moiety, the lipid moiety is not a phospholipid. In still other embodiments wherein $R^1$ is alkyl or —COR$^{1a}$ wherein $R^{1a}$ is alkyl, the alkyl is optionally substituted by —OH or halo.

In other embodiments, the tertiary amino lipidated and/or PEGylated cationic peptide compound comprises a protecting or end capping group $R^7$ at the C-terminal residue. In some embodiments, $R^7$ is —H, alkyl, acyl, —OH, —OR$^{7a}$, —NH$_2$, —NHR$^{7a}$, a cationic moiety, a lipid moiety, or an oligoethylene glycol or polyethylene glycol moiety, wherein $R^{7a}$ is alkyl, acyl, or a lipid moiety. In some embodiments, $R^7$ is —H, alkyl, acyl, —OH, —OR$^{7a}$, —NH$_2$, —NHR$^{7a}$, or a lipid moiety, wherein $R^{7a}$ is alkyl, acyl, or a lipid moiety.

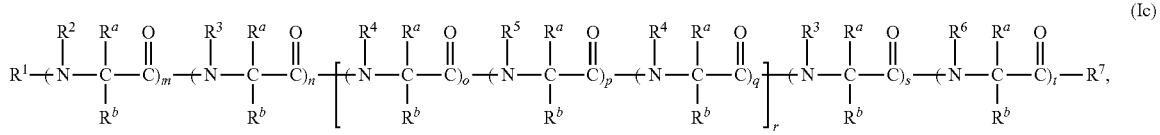

(Ic)

wherein at least one of m and t is nonzero, and at least one of n and s is nonzero, and wherein $R^1$, $R^2$, $R^3$, $R^4$, $R^5$, $R^6$, $R^7$, $R^a$, $R^b$, o, p, q, and r are as defined for formula (I).

In other embodiments, the tertiary amino lipidated and/or PEGylated cationic peptide compounds of the present disclosure may also comprise N-substituted amino acid residues having other neutral shielding polymers or moieties at the N- or C-terminus that provide a similar shielding effect as N-PEGylated residues. These may include such examples as hydroxylalkyls, hyaluronic acid, polysaccharides, polyphosphates and polyphosphoesters, poly(vinyl pyrrolidone), polyols, hydrophilic polypeptides, or other synthetic hydrophilic polymers.

N- and C-Terminal End Groups

The tertiary amino lipidated and/or PEGylated cationic peptide compounds of the present disclosure may be provided with the N-terminus and C-terminus in their free amine and free acid forms, respectively, or in protected forms. In some embodiments, the tertiary amino lipidated and/or PEGylated cationic peptide compound comprises further protecting or end capping groups at the N- and/or C-terminal residues.

In some embodiments, the tertiary amino lipidated and/or PEGylated cationic peptide compound comprises a protecting or end capping group $R^1$ at the N-terminal residue. In some embodiments, $R^1$ is —H, alkyl, alkylaryl, —COR$^{1a}$, —CH$_2$—COR$^{1a}$, a cationic moiety, a lipid moiety, or an In certain embodiments wherein $R^7$ is a lipid moiety, the lipid moiety is not a phospholipid.

In still further embodiments, the N- and C-terminus of the tertiary amino lipidated and/or PEGylated cationic peptide compound may be selected or further modified such that $R^1$ and $R^7$ possess additional functional groups such as reactive linker groups.

In some embodiments, R1 and/or $R^7$ of the tertiary amino lipidated and/or PEGylated cationic peptide independently comprises one or more reactive linker groups. Suitable reactive groups may include but are not limited to esters, amides, isocyanates, thiols or "click" chemistry compatible moieties (e.g., azido, alkynyl).

Reactive linker groups may in turn be used to covalently bind other useful compounds, including targeting elements or therapeutic agents, to the peptide compound. In some embodiments, the tertiary amino lipidated and/or PEGylated cationic peptide compound is covalently bound, or conjugated, to a therapeutic agent and/or targeting element. In certain embodiments, the therapeutic agent and/or targeting element is a small molecule, an antibody or an antibody fragment.

In addition, additional functional groups for $R^1$ and $R^7$ may also comprise cationic groups which are not compatible with the synthesis or deprotection conditions (such as acid-labile linkers) or for which a suitable protecting group strategy is not available (e.g. polyamines). In yet further embodiments, $R^1$ is a polyamine. In some embodiments wherein $R^1$ is a polyamine, the polyamine is In certain embodiments, the polyamine is selected from the group consisting of

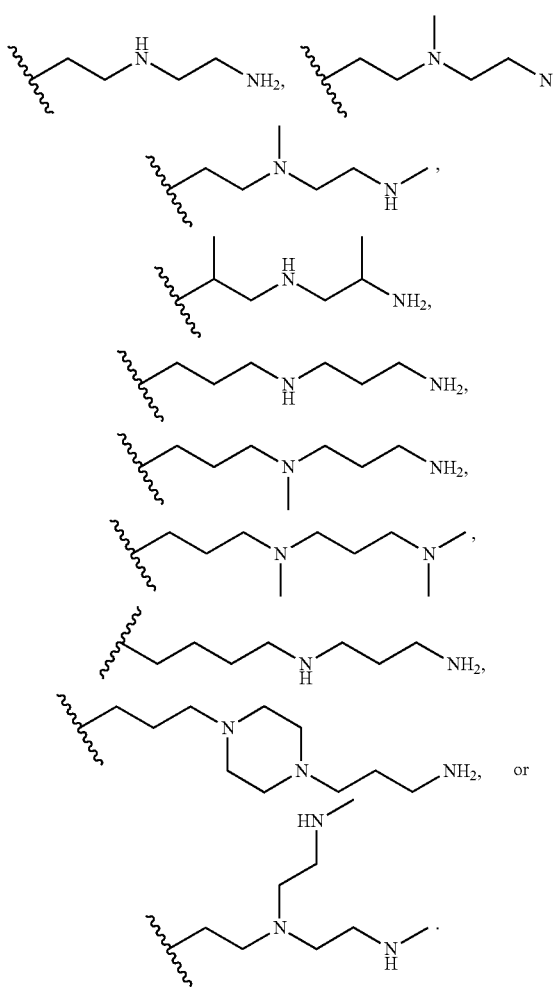

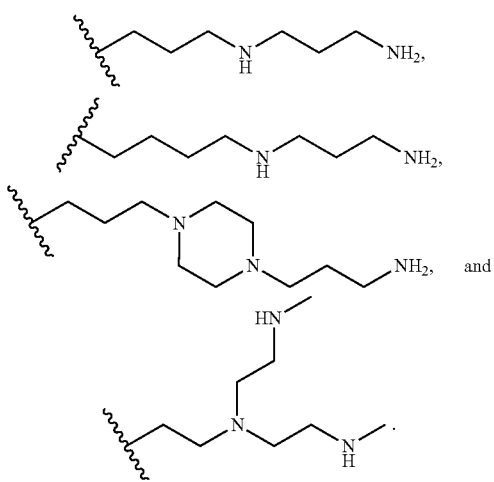

As described above, linker groups or linkages that are sensitive to or labile under certain physiological conditions environments may facilitate targeted delivery polyanionic material to specific cells and improve certain pharmacokinetic properties such as elimination. In certain embodiments, the linker group is selected such that the covalent bond between the tertiary amino lipidated and/or PEGylated cationic peptide compound and the therapeutic agent or targeting element is hydrolytically labile, chemically labile, pH labile, photolabile, thermally labile, or enzymatically cleavable.

Combinations of Tertiary Amino Lipidated and/or PEGylated Cationic Peptide Compounds The complexes and compositions of the present disclosure may comprise one or more cationic compounds. In some embodiments, the complexes described herein may comprise one or more tertiary amino lipidated and/or PEGylated cationic peptide compounds of formula (I). The use of mixtures and combinations of multiple cationic peptide compounds of the present disclosure in a single complex may enable the preparation of formulations tailored for specific pharmacokinetic and pharmacodynamics properties. Pharmacokinetic and pharmacodynamics properties of relevance may include but are not limited to biodistribution, immunogenicity, formulation stability, encapsulation percentage, transfection efficiency, plasma half-life, etc. Different combinations of these properties may be required for different applications.

For example, in certain embodiments, the complex or composition may comprise a combination of one or more tertiary amino lipidated and/or PEGylated cationic peptide compounds which are cation-rich with one or more tertiary amino lipidated and/or PEGylated cationic peptide compounds which are highly lipidated and/or contain at least one PEG moiety. In theory, such a combination could confer improved delivery of polyanionic compounds by providing greater charge stabilization (via the cation-rich peptide compounds) along with greater lipophilic shielding (by virtue of the lipidated peptide compounds). It should further be recognized that the individual amounts of each of the individual tertiary amino lipidated and/or PEGylated cationic peptide compounds may be adjusted to achieve the desired properties.

Synthesis of Tertiary Amino Lipidated and/or PEGylated Cationic Peptide Compounds In another aspect, provided herein are methods of preparing the tertiary amino lipidated and/or PEGylated cationic peptide compounds described herein.

The tertiary amino lipidated and/or PEGylated cationic peptide compounds of the present disclosure may be synthesized without the need for additional linker species to conjugate a lipid moiety to the oligopeptide core. For the tertiary amino lipidated and/or PEGylated cationic peptide compounds described herein, the lipid and ethylene glycol moieties are covalently and directly bound to nitrogen atoms within the peptide itself, that is to say, at the amide nitrogen or N-position in the amino acid residues. Thus, the tertiary amino lipidated and/or PEGylated cationic peptides may be synthesized entirely by methods known in the art for producing N-substituted residues in a peptide chain.

The tertiary amino lipidated and/or PEGylated cationic peptide compounds may be prepared by a series of acylation (amidation) and nucleophilic displacement (amination) reactions for each amino acid residue to be added, regardless of whether the residue has a cationic, neutral, lipid, or oligo-/polyethylene glycol moiety at the N-position. The cationic peptide compounds described herein are synthesized by sequential addition of individual residues to the peptide chain. The sequential addition of residues may be carried out in repetition until the desired sequence and length of amino acids is achieved.

The compounds of the present invention can be synthesized by both solid-phase and solution-phase methods. An exemplary method for preparing N-substituted peptides, including the tertiary amino lipidated and/or PEGylated cationic peptide compounds described herein, by solid-phase synthesis is discussed below and shown in FIGS. 3A-3E.

Figure 3A:
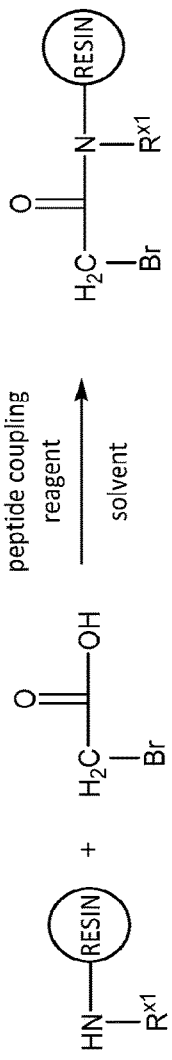
FIGS. 3A-3E show an exemplary process for preparing tertiary amino lipidated and/or PEGylated cationic peptide compounds via sequential addition of amino acid residues in the solid-phase.

As shown in FIG. 3A, a solid resin support having a terminal secondary amine is provided at the beginning of the synthesis. An acylating agent is added to the terminal secondary amine with a suitable peptide coupling reagent and solvent to form an amide bond between the terminal secondary amine and the acylating agent. The acylating agent is preferably an acetylating agent. The acylating agent comprises at least two suitable leaving groups to facilitate amidation and subsequent amination at the α-carbon. In certain embodiments, the acylating agent is a haloacetic acid. In other embodiments, the acylating agent is bromoacetic acid.

Figure 3B:
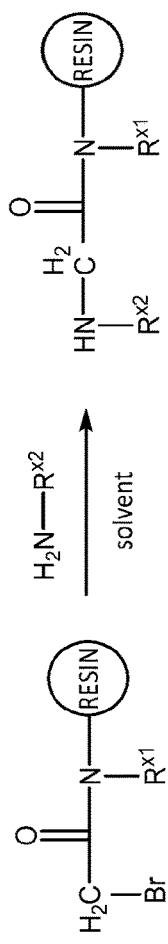
Figure 3C:
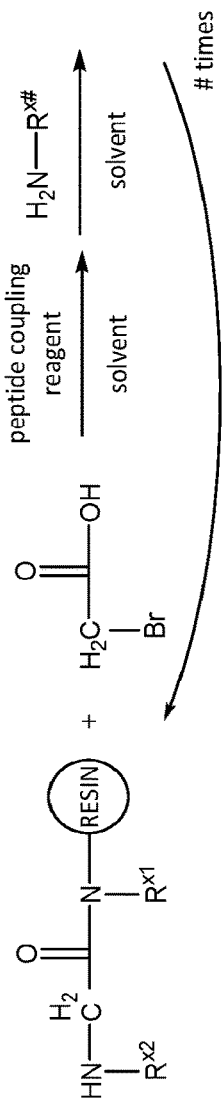

In FIG. 3B, the acylation product produced in FIG. 3A is reacted with the desired substituted primary or secondary amine to provide the corresponding N-substituted terminal amino acid residue. The selected primary or secondary amine displaces a leaving group, such as bromine in bromoacetic acid, on the α-carbon to produce the corresponding amination product. In some embodiments, the primary or secondary amine is an amine selected from the group consisting of $NHR^pR^2$, $NHR^pR^3$, $NHR^pR^4$, $NHR^pR^5$, and $NHR^pR^6$, wherein $R^p$ is —H or a protecting group, and wherein $R^2$, $R^3$, $R^4$, $R^5$, and $R^6$ are as defined for the tertiary amino lipidated and/or PEGylated cationic peptide compound as described herein.

Figure 3D:
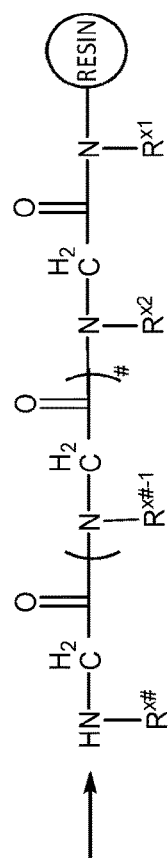
Figure 3E:
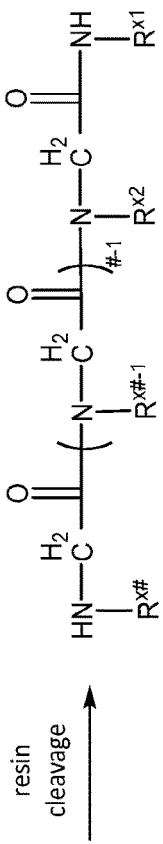

The amidation and amination reactions are repeated in series (FIG. 3C) until the desired peptide sequence is achieved (FIG. 3D). It should be recognized that the method of preparing the tertiary amino lipidated and/or PEGylated cationic peptide compound as described herein may further comprise protection and deprotection steps to prevent any undesired reactions with reactive moieties in the peptide chain over the course of the successive amidation/amination reactions. For example, protecting groups $R^p$ may be added to the side chains at the α-carbon(s) and/or N-substituent(s) anywhere along the peptide compounds described herein during synthesis. Suitable protecting groups $R^p$ may include any protecting groups known in the art, particularly those that are suitable for peptide synthesis in orthogonal protection schemes, such as Boc/Bzl or Fmoc/tBu.

The incorporation of end groups at the N- and C-termini ($R^1$ and $R^7$) as well as functionalization of end groups and/or side chains of amino acid residues ($R^a$, $R^b$, $R^4$, $R^5$) along the oligopeptide backbone can be carried out by methods known in the art. A person having ordinary skill in the art would recognize that the selection of suitable methods and the timing of the additional functionalization step(s) relative to the overall solid-phase synthesis will depend upon the end groups and/or linker groups to be added, as well as compatibility of said methods with other moieties and/or protecting groups present on the peptide compounds.

The desired peptide compound is cleaved from the solid resin support (FIG. 3E) under suitable reaction conditions, such as acidic conditions including hydrochloric acid, hydrobromic acid, or trifluoroacetic acid, depending upon any protection scheme utilized in the synthesis as described above. Cleavage of the tertiary amino lipidated and/or PEGylated cationic peptide compound from the solid resin support produces the corresponding free cationic peptide compound in solution.

Further steps may be undertaken to isolate and purify the cationic peptide compound from solution, including for example filtration of the peptide-containing solution from the solid resin support and lyophilization of the isolated filtrate to provide a solid product.

Due to the acidic conditions employed to effect resin cleavage, it should be recognized that the tertiary amino lipidated and/or PEGylated cationic peptide compound may exist in the corresponding acid salt form. For example, in some embodiments, the tertiary amino lipidated and/or PEGylated cationic peptide compound is a salt form thereof. In certain embodiments, the salt form is an acid addition salt. In some embodiments, the salt of the tertiary amino lipidated and/or PEGylated cationic peptide compound is a hydrochloride salt (hydrochloric acid addition salt), a hydrobromide salt (hydrobromic acid addition salt, or a trifluoroacetate salt (trifluoroacetic acid addition salt). In certain embodiments, the salt of the tertiary amino lipidated and/or PEGylated cationic peptide compound is a trifluoroacetic acid addition salt, or trifluoroacetate salt, of the tertiary amino lipidated and/or PEGylated cationic peptide compound.

The acid addition salt form of the tertiary amino lipidated and/or PEGylated cationic peptide compound may be further modified via methods in the art (e.g., ion exchange) in order to obtain one or more pharmaceutically acceptable salt forms. The phrase "pharmaceutically acceptable" indicates that the substance or composition must be compatible chemically and/or toxicologically, with the other ingredients comprising a formulation, and/or the subject to which/whom the formulation is being administered. The term "pharmaceutically acceptable acid addition salt" may include but is not limited to those pharmaceutically acceptable salts formed with inorganic acids such as hydrochloric acid, hydrobromic acid, hydroiodic acid, sulfuric acid, nitric acid, carbonic acid, phosphoric acid, and organic acids selected from aliphatic, cycloaliphatic, aromatic, aryl-aliphatic, heterocyclic, carboxylic, and sulfonic classes of organic acids such as formic acid, acetic acid, propionic acid, gluconic acid, lactic acid, pyruvic acid, oxalic acid, maleic acid, malonic acid, succinic acid, fumaric acid, tartaric acid, citric acid, aspartic acid, ascorbic acid, glutamic acid, benzoic acid, phenylacetic acid, methanesulfonic acid "mesylate", ethanesulfonic acid, p-toluenesulfonic acid, and salicyclic acid.

In some embodiments, the salt of the tertiary amino lipidated and/or PEGylated cationic peptide compound is a pharmaceutically acceptable salt. In certain embodiments, the salt is a hydrochloride salt, hydrobromide salt, hydroiodide salt, nitrate salt, sulfate salt, bisulfate salt, phosphate salt, acid phosphate salt, formate salt, acetate salt, propionate salt, gluconate salt, lactate salt, pyruvate salt, oxalate salt, maleate salt, malonate salt, succinate salt, fumarate salt, tartrate salt, bitartrate salt, citrate salt, aspartate salt, ascorbate salt, glutamate salt, benzoate salt, methanesulfonate salt, ethanesulfonate, p-toluenesulfonate salt, or salicylate salt.

Lipitoids

In some embodiments, the one or more lipidated cationic peptide compounds of the complexes and compositions described herein comprises one or more cationic peptoid-phospholipid conjugate constructs, also known as lipitoids. Lipitoids are N-substituted polyglycine compounds (also known as "peptoids") having a combination of cationic and/or neutral side chains at the N-positions of glycine residues along peptoid backbone, which are further conjugated to a single terminal phospholipid group of the peptoid chain. Lipitoids and their synthesis are generally described in Simon R. J. et al., Proc. Natl. Acad. Sci. U.S.A. 89, 9367-9371 (1992); Lobo, B. A.; Vetro, J. A.; Suich, D. M.; Zuckermann, R. N.; Middaugh, C. R. Structure/Function Analysis of Peptoid/Lipitoid:DNA Complexes. *Journal of Pharmaceutical Sciences* 2003, 92 (9), 1905-1918; and Utku, Y.; Dehan, E.; Ouerfelli, O.; Piano, F.; Zuckermann, R. N.; Pagano, M.; Kirshenbaum, K. A Peptidomimetic SiRNA Transfection Reagent for Highly Effective Gene Silencing. *Molecular BioSystems* 2006, 2 (6-7), 312. An exemplary lipitoid is the nonamer "Lipitoid 1" as shown in FIG. 1. The general structure of a lipitoid compound is shown in formula (II) below, wherein x is an integer from 1 to 100, each $R^9$ is independently a lipid moiety and each $R^{10}$ is independently a cationic or neutral moiety.

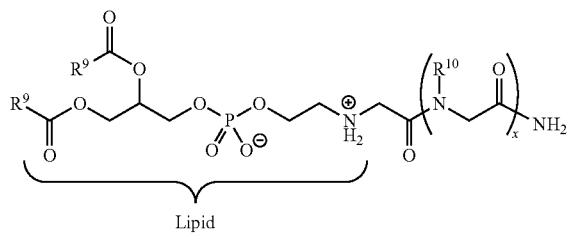

(II)

In formula (II) above, x is an integer from 1 to 100. Particular numbers of residues may be especially suitable for use in the complexes and compositions described herein. For example, in some embodiments, x is an integer from 1 to 50, from 2 to 25, or from 3 to 15.

As shown in Formula (II) above, $R^9$ represent lipid moieties, including but not limited to include branched or straight chain aliphatic moieties having from about 6 to about 50 carbon atoms or from about 10 to about 50 carbon atoms, optionally comprising one or more heteroatoms, and optionally comprising one or more double or triple bonds (i.e., saturated or mono- or poly-unsaturated). In certain embodiments, the lipid moieties $R^9$ may include optionally substituted aliphatic, straight chain or branched moieties, each hydrophobic tail independently having from about 8 to about 30 carbon atoms or from about 6 to about 30 carbon atoms. In certain embodiments, the lipid moieties may include, for example, aliphatic carbon chains derived from fatty acids and fatty alcohols. In some embodiments, each lipid moiety $R^9$ is independently $C_8$-$C_{24}$-alkyl or $C_8$-$C_{24}$-alkenyl, wherein the $C_8$-$C_{24}$-alkenyl is optionally mono- or poly-unsaturated. In other embodiments, each lipid moiety $R^9$ is independently selected from the group consisting of oleyl, stearyl, linoleyl, myristyl, and lauryl. In yet other embodiments which may be combined with any of the preceding embodiments, each lipid moiety $R^9$ is independently

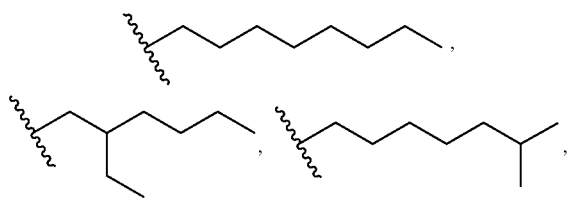

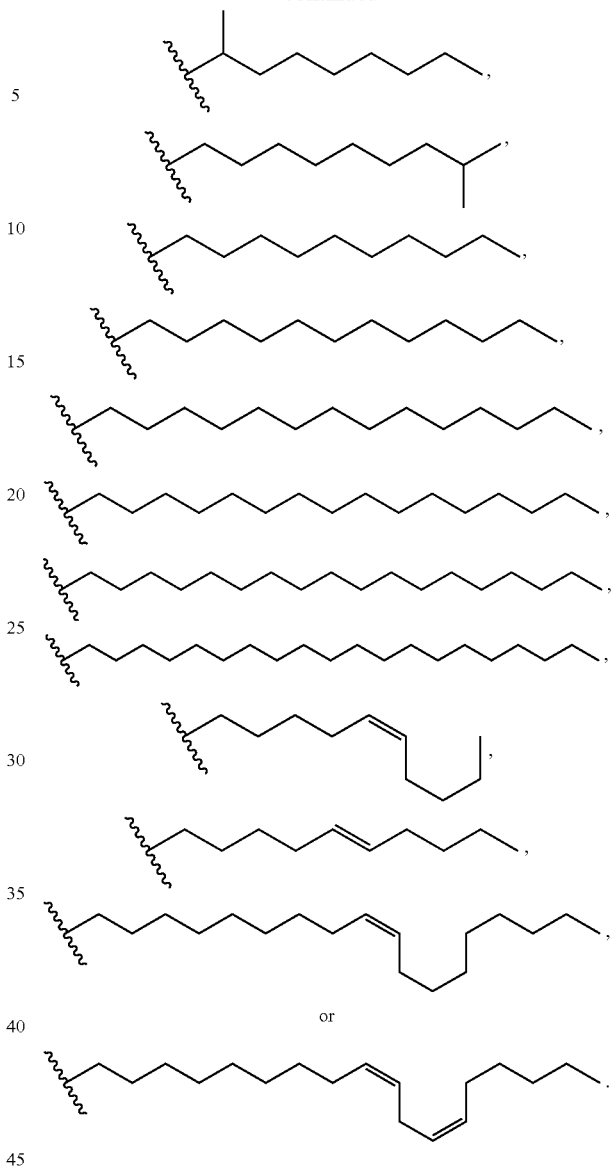

The group(s) $R^{10}$ at the N-position of the amino glycine residue includes cationic and neutral moieties similar to those described above for the tertiary amino lipidated and/or PEGylated cationic peptide compounds.

Cationic, or positively charged, moieties may include, for example, nitrogen-based substituents, such as those containing the following functional groups: amino, guanidino, hydrazido, and amidino. These functional groups can be either aromatic, saturated cyclic, or aliphatic. In some embodiments of the lipitoid, each cationic moiety is independently aminoalkyl, alkylaminoalkyl, aminoalkylaminoalkyl, guanidinoalkyl, or N-heterocyclylalkyl. In other embodiments, each cationic moiety is independently

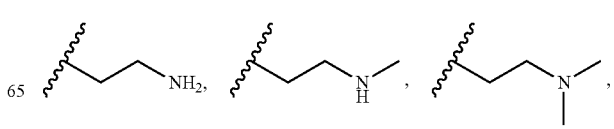

-continued

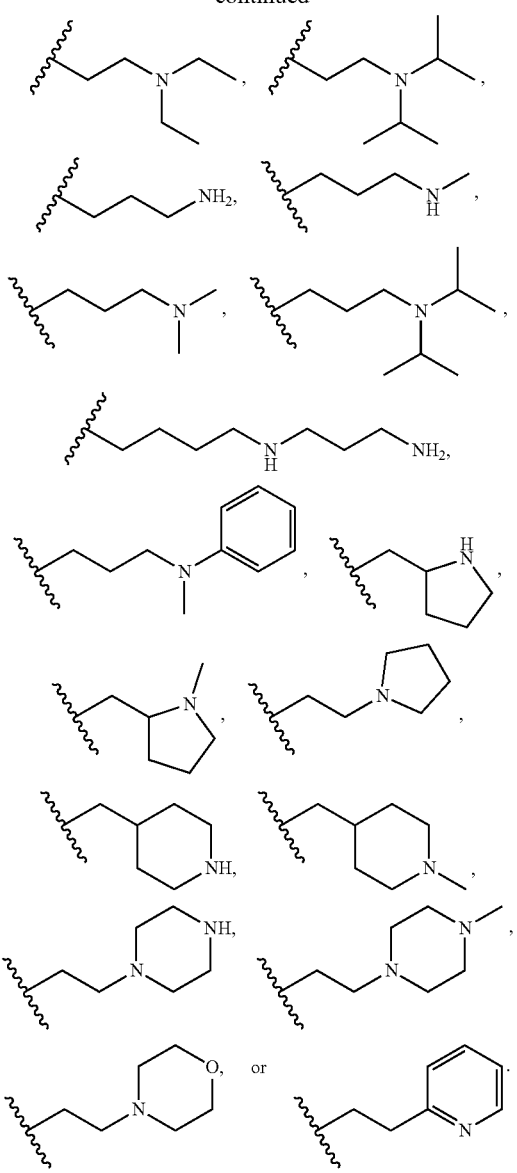

In certain embodiments, each cationic moiety is independently selected from the group consisting of:

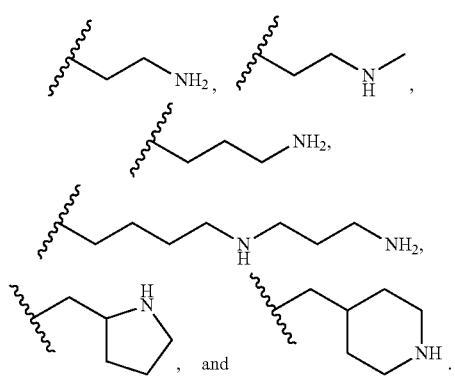

In still other embodiments, each cationic moiety is

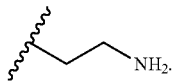

Neutral moieties may include but are not limited to a $C_1$-$C_4$-alkyl substituted by cycloalkyl, heterocyclylalkyl, alkylaryl, arylalkyl, alkylheteroaryl, heteroarylalkyl, alkoxy, alkoxyalkyl, or hydroxyalkyl, wherein each cycloalkyl, heterocyclylalkyl, alkylaryl, arylalkyl, alkylheteroaryl, heteroarylalkyl, alkoxy, alkoxyalkyl, or hydroxyalkyl is optionally substituted with one or more substituents —OH, halo, or alkoxy. In some embodiments of the lipitoid, each neutral moiety is independently selected from the group consisting of:

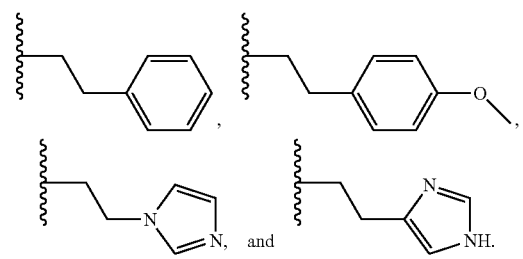

In certain embodiments, each neutral spacer moiety is

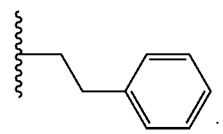

In still other embodiments, each neutral spacer moiety is

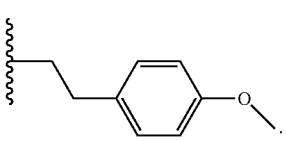 [SMILES: *CCc1ccc(OC)cc1]

In still other embodiments, each cationic moiety is

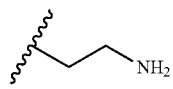

and each neutral spacer moiety is

In yet further embodiments, the one or more lipitoids comprise Lipitoid 1.

Similar to the tertiary amino lipidated and/or PEGylated cationic peptide compounds above, the lipitoids described herein may include the amino acid residues arranged in random sequences, or repeating motifs in alternating sequences or block sequences. In some embodiments, the lipitoid of formula (II) may comprise repeating (dimer, trimer, tetramer, etc.) subunits within the chain of x residues. These subunits may include but are not limited to —$R^{cation}R^{neutral}$— or —$R^{cation}R^{neutral}R^{neutral}$—, wherein $R^{cation}$ is an amino acid residue comprising a cationic moiety and each $R^{neutral}$ is an amino acid residue comprising a neutral spacer moiety. In other embodiments, the lipitoid of formula (II) comprises at least one trimer subunit —$R^{cation}$—$R^{neutral}$—$R^{neutral}$, and wherein $R^{cation}$ is an amino acid residue comprising a cationic moiety and each $R^{neutral}$ is an amino acid residue comprising a neutral spacer moiety.

In some embodiments wherein the lipitoid of formula (II) comprises a cationic domain, each cationic moiety $R^{10}$ is

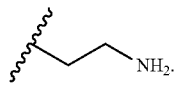

In other embodiments of the foregoing embodiments, each cationic moiety $R^{10}$ is

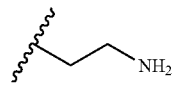

and each neutral spacer moiety $R^{10}$ is

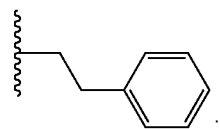

In certain embodiments, the lipitoid of formula (II) comprises one or more dimer or trimer subunits, wherein each cationic moiety is

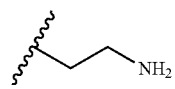

and each neutral spacer moiety is

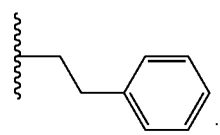

In still other embodiments, the lipitoid of formula (II) comprises a cationic domain comprising one or more trifler subunits —$R^{cation}R^{neutral}R^{neutral}$—, wherein $R^{cation}$ is an amino acid residue comprising a cationic moiety and each $R^{neutral}$ is an amino acid residue comprising a neutral spacer moiety, wherein each cationic moiety is

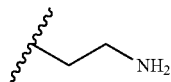

and wherein each neutral spacer moiety is

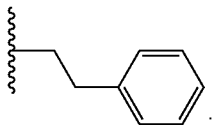 [SMILES: *CCc1ccccc1]

As with the tertiary amino lipidated and/or PEGylated cationic peptide compounds, the complexes and compositions described herein may comprise one or more lipitoids. In certain embodiments, the one or more cationic compounds comprises one or more lipitoids. In still other embodiments, the one or more cationic compounds comprises Lipitoid 1.

Other Lipid Components

In addition to the lipidated cationic peptide compounds employed as the primary lipid components for charge neutralization of the one or more polyanionic compounds as cargo, the multicomponent lipid compositions and complexes therein may comprise other lipid components including structural lipids, phospholipids and shielding lipids. The additional lipid components described herein provide physical structure and stability to the complex of the cationic peptide compounds and polyanionic material that facilitate their administration in solution and promote the uptake of the complexes into the cell.

Structural Lipids

Structural lipids may be used as described herein to confer physical stability to the complexes of the polyanionic compounds within the multicomponent compositions, and enhance lipophilic character of the complexes to promote binding and endocytosis with the target cells. In some embodiments, the compositions of the present disclosure comprise complexes comprising optionally one or more structural lipids as lipid components. In some variations, the compositions comprise complexes comprising one or more structural lipids.

Suitable structural lipids for the compositions and complexes of the present disclosure may include but are not limited to sterols. In some embodiments, the structural lipid is selected from the group consisting of cholesterol, fecosterol, sitosterol, ergosterol, campesterol, stigmasterol, brassicasterol, tomatidine, ursolic acid, alpha-tocopherol, and mixtures thereof. In certain embodiments, the structural lipid is cholesterol.

It should be noted, however, that in some embodiments of the present disclosure the compositions and complexes provided herein do not contain structural lipids, but still exhibit very good delivery efficiency. In certain other embodiments, the compositions and complexes provided herein do not contain structural lipids.

(Zwitterionic) Phospholipids or Zwitterionic Lipids

Phospholipids, as with structural lipids described above, may also be incorporated into the complexes and compositions of the present disclosure. Phospholipids provide further stabilization to complexes in solution as well as facilitate cell endocytosis, by virtue of their amphipathic character and ability to disrupt the cell membrane. In some embodiments, the compositions provided herein comprises complexes comprising one or more phospholipids as lipid components. In certain embodiments, the one or more phospholipids comprise one or more zwitterionic phospholipids.

In some embodiments, the one or more phospholipids are selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C 16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-dipalmitoyl-sn-glycero-3-phosphoethanolamine (DPPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof. In certain embodiments, the phospholipid is DOPE.

It should be recognized that the amphipathic attributes provided by the phospholipids to facilitate the disruption of the cellular membrane for endocytosis may be alternatively provided by zwitterionic lipids that are not phospholipids. In some embodiments, the compositions comprise complexes comprising one or more zwitterionic lipids that are not phospholipids. In still further embodiments, the comprises comprise complexes comprising one or more phospholipids, one or more zwitterionic lipids, or any combinations thereof.

Shielding Lipids

As described herein, the complexes and compositions of the present disclosure may further include one or more shielding lipids. Shielding lipids, such as PEGylated lipids, may provide an additional layer of charge neutralization to the one or more lipidated cationic peptide compounds as counter charge to the one or more polyanionic compounds and prevent clearance by the cellular phagocytic processes. In some embodiments, the compositions provided herein comprises complexes comprising one or more shielding lipids as lipid components.

In some embodiments, the shielding lipid is a PEG lipid. In other embodiments, the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG lipid is a PEG-modified phosphatidylethanol selected from the group consisting of PEG-modified DSPE (DSPE-PEG), PEG-modified DPPE (DPPE-PEG), and PEG-modified DOPE (DOPE-PEG). In certain embodiments, the PEG lipid is selected from the group consisting of dimyristoylglycerol-polyethylene glycol (DMG-PEG), distearoylglycerol-polyethylene glycol (DSG-PEG), dipalmitoylglycerol-polyethylene glycol (DPG-PEG), and dioleoylglycerol-polyethylene glycol (DOG-PEG). In certain embodiments, the PEG lipid is DMG-PEG.

It should be further recognized that particular molecular weights of the PEG chain in the foregoing PEG lipids may be especially advantageous for incorporation into the complexes of the present disclosure. For example, in some embodiments, the PEG chain has a molecular weight between 350 and 6,000 g/mol, between 1,000 and 5,000 g/mol, or between 2,000 and 5,000 g/mol. In certain embodiments, the PEG chain of the PEG lipid has a molecular weight of about 350 g/mol, 500 g/mol, 600 g/mol, 750 g/mol, 1,000 g/mol, 2,000 g/mol, 3,000 g/mol, 5,000 g/mol, or 10,000 g/mol. In certain other embodiments, the PEG chain of the PEG lipid has a molecular weight of about 500 g/mol, 750 g/mol, 1,000 g/mol, 2,000 g/mol or 5,000 g/rmol. For example, in certain embodiments, the PEGylated lipid is dimyristoylglycerol-polyethylene glycol 2000 (DMG-PEG 2000).

In still further embodiments, the one or more PEG lipids comprise a tertiary amino PEGylated cationic peptide compounds of formula (I) comprising at least one oligo- or polyethylene glycol moiety. By virtue of their flexibility in accommodating both lipid and PEG moieties along the backbone of the peptide chain and depending upon the nature of their specific substituents, the tertiary amino lipidated and/or PEGylated cationic peptide compounds of formula (I) of the present disclosure may serve not only as the lipidated cationic peptide compounds but also as suitable shielding lipids to stabilize the cationic compound-polyanionic compound complex. It should be recognized that tertiary amino PEGylated cationic peptide compounds of formula (I) may be combined with other classes of cationic compounds such as lipitoids or lipid-like compounds as well as other tertiary amino lipidated and/or PEGylated cationic peptide compounds of formula (I).

In some embodiments, the PEGy lipid is a tertiary amino lipidated and/or PEGylated cationic peptide compound of formula (I) as described herein, wherein at least one of m and t is nonzero (i.e., N-PEGylated). In still further embodiments, the PEG lipid is a tertiary amino lipidated and/or PEGylated cationic peptide compound of formula (I) wherein mm and t are independently an integer from 0 to 10, and wherein at least one of m and t is nonzero. In some embodiments, the PEG lipid is a tertiary amino PEGylated cationic peptide compound of formula (Ib). In yet other embodiments, the PEG lipid is a tertiary amino lipidated and PEGylated cationic compound of formula (Ic).

As with the PEG lipids described above, particular molecular weights of the PEG chain in the foregoing tertiary amino lipidated and PEGylated cationic peptide compounds may be especially advantageous for incorporation into the complexes of the present disclosure. For example, in some embodiments, the PEG chain has a molecular weight between 350 and 6,000 g/mol, between 1,000 and 5,000 g/mol, or between 2,000 and 5,000 g/mol. In certain embodiments, the PEG chain of the tertiary amino lipidated and PEGylated cationic peptide compound has a molecular weight of about 350 g/mol, 500 g/mol, 600 g/mol, 750 g/mol, 1,000 g/mol, 2,000 g/mol, 3,000 g/mol, or 5,000 g/mol. In certain other embodiments, the PEG chain of the PEG lipid has a molecular weight of about 500 g/mol, 750 g/mol, 1,000 g/mol, 2,000 g/mol or 5,000 g/rmol.

However, it should be recognized that the tertiary amino lipidated and/or PEGylated cationic peptide compounds of formula (I) may comprise several short oligoethylene glycol moieties in lieu of fewer longer polyethylene glycol moieties and provide similar particle stabilization to the complex. In some embodiments wherein the PEGylated compound is an N-PEGylated cationic peptide compound of formula (I), tertiary amino lipidated and/or PEGylated cationic peptide compound comprises at least one ethylene glycol moiety $R^2$ of the formula —$CH_2CH_2O(CH_2CH_2O)_uR^{2a}$, wherein each $R^{2a}$ is independently —H or $C_1$-$C_4$-alkyl. In other embodiments, at least one ethylene glycol moiety $R^6$ of the formula —$CH_2CH_2O(CH_2CH_2O)_vR^{6a}$, wherein each $R^{6a}$ is independently —H or $C_1$-$C_4$-alkyl. In some embodiments which may be combined with any of the preceding embodiments wherein m is nonzero, m is an integer from 0 to 10, wherein each u is independently an integer from 2 to 200. In still further embodiments which may be combined with any of the preceding embodiments wherein t is nonzero, t is an integer from 0 to 10, wherein each v is independently an integer from 2 to 200.

In some embodiments, the PEG lipid is a tertiary amino lipidated and/or PEGylated cationic peptide compound of formula (I) as described herein, wherein at least one of m and t is nonzero and at least one of n and s is nonzero (i.e., N-lipidated). In certain embodiments wherein the N-PEGylated cationic peptide compound of formula (I) is also N-lipidated, at least one of n and s is nonzero. In some embodiments, the sum of n and s is at least 1, 2, 3, or 4. In certain embodiments, s is 4. In yet further embodiments, n is 4.

Polyanionic Compounds

As described herein multicomponent lipid compositions comprising lipidated cationic peptide compounds of the present disclosure may be useful for complexation with one or more polyanionic compounds, such as nucleic acids. In one aspect, the present disclosure provides compositions comprising complexes comprising one or more polyanionic compounds as described herein complexed to one or more lipidated cationic peptide compounds and two or more other lipid components.

In some embodiments, the one or more polyanionic compounds comprises a nucleic acid. Nucleic acids, as used herein, include naturally occurring nucleic acids such as DNA, RNA, and/or hybrids thereof as well as unnaturally occurring variations with unnatural backbone and modified backbone linkages such as phosphorothioate, unnatural and modified bases, and unnatural and modified termini. Exemplary nucleic acids include genomic DNA, cDNA, mRNA, miRNA, and siRNA.

The nucleic acids may be recombinantly produced or chemically synthesized molecules. A nucleic acid may be single-stranded, double-stranded, triple stranded, and quadruple stranded as well as in more complicated three-dimensional forms including single and double stranded regions.

Depending upon the type of nucleic acid, the length of the nucleic acid (defined in nucleotide units or base pairs (bp) as appropriate) may vary. In some embodiments wherein the nucleic acid is mRNA, the mRNA may have from 100 to 10,000 nucleotide units, or from 1,000 to 3,000 nucleotide units. In other embodiments wherein the nucleic acid is DNA, the DNA may have from 5,000 bp to 20,000 bp, or about 10,000 bp.

In some embodiments wherein the nucleic acid is an mRNA, the mRNA is an mRNA encoding a protein or a peptide. In some embodiments wherein the nucleic acid is an mRNA, the mRNA is an mRNA encoding a peptide, including an oligopeptide or a polypeptide. In certain embodiments, the mRNA is an mRNA encoding a polypeptide. In yet further embodiments, the mRNA is an mRNA encoding a protein. In other embodiments, the mRNA is an mRNA encoding a peptide. As described above, the mRNA may be naturally-occurring (e.g., isolated tumor RNA) or may be synthetic (e.g., produced by in vitro transcription). For synthetic or unnaturally occurring variations of mRNA, the mRNA may comprise an unnatural backbone with modified backbone linkages such as phosphorothioate, unnatural and modified bases, and/or unnatural and modified termini. In certain embodiments wherein the nucleic acid is an mRNA, the mRNA may comprise special sequences such as self-amplifying sequences or internal ribosome entry sites.

In some embodiments, the combined delivery of two or more particular nucleic acids together may be especially useful for therapeutic applications. For example, in some embodiments, the one or more polyanionic compounds includes a combination of sgRNA (single guide RNA) as a CRISPR sequence and mRNA encoding Cas9. In still further embodiments, the nucleic acids may also be complexed with proteins such as with the CRISPR/Cas9 ribonucleoprotein complex.

In some embodiments, the one or more polyanionic compounds may include anionic or polyanionic compounds that are not nucleic acids. Suitable anionic compounds may include hut are not limited to proteins, polyphosphates, or heparins. In some embodiments, the one or more polyanionic compounds comprises one or more proteins. In one embodiments, the one or more polyanionic compounds comprises Cas9 protein. In other embodiments, the one or more polyanionic compounds comprises polyphosphates. In yet other embodiments, the one or more polyanionic compounds comprises heparins or other glycosaminoglycan derivatives.

The multicomponent lipid formulations comprising lipidated cationic peptide compounds with other lipid components described herein may also be utilized to form complexes with other non-anionic agents or cargoes (including hydrophobic compounds) for delivery into cells. These other cargoes may include but are not limited to, for example, one or more small molecule active agents or drug substance (as a standalone therapeutic or in combination with another agent, such as a nucleic acid) and/or immunological adjuvants. It should be further recognized that these other cargo molecules may or may not be combined with any of the polyanionic compounds described herein for complexation. In some embodiments, the complexes described herein comprise endosomal escape modulators, TLR agonists, and chemotherapeutics. In other embodiments, the complexes of the present disclosure comprise adjuvants or immune co-stimulators. For example, in some embodiments, the complex comprises immunological adjuvants selected from the group consisting of CpG oligodeoxynucleotides (ODNs), lipopolysaccharides (LPS), and any combinations thereof.

Properties of the Complexes and Composition

As described above, the compositions of the present disclosure comprise complexes comprising one or more polyanionic compounds, and lipid components, wherein the lipid components comprise one or more lipidated cationic peptide compounds, one or more phospholipids, one or more shielding lipids, and optionally one or more structural lipids. The physical properties of the complexes and compositions described herein may be influenced by the particular selection of lipid components for a given polyanionic compound as well as by the quantities of each component within the complexes and compositions. In some embodiments, the lipid components within the complexes and compositions thereof may be characterized by the mass percentages of the lipid components (alone or in combination) with respect to mass of the total lipid components present and/or mass ratios of individual lipid components with respect to one another.

In some embodiments, the compositions of the present disclosure are characterized by the mass percentages of the lipid components present. As described herein, the total mass or weight of the lipid components is the sum of the individual masses of any lipidated cationic peptide compounds, any structural lipids, any phospholipids, and any shielding lipids present.

In some embodiments, the compositions as described herein comprise complexes comprising one or more lipidated cationic peptide compounds. In some variations of the foregoing, the compositions and complexes therein comprise 40-80% w/w one or more lipidated cationic peptide compounds of the total weight of the lipid components. In certain variations, compositions and complexes therein comprise 40-70% w/w one or more lipidated cationic peptide compounds of the total weight of the lipid components. In other variations of the foregoing, the compositions and complexes therein comprise 40-80% w/w one or more tertiary amino lipidated and/or PEGylated cationic peptide compounds of formula (I) or salts thereof of the total weight of the lipid components. In certain variations, the compositions and complexes therein comprise 40-70% w/w one or more tertiary amino lipidated and/or PEGylated cationic peptide compounds of formula (I) or salts thereof of the total weight of the lipid components. In still other variations of the foregoing, the compositions and complexes therein comprise 40-80% w/w one or more lipitoids of formula (II) of the total weight of the lipid components. In certain variations, the compositions and complexes therein comprise 40-70% w/w one or more lipitoids of formula (II) of the total weight of the lipid components.

As described herein, the compositions comprising complexes may optionally include one or more structural lipids. In some embodiments which may be combined with any of the foregoing embodiments, the compositions and complexes therein comprise 0-25% w/w one or more structural lipids of the total weight of the lipid components. In certain variations, the compositions and complexes therein comprise 0-25% w/w cholesterol of the total weight of the lipid components.

The compositions and complexes as described herein also comprise one or more phospholipids. In still other embodiments, the compositions and complexes therein comprise 10-60% w/w one or more phospholipids of the total weight of the lipid components. In certain variations, the compositions and complexes therein comprises 20-40% w/w one or more phospholipids of the total weight of the lipid components. In some embodiments, the compositions and complexes therein comprise 10-60% w/w 1,2-dioleoyl-sn-glycero-3-phosphoethanolamine (DOPE) of the total weight of the lipid components. In certain embodiments, the compositions and complexes therein comprise 20-40% w/w 1,2-dioleoyl-sn-glycero-3-phosphoethanolamine (DOPE) of the total weight of the lipid components.

In further embodiments, the compositions and complexes therein comprise one or more shielding lipids. In some embodiments, the compositions and complexes therein comprise 1-5% one or more shielding lipids of the total weight of the lipid components. In certain embodiments, the compositions and complexes therein comprise 1-5% one or more PEG lipids of the total weight of the lipid components. In still other embodiments, the compositions and complexes therein comprise 1-5% 1,2-dimyristoyl-rac-glycero-3-methoxypolyethylene glycol (DMG-PEG) of the total weight of the lipid components.

In still other embodiments, the compositions and complexes therein of the present disclosure comprise 40-80% w/w one or more lipidated cationic peptide compounds; 0-25% w/w one or more structural lipids; 10-60% w/w phospholipids; and 1-5% one or more shielding lipids of the total weight of the lipid components. In yet further embodiments, the compositions and complexes therein of the present disclosure comprise 40-70% w/w one or more lipidated cationic peptide compounds; 0-25% w/w one or more structural lipids; 20-40% w/w phospholipids; and 1-5% one or more shielding lipids of the total weight of the lipid components.

In other embodiments, the compositions and complexes therein of the present disclosure comprise 40-80% w/w one or more tertiary amino lipidated and/or PEGylated cationic peptide compounds of formula (1) or salts thereof; 0-25% w/w cholesterol; 10-60% w/w DOPE; and 1-5% DMG-PEG2000 of the total weight of the lipid components. In yet further embodiments, the compositions and complexes therein of the present disclosure comprise 40-70% w/w one or more tertiary amino lipidated and/or PEGylated cationic peptide compounds of formula (I) or salts thereof; 0-25% w/w cholesterol; 20-40% w/w DOPE; and 1-5% DMG-PEG2000 of the total weight of the lipid components.

In yet other embodiments, the compositions and complexes therein of the present disclosure comprise 40-80% w/w one or more lipitoids of formula (II); 0-25% w/w cholesterol; 10-60% w/w DOPE; and 1-5% DMG-PEG2000 of the total weight of the lipid components. In yet further embodiments, the compositions and complexes therein of the present disclosure comprise 40-70% w/w one or more lipitoids of formula (II); 0-25% w/w cholesterol; 20-40% w/w DOPE; and 1-5% DMG-PEG2000 of the total weight of the lipid components.

In some embodiments wherein the complex comprises a lipidated cationic peptide compound, a nucleic acid, a phospholipid, a PEG lipid, and optionally also a structural lipid, the complex may be characterized by the mass ratio of the individual components to each other, or a mass ratio of one or more components to the one or more other components. For example, in some embodiments, the compositions and complexes of the present disclosure may be described by a first mass ratio of the lipidated cationic peptide compound to the phospholipid to the structural lipid (if present) to the shielding lipid and a second mass ratio of the lipidated cationic peptide compound to nucleic acid. Alternatively, in other embodiments, the compositions and complexes provided herein may be described by a mass ratio of the total lipid components to nucleic acid, wherein the total lipid components include any lipidated cationic peptide compounds, structural lipids, phospholipids, and shielding lipids present.

In another aspect, the complexes and compositions of the present disclosure can be characterized by mass ratios of individual components to one another. For example, as described herein, the complexes of the present disclosure comprise one or more phospholipids and optionally one or more structural lipids. In some embodiments wherein the composition comprises complexes comprising one or more structural lipids and one or more phospholipids, the composition can be characterized by the mass ratio of the one or more structural lipids to the one or more phospholipids. In some embodiments, the mass ratio of the one or more structural lipids, when present, to the one or more phospholipids in between 0.5:1 and 2:1. In certain embodiments wherein the composition comprises cholesterol and DOPE, the mass ratio of cholesterol to DOPE is between 0.5:1 and 2:1.

With regard to the polyanionic compounds present in the complexes and compositions of the present disclosure, the quantity of polyanionic compounds within the complexes, and therefore also the compositions, may be characterized in a number of ways. In some embodiments, the compositions and complexes described herein may be characterized by the ratio of the number cationic groups on the lipidated cationic peptide compounds to the number of anionic phosphate groups on the nucleic acid. In some embodiments, the complex comprises the lipidated cationic peptide compound and the nucleic acid at a cation: anion charge ratio of between 0.5:1 and 20:1, between 0.5:1 and 10:1, between 0.5:1 and 5:1, between 1:1 and 20:1, between 1:1 and 10:1, between 1:1 and 5:1, between 2:1 and 20:1, between 2:1 and 10:1, or between 2:1 and 5:1. In certain embodiments, the complex comprises the lipidated cationic peptide compound and the nucleic acid at a cation: anion charge ratio of between 2:1 and 5:1. In still yet other embodiments, the complex comprises the lipidated cationic peptide compound and the nucleic acid at a cation: anion charge ratio of 3:1.

Alternatively, the complexes and compositions comprising the complexes described herein may be characterized by the relative mass ratio of the lipidated cationic peptide compound(s) to the polyanionic compound(s) and/or other cargoes in the complex. Mass ratios of the components in the complex can be readily calculated based upon the known concentrations and volumes of stock solutions of each component used in preparing the complex. Moreover, if non-anionic cargoes are present in the complex, mass ratios may provide a more accurate representation of the relative amounts of lipidated cationic peptide compound to the overall cargo than cation:anion charge ratios, which do not account for non-anionic material.

In some embodiments, the complex comprises the one or more lipidated cationic peptide compounds and one or more polyanionic compounds and/or non-anionic compounds at a mass ratio of between 0.5:1 and 20:1, between 0.5:1 and 10:1, between 0.5:1 and 5:1, between 1:1 and 20:1, between 1:1 and 10:1, between 1:1 and 5:1, between 2:1 and 20:1, between 2:1 and 10:1, or between 2:1 and 5:1. In certain embodiments, the complex comprises the one or more lipidated cationic peptide compounds and the one or more polyanionic compounds and/or non-anionic compounds at a mass ratio of between 2:1 and 5:1. In still yet other embodiments, the complex comprises the one or more lipidated cationic peptide compounds and the one or more polyanionic compounds and/or non-anionic compounds at a mass ratio of 3:1.

In certain embodiments wherein the complex comprises a nucleic acid, the complex comprises the lipidated cationic peptide compound and the nucleic acid at a mass ratio of between 0.5:1 and 20:1, between 0.5:1 and 10:1, between 0.5:1 and 5:1, between 1:1 and 20:1, between 1:1 and 10:1, between 1:1 and 5:1, between 2:1 and 20:1, between 2:1 and 10:1, or between 2:1 and 5:1. In certain embodiments, the complex comprises the lipidated cationic peptide compound and the nucleic acid at a mass ratio of between 2:1 and 5:1. In still yet other embodiments, the complex comprises the lipidated cationic peptide compound and the nucleic acid at a mass ratio of 3:1.

In still other embodiments, the amount of polyanionic compounds present in the complexes and compositions thereof may be characterized by a mass ratio of the lipid components (lipidated cationic peptide compound, phospholipid, shielding lipid, and structural lipid if present) to the one or more polyanionic compounds. In some embodiments, the mass ratio of the lipid components to the one or more polyanionic compounds is between 0.5:1 and 20:1, between 0.5:1 and 10:1, between 0.5:1 and 5:1, between 1:1 and 20:1, between 1:1 and 10:1, between 1:1 and 5:1, between 2:1 and 25:1, between 2:1 and 20:1, between 2:1 and 10:1, or between 2:1 and 5:1. In certain embodiments, the mass ratio of the lipid components to the one or more polyanionic compounds is between 5:1 and 10:1 or between 6:1 and 7:1.

The complexes of the present disclosure will comprise at least one lipidated cationic peptide compound complexed with at least one polyanionic compound or other suitable cargo compound. In some embodiments, the complexes described herein may comprise one or more tertiary amino lipidated and/or PEGylated cationic peptide compounds of formula (I). In other embodiments, the complexes provided herein comprises one or more lipitoids of formula (II). The use of mixtures and combinations of multiple lipidated cationic peptide compounds of the present disclosure in a single complex may enable the preparation of formulations tailored for specific pharmacokinetic and pharmacodynamics properties. Pharmacokinetic and pharmacodynamics properties of relevance may include but are not limited to biodistribution, immunogenicity, formulation stability, encapsulation percentage, transfection efficiency, plasma half-life, etc. Different combinations of these properties may be required for different applications.

For example, in certain embodiments, the complex may comprise a combination of one or more tertiary amino lipidated and/or PEGylated cationic peptide compounds which are cation-rich with one or more tertiary amino lipidated and/or PEGylated cationic peptide compounds which are highly lipidated. In theory, such a combination could confer improved delivery of polyanionic compounds by providing greater charge stabilization (via the cation-rich peptide compounds) along with greater lipophilic shielding (by virtue of the lipidated peptide compounds). It should further be recognized that the individual amounts of each of the individual lipidated cationic peptide compounds may be adjusted to achieve the desired properties.

Additional Components

Additional components may also be added to the complexes to facilitate high encapsulation of polyanionic cargoes and/or targeted, controlled release thereof. Such additional components may include, for example, polymers and surface-active components.

As provided in the present disclosure, the complexes may include further components useful for delivery of nucleic acid cargoes and other compounds to cells. Such components may include but are not limited to those which together form, for example, supercomplexes or other delivery systems (e.g., hybrid lipid-polymer nanoparticles) comparable to lipid nanoparticles.

The incorporation of polymers into the complexes described herein may stabilize the complexes comprising the lipidated cationic peptide compounds and polyanionic compounds by forming polymeric nanoparticle vesicles, or in the presence of additional lipid components, hybrid lipid-polymer nanoparticles. In some embodiments, the complexes of the present disclosure comprise polymers. Suitable polymers may include neutral polymers (such as poly(lactic-co-glycolic acid) (PLGA) or polyglycolic acid (PGA)), anionic polymers (including poly(aspartate), poly(glutamate), and heparin), and/or cationic polymers (e.g., polyethyleneimine, protamine).

In other embodiments, the complexes and compositions described herein comprise surface-active components, such as targeting ligands, stabilizing agents, and/or surfactants.

In another aspect, the present disclosure provides for formulations comprising the compositions comprising complexes as described herein. The formulations as described herein encompass mixtures of stock solutions used to prepare the complexes herein as well as purified pharmaceutical formulations to be used for administration. It should be understood that the formulations comprising the complexes of the present disclosure will necessarily also comprise the components present in the complexes as described herein.

In some embodiments, the formulation is a solution, a suspension, a colloidal suspension, a spray, or an aerosol. In other embodiments, the formulation is a lipid complex formulation. In some embodiments, the formulation is an enteral formulation, a parenteral formulation or a topical formulation. In some embodiments, the formulation is an injectable formulation, such as an intravenous formulation, a subcutaneous formulation, an intramuscular formulation, an intradermal formulation, an intraocular formulation, or an intrathecal formulation. In other embodiments, the formulation is an oral formulation. In still other embodiments, the formulation is a mucosal formulation, including for example a nasal formulation, an intra-anal formulation, a buccal formulation, or an intravaginal formulation, etc.

As described above for the complexes and compositions of the present disclosure, the compositions provided herein may comprise one or more lipidated cationic peptide compounds, one or more phospholipids, one or more shielding lipids, and optionally one or more structurally lipids with one or more polyanionic compounds and/or non-anionic compounds. In addition to the lipidated cationic peptides, other lipid components and the one or more polyanionic compounds and/or non-anionic compounds, it should be recognized that still further components may be included in the formulations to adjust their pharmacokinetic and pharmacodynamic properties.

It should be further recognized that the components used in preparing the complexes and formulations of the present disclosure, as well as the process parameters for making said complexes or formulations, may be adapted depending upon whether the complexes and/or formulations are intended for immediate use ("just-in-time") or will be placed in storage for future use. In particular, considerations for storage may include the temperature at which the complexes and/or formulations are kept (e.g., at room temperature, at 4° C., at −20° C., at −78° C.) and the duration of storage.

Suitable excipients may include but are not limited to those which facilitate administration or improve storage stability (e.g., cryoprotectant). For example, in addition to components described above, the formulations described herein may comprise pharmaceutically acceptable excipients, such as carriers, solvents, dispersants, diluents, fillers, stabilizers, preservatives, etc.

Methods of Preparing Complexes and Compositions Thereof

Complexes of a lipidated cationic peptide compound, other lipid components, and a polyanionic compound and compositions thereof can be prepared through a variety of physical and/or chemical methods to modulate their physical, chemical, and biological properties. These typically involve rapid combination of the lipidated cationic peptide compound (e.g., a tertiary amino lipidated and/or PEGylated cationic peptide or a lipitoid) in water or a water-miscible organic solvent with the desired polyanionic compound (e.g., oligonucleotide) in water or an aqueous buffer solution. These methods can include simple mixing of the components by pipetting, or microfluidic mixing processes such as those involving T-mixers, vortex mixers, or other chaotic mixing structures. The compositions of the present disclosure may be prepared in a similar fashion.

In one aspect, the present disclosure provides a method of preparing the complexes and compositions as described herein, comprising contacting one or more lipidated cationic peptide compounds, one or more phospholipids, one or more shielding lipids and optionally one or more structural lipids with one or more polyanionic compounds. In some embodiments, provided herein is a method of preparing a composition, comprising contacting one or more tertiary amino lipidated and/or PEGylated cationic peptide compounds, one or more phospholipids, one or more shielding lipids and optionally one or more structural lipids with one or more polyanionic compounds. In other embodiments, provided herein is a method of preparing a composition, comprising contacting one or more lipitoids, one or more phospholipids, one or more shielding lipids and optionally one or more structural lipids with one or more polyanionic compounds.

In some embodiments, the method of preparing a composition comprising complexes comprising one or more polyanionic compounds, one or more lipidated cationic peptide compounds, one or more phospholipids, one or more shielding lipids, and optionally one or more structural lipids comprises contacting a solution comprising the one or more lipidated cationic peptide compounds, one or more phospholipids, one or more shielding lipids and optionally one or more structural lipids with a solution comprising the one or more polyanionic compounds. In certain embodiments, the polyanionic compound comprises a nucleic acid. In some embodiments, the one or more lipidated cationic peptide compounds comprise one or more tertiary amino lipidated and/or PEGylated cationic peptide compounds. In other embodiments, the one or more cationic compounds comprise one or more lipitoids.

Additional components in the complexes and composition, such as the additional components of polymers, surface-active agents, targeting agents or excipients, may be admixed and combined with the composition before, during or after the principal components of the polyanionic compounds and the lipid components have been combined.

The particular process conditions for preparing the complexes and compositions described herein may be adjusted or selected accordingly to provide the desired physical properties of the compositions. For example, parameters for mixing the components of the compositions which may influence the final compositions may include but are not limited to order of mixing, temperature of mixing, mixing speed/rate, flow rate, concentrations of stock solutions, mass ratio of components (e.g., peptide:cargo), and solvents.

Methods of Using Complexes and Formulations Thereof

As described above, the compositions described herein facilitate the delivery of polyanionic compounds to cells, particularly endocellular environments. As such, the compositions may find use in a number of clinical applications as well as research applications. The delivery of a polyanionic compound to a cell may be used for clinical applications such as those related to prophylactic, diagnostic, and/or therapeutic methods. For example, in some embodiments, suitable clinical applications may include vaccination, cancer immunotherapy, protein replacement therapy, and/or in vivo gene editing, ex vivo cell therapy transfection, ex vivo stem cell induction. Methods of delivering a polyanionic compound to a cell may also be useful for research or non-clinical applications, including for biological assays and reagents.

In another aspect, provided herein are methods of delivering a polyanionic compound to a cell. In some embodiments, the method of delivering a polyanionic compound to a cell comprises contacting the cell with a complex comprising one or more polyanionic compounds, and lipid components, wherein the lipid components comprises optionally one or more structural lipids; one or more phospholipids; one or more shielding lipids; and one or more lipidated cationic peptide compounds. In other embodiments, the method of delivering a polyanionic compound to a cell comprises contacting the cell with a complex comprising one or more polyanionic compounds, and lipid components, wherein the lipid components comprises optionally one or more structural lipids; one or more phospholipids; one or more shielding lipids; and one or more tertiary amino lipidated and/or PEGylated cationic peptide compounds of formula (I) or salts thereof. In yet other embodiments, the method of delivering a polyanionic compound to a cell comprises contacting the cell with a complex comprising one or more polyanionic compounds, and lipid components, wherein the lipid components comprises optionally one or more structural lipids; one or more phospholipids; one or more shielding lipids; and one or more lipitoids of formula (11). In some embodiments of the foregoing methods, the contacting is by endocytosis.

In still other embodiments, the method of delivering a polyanionic compound to a cell comprises contacting the cell with a composition comprising complexes comprising one or more polyanionic compounds, and lipid components, wherein the lipid components comprises optionally one or more structural lipids; one or more phospholipids; one or more shielding lipids; and one or more lipidated cationic peptide compounds. In other embodiments, the method of delivering a polyanionic compound to a cell comprises contacting the cell with a composition comprising complexes comprising one or more polyanionic compounds, and lipid components, wherein the lipid components comprises optionally one or more structural lipids; one or more phospholipids; one or more shielding lipids; and one or more tertiary amino lipidated and/or PEGylated cationic peptide compounds of formula (I) or salts thereof. In yet other embodiments, the method of delivering a polyanionic compound to a cell comprises contacting the cell with a composition comprising complexes comprising one or more polyanionic compounds, and lipid components, wherein the lipid components comprises optionally one or more structural lipids; one or more phospholipids; one or more shielding lipids; and one or more lipitoids of formula (II).

In some embodiments of the foregoing methods, the methods of delivering a polyanionic compound to a cell comprise contacting the cell with a complex comprising one or more polyanionic compounds, and lipid components, wherein the lipid components comprises optionally one or more structural lipids; one or more phospholipids; one or more shielding lipids; and one or more lipidated cationic peptide compounds, wherein the cell is contacted in vitro, ex vivo, or in vivo. In certain embodiments, the methods of delivering a polyanionic compound to a cell comprise contacting the cell with a complex comprising one or more polyanionic compounds, and lipid components, wherein the lipid components comprises one or more structural lipids; one or more phospholipids; one or more shielding lipids; and one or more lipidated cationic peptide compounds, wherein the cell is contacted in vitro, ex vivo, or in vivo.

In other embodiments, the methods of delivering a polyanionic compound to a cell comprise contacting the cell with a composition comprising a complex comprising one or more polyanionic compounds, and lipid components, wherein the lipid components comprises optionally one or more structural lipids; one or more phospholipids; one or more shielding lipids; and one or more lipidated cationic peptide compounds, wherein the cell is contacted in vitro, ex vivo, or in vivo. In certain embodiments, the methods of delivering a polyanionic compound to a cell comprise contacting the cell with a composition comprising a complex comprising one or more polyanionic compounds, and lipid components, wherein the lipid components comprises one or more structural lipids; one or more phospholipids; one or more shielding lipids; and one or more lipidated cationic peptide compounds, wherein the cell is contacted in vitro, ex vivo, or in vivo.

In some embodiments wherein the cell is contacted in vitro, the cell is a HeLa cell. In other embodiments wherein the cell is contacted in vivo, the complex, or composition thereof, or formulation thereof of the present disclosure are administered to a mammalian subject. A mammalian subject may include but is not limited to a human or a mouse subject. In yet other embodiments wherein the cell is contacted ex vivo, the cell is obtained from a human or mouse subject.

In some embodiments of the foregoing methods wherein the cell is contacted in vivo, the complexes and compositions as described herein may be administered by injection. In certain embodiments, the complexes and compositions thereof as described herein may be administered by injection (intravenous (IV), subcutaneous (SC), intramuscular (IM), intrathecal.) In some embodiments, the complexes and compositions are administered by intravenous (IV), subcutaneous (SC), intramuscular (IM) or intrathecal injection. In other embodiments, the complexes and compositions as described herein are administered by bolus injection or intravenous infusion. In other embodiments wherein the cell is contacted in vivo, the complexes and compositions of the present disclosure are administered by nasal or oral inhalation. In some embodiments wherein the cell is contacted in vivo, the complexes and compositions described herein are administered orally. In still other embodiments wherein the cell is contacted in vivo, the complexes and compositions are administered via absorption into the mucous membrane (including topical, intra-anal, buccal, intravaginal, etc.).

It should be understood that clinical applications, such as the diagnostic, prophylactic and therapeutic examples disclosed above, may involve dosing regimens (e.g., dosage levels and time courses for administration) which may be varied as appropriate to the specific complexes and compositions being used, the route of administration, the subject to which the complexes and compositions are being administered, and/or the desired physiological effect. For example, in some embodiments, the methods of the present disclosure comprise administering the complex or composition at a dose of 0.001 mg/kg to about 1 mg/kg of bodyweight.

EXAMPLES

The presently disclosed subject matter will be better understood by reference to the following Examples, which are provided as exemplary of the invention, and not by way of limitation.

Example 1

Synthesis of Exemplary Tertiary Amino Lipidated Cationic Peptides for Nucleic Acid Delivery The following example describes the general protocol for synthesis of the tertiary amino lipidated and/or PEGylated cationic peptide compounds of formula (I) as described herein.

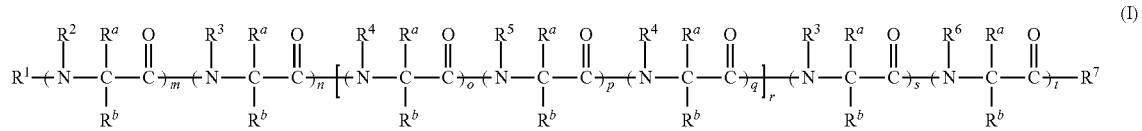

In the description provided below, all $R^a$ and $R^b$ are —H. All polymers are synthesized using bromoacetic acid and primary amines FIGS. 2B-2E provides some of the exemplary substituents of the primary amines at $R^2$, $R^3$, $R^4$, $R^5$, and $R^6$ to prepare the tertiary amino lipidated and/or PEGylated cationic peptide compounds of the present disclosure.

An Fmoc-Rink amide resin is used as the solid support. The Fmoc group on the resin is deprotected with 20% (v/v) piperidine-dimethylformamide (DMF). The amino resin is then amidated with bromoacetic acid. This is followed by amination of the α-carbon by nucleophilic displacement of the bromide with a primary amine. The two steps are successively repeated to produce the desired cationic peptide sequence.

All reactions and washings are performed at room temperature unless otherwise noted. Washing of the resin refers to the addition of a wash solvent (usually DMF or dimethylsulfoxide (DMSO)) to the resin, agitating the resin so that a uniform slurry is obtained, followed by thorough draining of the solvent from the resin. Solvents are removed by vacuum filtration through the fritted bottom of the reaction vessel until the resin appeared dry. In all the syntheses, resin slurries are agitated via bubbling argon up through the bottom of the fritted vessel.

Initial Resin Deprotection. A fritted reaction vessel is charged with Fmoc-Rink amide resin. DMF is added to the resin and this solution is agitated to swell the resin. The DMF is then drained. The Fmoc group is removed by adding 20% piperidine in DMF to the resin, agitating the resin, and draining the resin. 20% piperidine in DMF is added to the resin and agitated for 15 minutes and then drained. The resin is then washed with DMF, six times.

Acylation/Amidation. The deblocked amine is then acylated by adding bromoacetic acid in DMF to the resin followed by N,N-diisoprooplycarbodiimide (DIC) in DMF (FIG. 3A). This solution is agitated for 30 minutes at room temperature and then drained. This step is repeated a second time. The resin is then washed with DMF twice and DMSO once. This is one completed reaction cycle.

Nucleophilic Displacement/Amination. The acylated resin is treated with the desired primary or secondary amine to undergo nucleophilic displacement at the bromine leaving group on the α-carbon (FIG. 3B). This acylation/displacement cycle is repeated (FIG. 3C) until the desired peptide sequence is obtained (FIG. 3D).

Peptide Cleavage from Resin. The dried resin is placed in a glass scintillation vial containing a teflon-coated micro stir bar, and 95% trifluoroacetic acid (TFA) in water is added. The solution is stirred for 20 minutes and then filtered through solid-phase extraction (SPE) column fitted with a polyethylene frit into a polypropylene conical centrifuge tube.

The resin is washed with 1 mL 95% TFA. The combined filtrates are then lyophilized three times from 1:1 acetonitrile:water. The lyophilized peptide (FIG. 3E) is redissolved in absolute ethanol at a concentration of 5 mg/mL or in DMSO at a concentration of 10 mg/mL.

Purification and Characterization. The redissolved crude peptide is purified by preparative HPLC. The purified peptide is characterized by LC-MS analysis.

Example 2

Synthesis and Characterization of Representative Amino Lipidated Peptoids

Amino lipidated peptoids were synthesized by the sub-monomer method described above in Example 1 with bromoacetic acid and N,N'-diisopropylcarbodiimide (DIC). Polystyrene-supported MBHA Fmoc-protected Rink amide (200 mg representative scale, 0.64 mmol/g loading, Protein Technologies) resin was used as a solid support. For bromoacetylation, resin was combined with a 1:1 mixture of 2 M bromoacetic acid and 2M N,N'-diisopropylcarbodiimide (DIC) for 5 minutes. Amine displacement was carried out using a 1M solution of amine in DMF for 1 hour. Following synthesis, crude peptoids were cleaved from resin using 5 mL of a mixture of 95:2.5:2.5 trifluoroacetic acid (TFA):water:triisopropylsilane for 40 minutes at room temperature. Resin was removed by filtration and the filtrate concentrated using a Biotage V10 evaporator. The crude peptoids were further concentrated by lyophilization from a 25% solution of MeCN in water. Purity and identity were assayed with a Waters Acquity UPLC system with Acquity Diode Array UV detector and Waters SQD2 mass spectrometer on a Waters Acquity UPLC Peptide BEH C4 Column over a 5-95% gradient. Select crude peptoids were purified by preparative Waters Prep150LC system with Waters 2489 UV/Visible Detector on a Waters XBridge BEH300 Prep C4 column using a 5-40% acetonitrile in water with 0.1% TFA gradient over 30 minutes.

Table 1A shows representative amino lipidated peptoids prepared by the method described in Example 2. Table 1B provides characterization data for the amino lipidated peptoid compounds 1-72 prepared in Table 1A, including the predicted molecular weight, retention time (in minutes, determined by UPLC-UV measurement at λ=218 nm), and primary observed mass-to-charge ratio (m/z, MH$^+$, by electrospray ionization-mass spectrometry). For each of amino lipidated and PEGylated peptoid compounds 48, 56, 64, and 72, the mass spectra contained several distributions of peaks due to the polydispersity of the PEG moiety (average molecular weight 2000 g/mol) attached to the peptoid. The mass-to-charge ratio peak reported for these amino lipidated and PEGylated peptoid compounds is the central value of the MH$_2^{2+}$ distribution of peaks, with an effective monomer separation δ-22 m/z (—OCH$_2$CH$_2$—, ethylene glycol molecular weight 44 g/mol).

TABLE 1A

| # | Compound Structure |
|---|---|
| 1 | 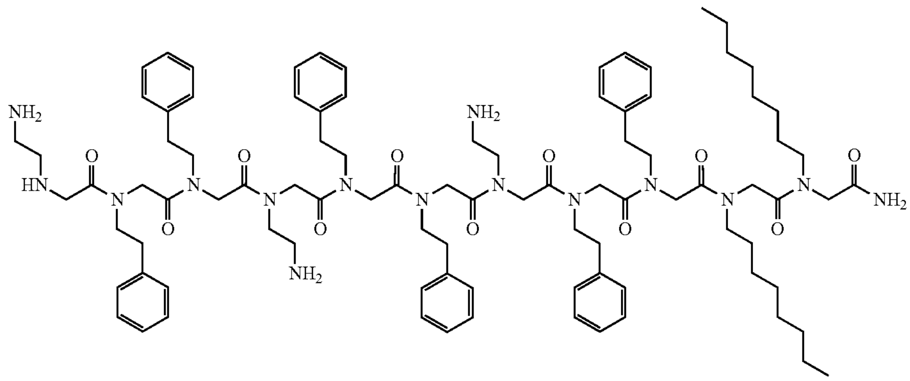 [SMILES: CCCCCCCCN(CC(N)=O)C(=O)CN(CCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CNCCN] |
| 2 | 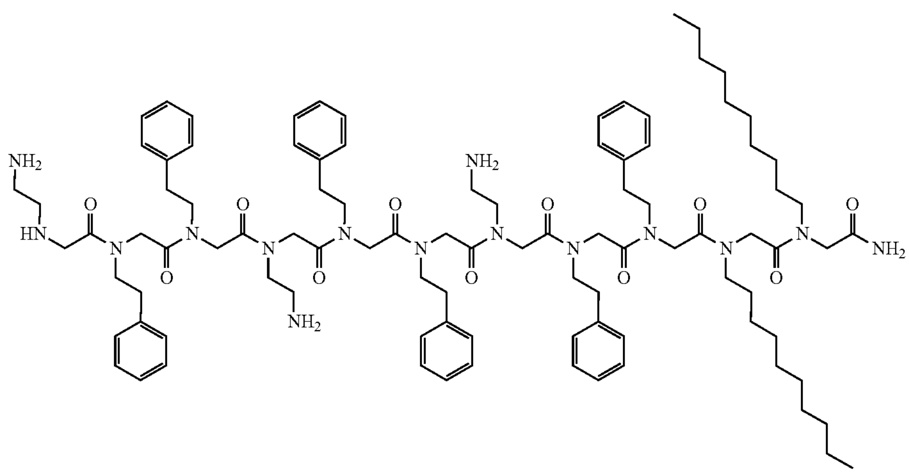 [SMILES: CCCCCCCCCCN(CC(N)=O)C(=O)CN(CCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CNCCN] |
| 3 | 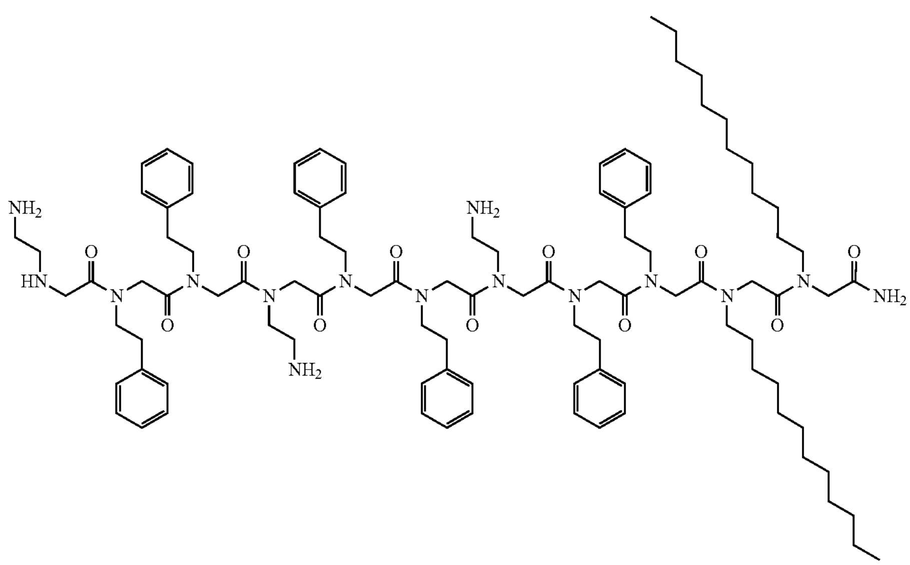 [SMILES: CCCCCCCCCCCCN(CC(N)=O)C(=O)CN(CCCCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CNCCN] |

TABLE 1A-continued
| # | Compound Structure |
|---|---|
| 4 | 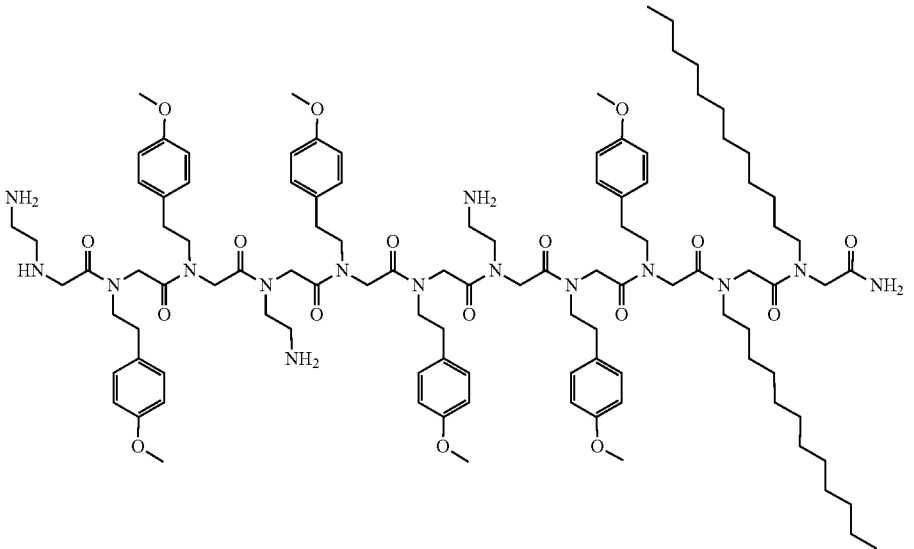 [SMILES: CCCCCCCCCCCCN(CC(N)=O)C(=O)CN(CCCCCCCCCCCC)C(=O)CN(CCc1ccc(OC)cc1)C(=O)CN(CCc1ccc(OC)cc1)C(=O)CN(CCN)C(=O)CN(CCc1ccc(OC)cc1)C(=O)CN(CCc1ccc(OC)cc1)C(=O)CN(CCN)C(=O)CN(CCc1ccc(OC)cc1)C(=O)CN(CCc1ccc(OC)cc1)C(=O)CNCCN] |
| 5 | 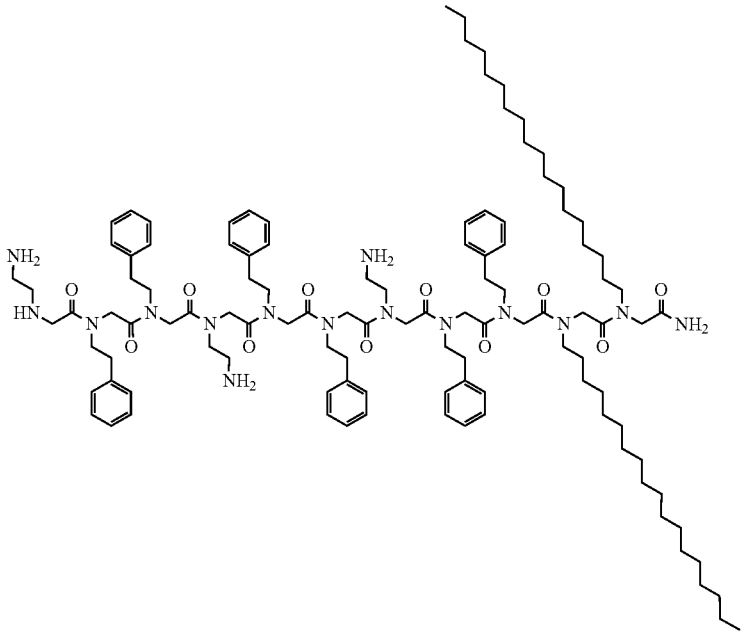 [SMILES: CCCCCCCCCCCCCCCCCCN(CC(N)=O)C(=O)CN(CCCCCCCCCCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CNCCN] |
| 6 | 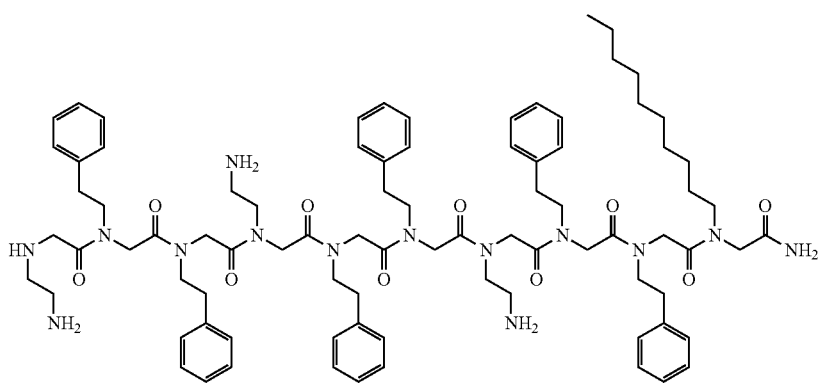 [SMILES: CCCCCCCCCCN(CC(N)=O)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CNCCN] |

TABLE 1A-continued
| # | Compound Structure |
|---|---|
| 7 | 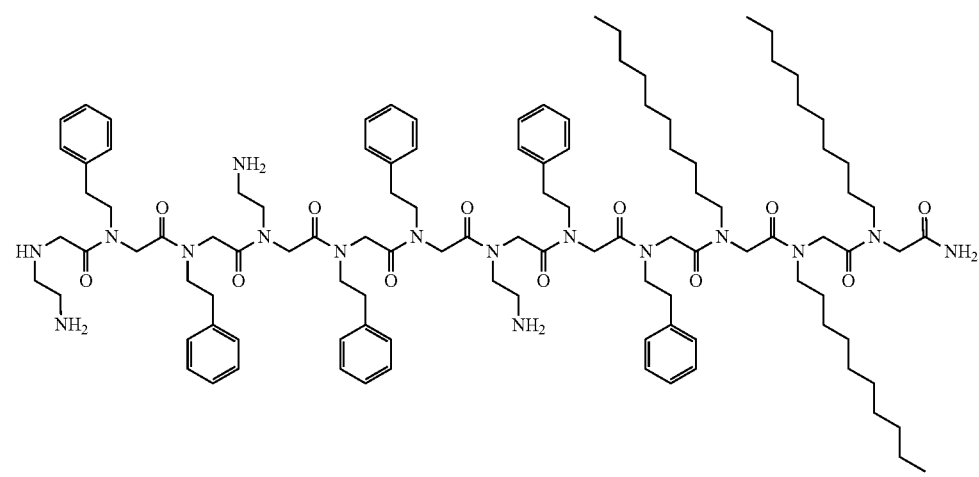 [SMILES: CCCCCCCCCCN(CC(N)=O)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CNCCN] |
| 8 | 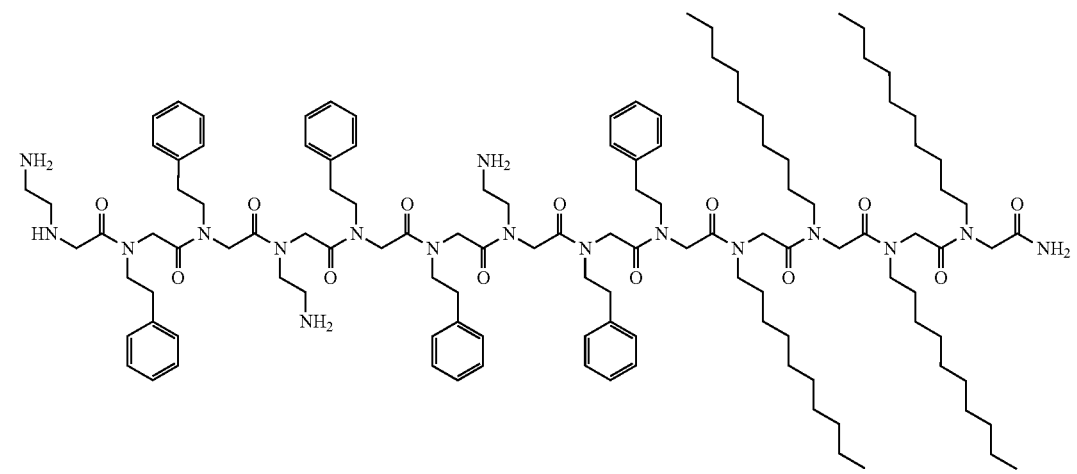 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CNCCN] |
| 9 | 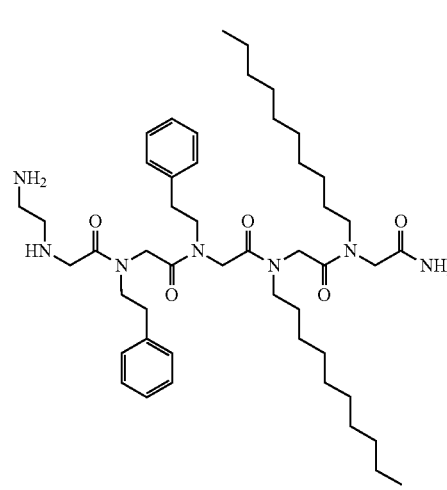 |

TABLE 1A-continued

| # | Compound Structure |
|---|---|
| 10 | 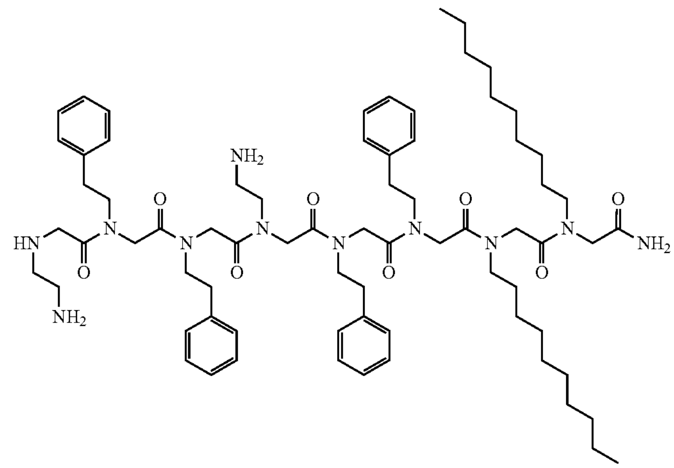 [SMILES: CCCCCCCCCCN(CC(N)=O)C(=O)CN(CCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CNCCN] |
| 11 | 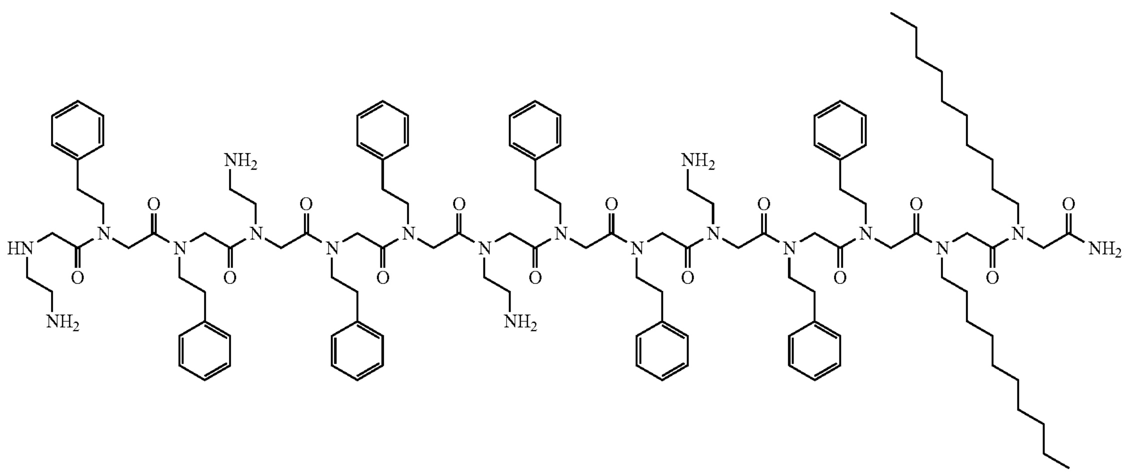 [SMILES: CCCCCCCCCCN(CC(N)=O)C(=O)CN(CCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CNCCN] |
| 12 | 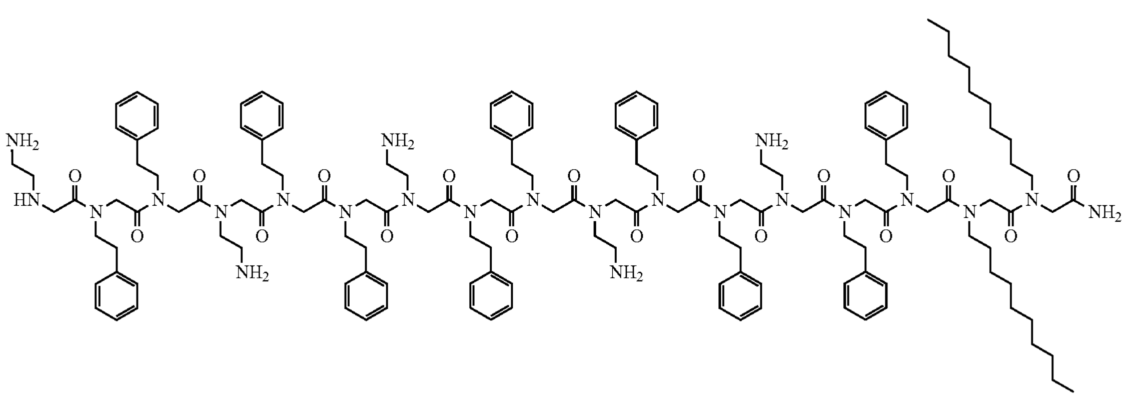 [SMILES: CCCCCCCCCCN(CC(N)=O)C(=O)CN(CCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CNCCN] |

TABLE 1A-continued

| # | Compound Structure |
|---|---|
| 13 | 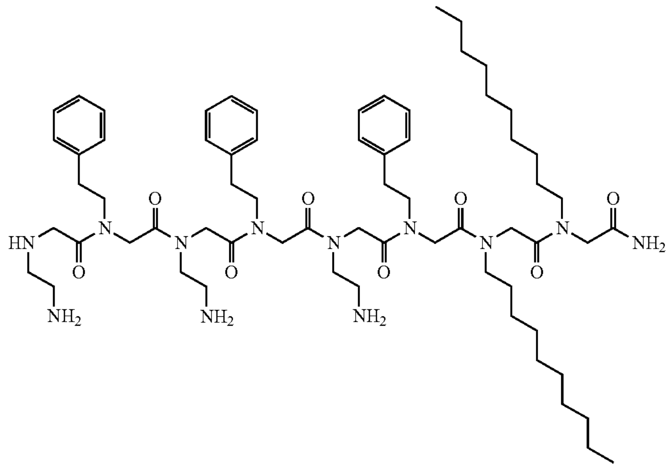 [SMILES: CCCCCCCCCCN(CC(N)=O)C(=O)CN(CCCCCCCCCC)C(=O)CN(CCc1ccccc1)C(=O)CN(CCN)C(=O)CN(CCc1ccccc1)C(=O)CN(CCN)C(=O)CN(CCc1ccccc1)C(=O)CNCCN] |
| 14 | 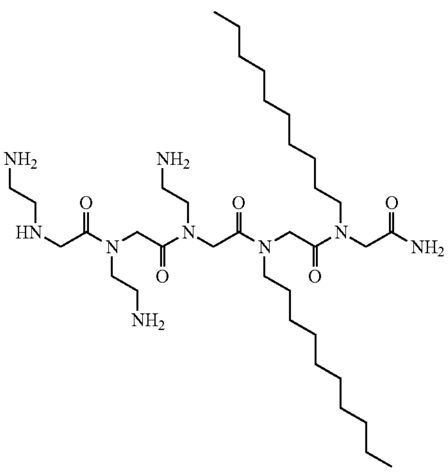 [SMILES: CCCCCCCCCCN(CC(N)=O)C(=O)CN(CCCCCCCCCC)C(=O)CN(CCN)C(=O)CN(CCN)C(=O)CNCCN] |
| 15 | 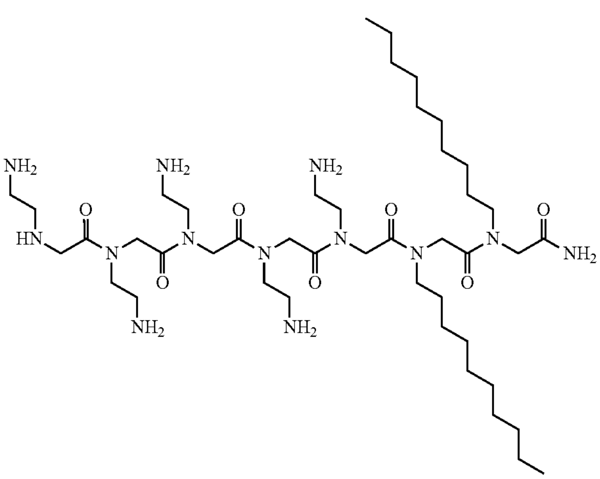 [SMILES: CCCCCCCCCCN(CC(N)=O)C(=O)CN(CCCCCCCCCC)C(=O)CN(CCN)C(=O)CN(CCN)C(=O)CN(CCN)C(=O)CN(CCN)C(=O)CNCCN] |

TABLE 1A-continued

| # | Compound Structure |
|---|---|
| 16 | 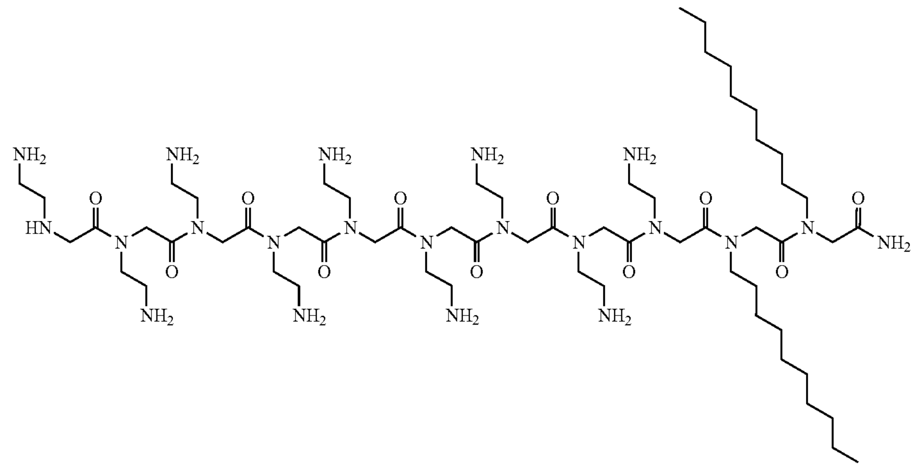 [SMILES: CCCCCCCCCCN(CC(N)=O)C(=O)CN(CCCCCCCCCC)C(=O)CN(CCN)C(=O)CN(CCN)C(=O)CN(CCN)C(=O)CN(CCN)C(=O)CN(CCN)C(=O)CN(CCN)C(=O)CN(CCN)C(=O)CN(CCN)C(=O)CNCCN] |
| 17 | 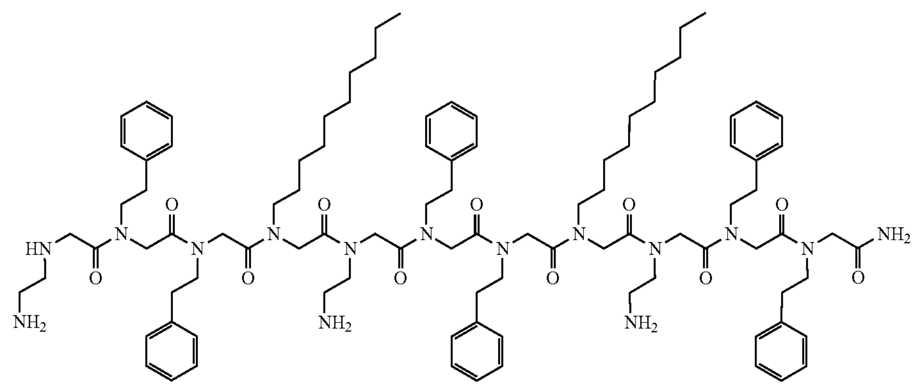 [SMILES: CCCCCCCCCCN(CC(=O)N(CCN)CC(=O)N(CCc1ccccc1)CC(=O)N(CCc1ccccc1)CC(=O)N(CCCCCCCCCC)CC(=O)N(CCN)CC(=O)N(CCc1ccccc1)CC(=O)N(CCc1ccccc1)CC(N)=O)C(=O)CN(CCc1ccccc1)C(=O)CN(CCc1ccccc1)C(=O)CNCCN] |
| 18 | 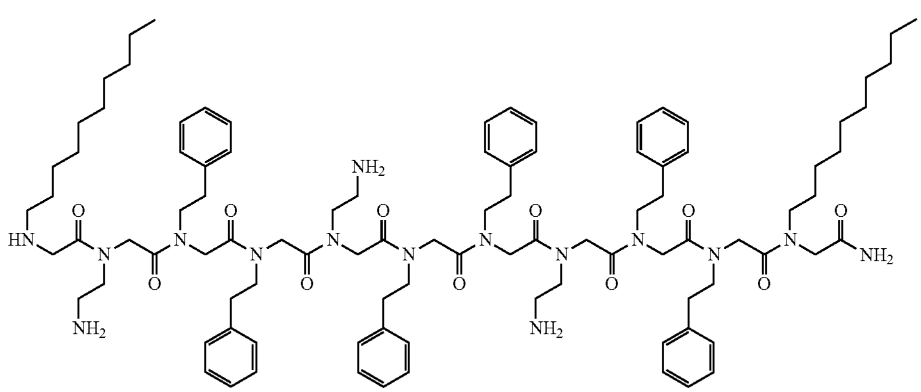 [SMILES: CCCCCCCCCCNCC(=O)N(CCN)CC(=O)N(CCc1ccccc1)CC(=O)N(CCc1ccccc1)CC(=O)N(CCN)CC(=O)N(CCc1ccccc1)CC(=O)N(CCc1ccccc1)CC(=O)N(CCN)CC(=O)N(CCc1ccccc1)CC(=O)N(CCc1ccccc1)CC(=O)N(CCCCCCCCCC)CC(N)=O] |

TABLE 1A-continued

| # | Compound Structure |
|---|---|
| 19 | 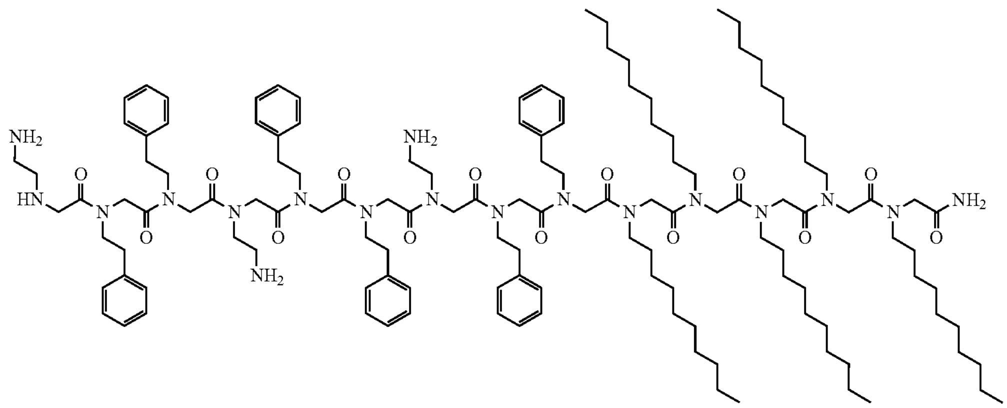 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CNCCN] |
| 20 | 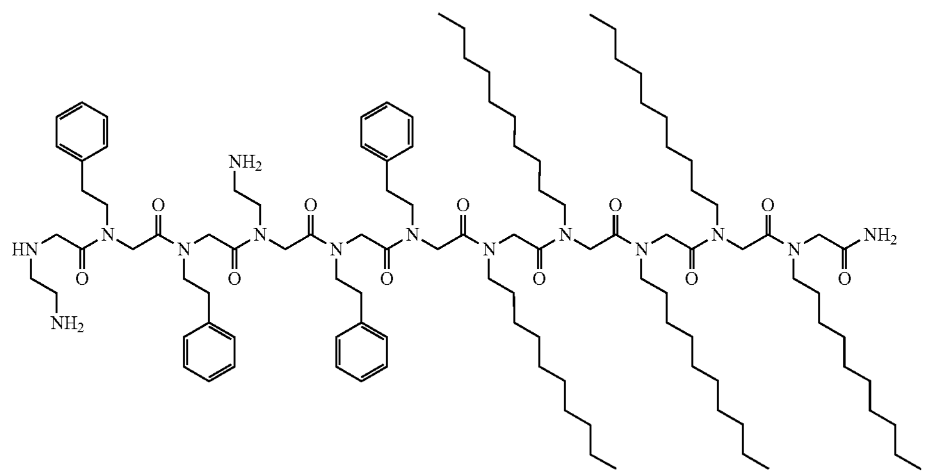 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CNCCN] |
| 21 | 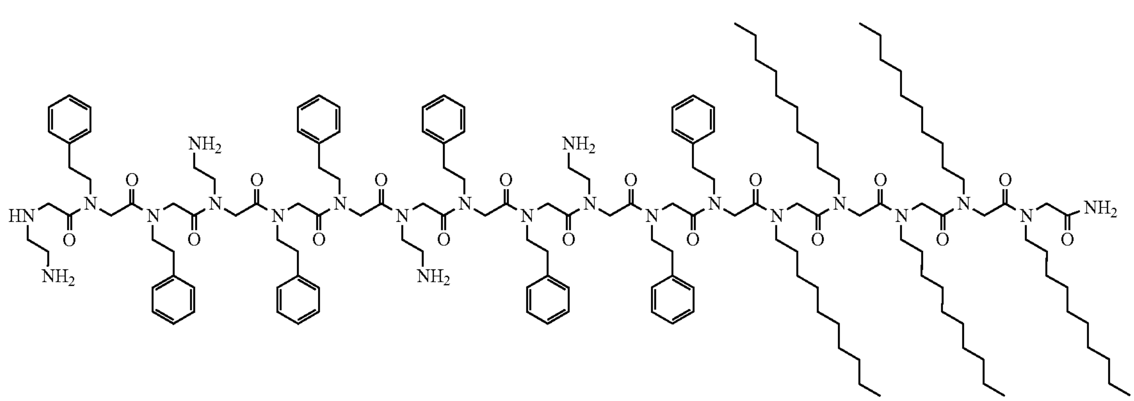 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CNCCN] |

TABLE 1A-continued

| # | Compound Structure |
|---|---|
| 22 | 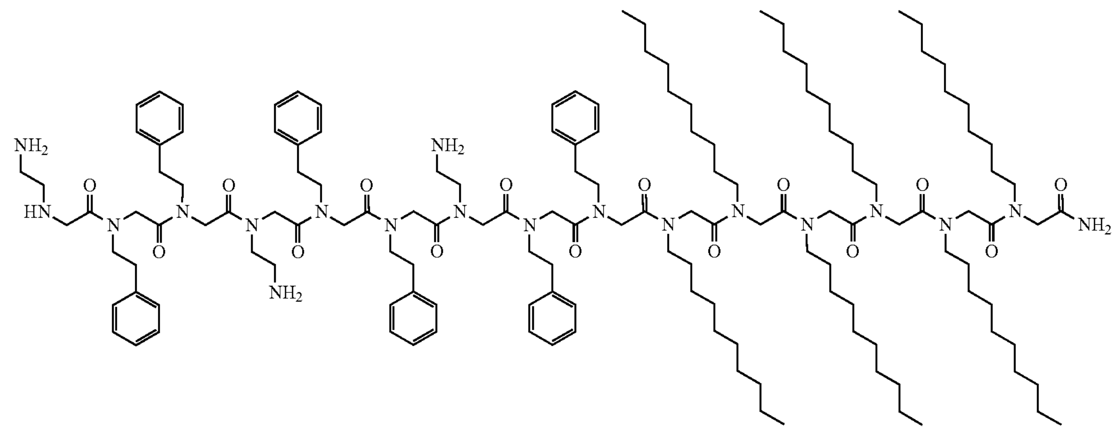 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CNCCN] |
| 23 | 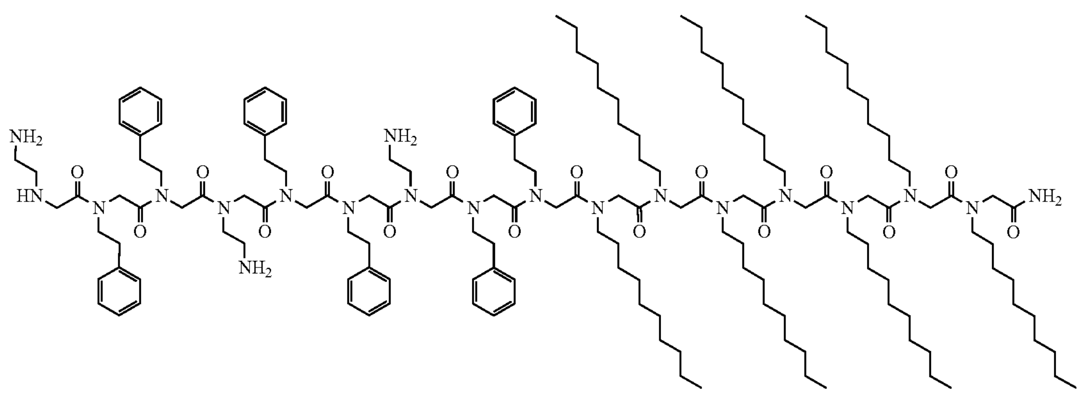 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CNCCN] |
| 24 | 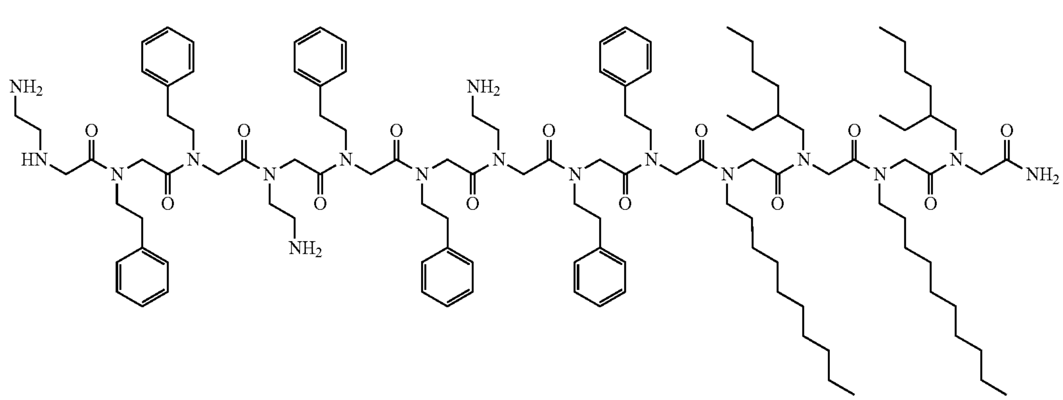 [SMILES: CCCCCCCCCCN(CC(=O)N(CC(=O)N(CCCCCCCCCC)CC(=O)N(CC(N)=O)CC(CC)CCCC)CC(CC)CCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CNCCN] |

TABLE 1A-continued

| # | Compound Structure |
|---|---|
| 25 | 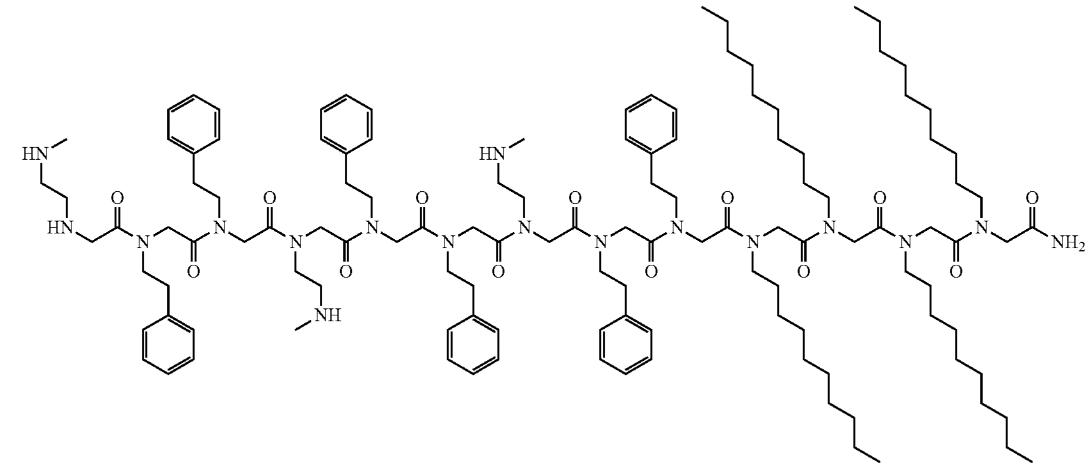 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCNC)C(=O)CN(CCc1ccccc1)C(=O)CN(CCc1ccccc1)C(=O)CN(CCNC)C(=O)CN(CCc1ccccc1)C(=O)CN(CCc1ccccc1)C(=O)CNCCNC] |
| 26 | 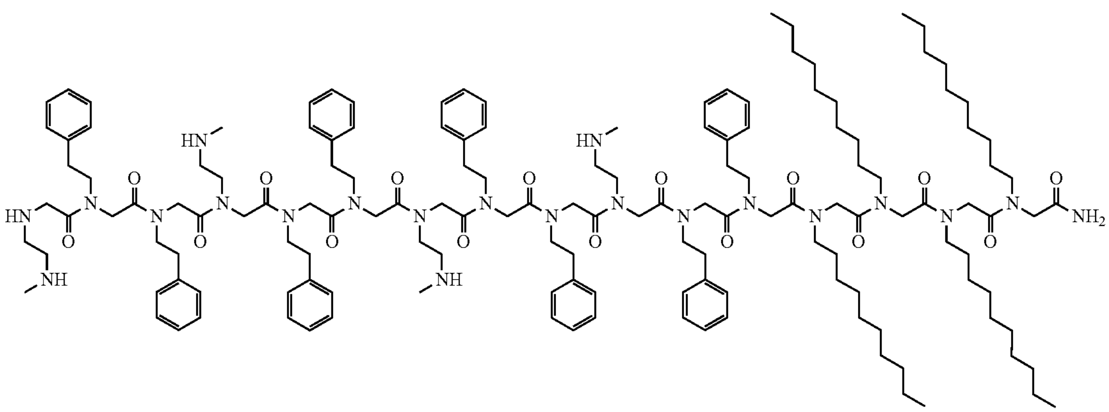 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCNC)C(=O)CN(CCc1ccccc1)C(=O)CN(CCc1ccccc1)C(=O)CN(CCNC)C(=O)CN(CCc1ccccc1)C(=O)CN(CCc1ccccc1)C(=O)CN(CCNC)C(=O)CN(CCc1ccccc1)C(=O)CN(CCc1ccccc1)C(=O)CNCCNC] |
| 27 | 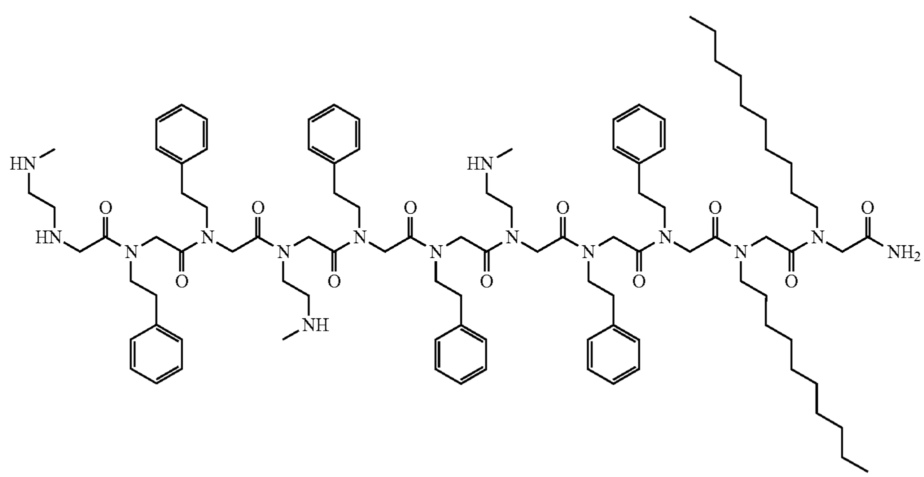 [SMILES: CCCCCCCCCCN(CC(N)=O)C(=O)CN(CCCCCCCCCC)C(=O)CN(CCc1ccccc1)C(=O)CN(CCc1ccccc1)C(=O)CN(CCNC)C(=O)CN(CCc1ccccc1)C(=O)CN(CCc1ccccc1)C(=O)CN(CCNC)C(=O)CN(CCc1ccccc1)C(=O)CN(CCc1ccccc1)C(=O)CNCCNC] |

TABLE 1A-continued

| # | Compound Structure |
|---|---|
| 28 | 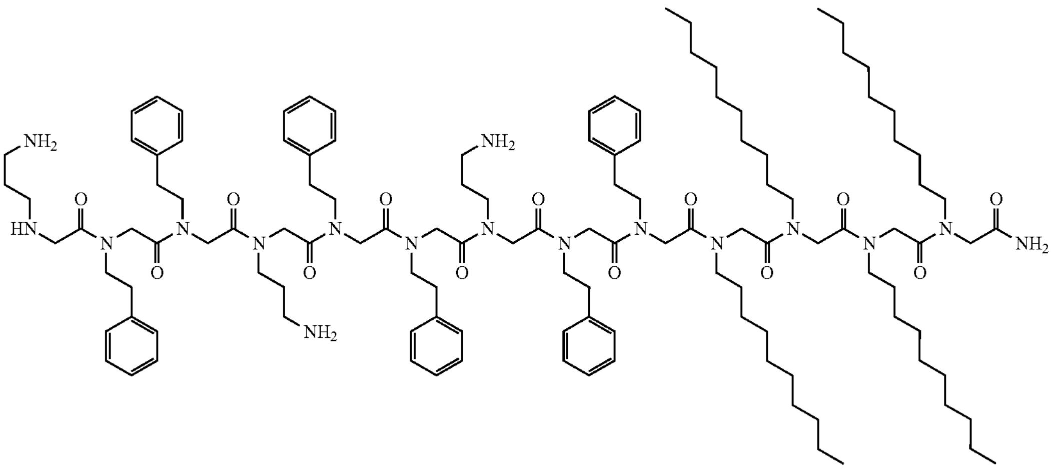 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCCN)C(=O)CN(CCc1ccccc1)C(=O)CN(CCc1ccccc1)C(=O)CN(CCCN)C(=O)CN(CCc1ccccc1)C(=O)CN(CCc1ccccc1)C(=O)CNCCCN] |
| 29 | 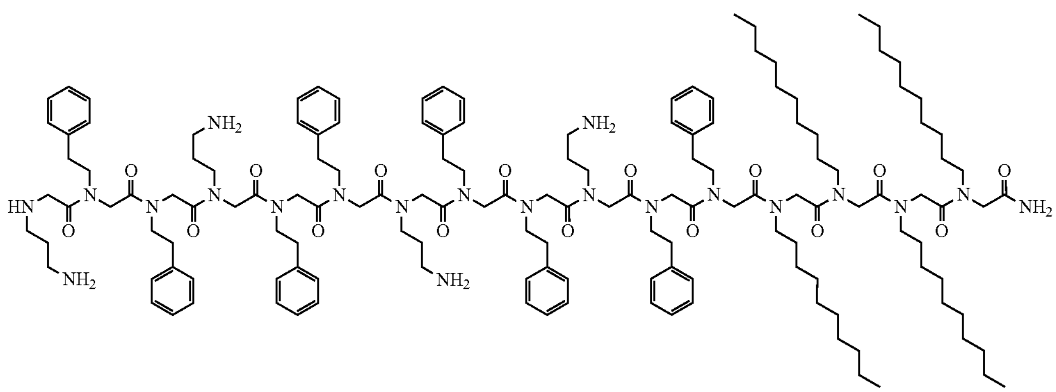 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCCN)C(=O)CN(CCc1ccccc1)C(=O)CN(CCc1ccccc1)C(=O)CN(CCCN)C(=O)CN(CCc1ccccc1)C(=O)CN(CCc1ccccc1)C(=O)CN(CCCN)C(=O)CN(CCc1ccccc1)C(=O)CN(CCc1ccccc1)C(=O)CNCCCN] |
| 30 | 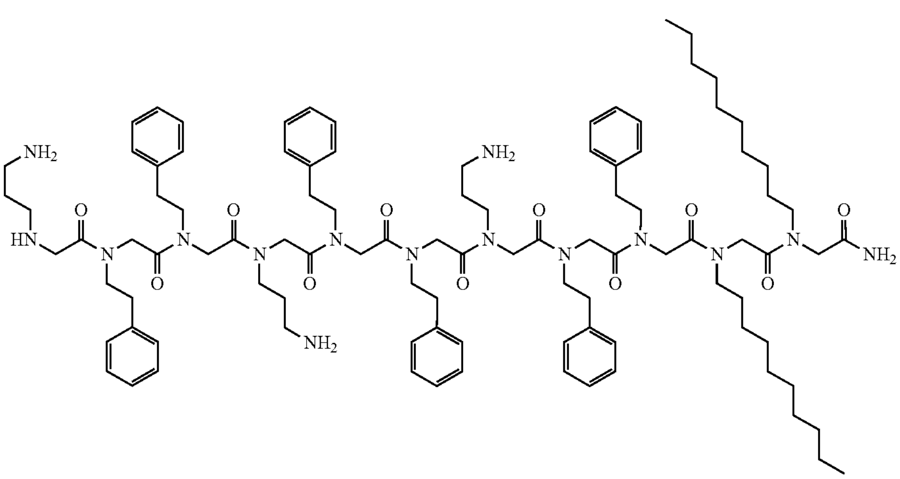 [SMILES: CCCCCCCCCCN(CC(N)=O)C(=O)CN(CCCCCCCCCC)C(=O)CN(CCc1ccccc1)C(=O)CN(CCc1ccccc1)C(=O)CN(CCCN)C(=O)CN(CCc1ccccc1)C(=O)CN(CCc1ccccc1)C(=O)CN(CCCN)C(=O)CN(CCc1ccccc1)C(=O)CN(CCc1ccccc1)C(=O)CNCCCN] |

TABLE 1A-continued

| # | Compound Structure |
|---|---|
| 31 | 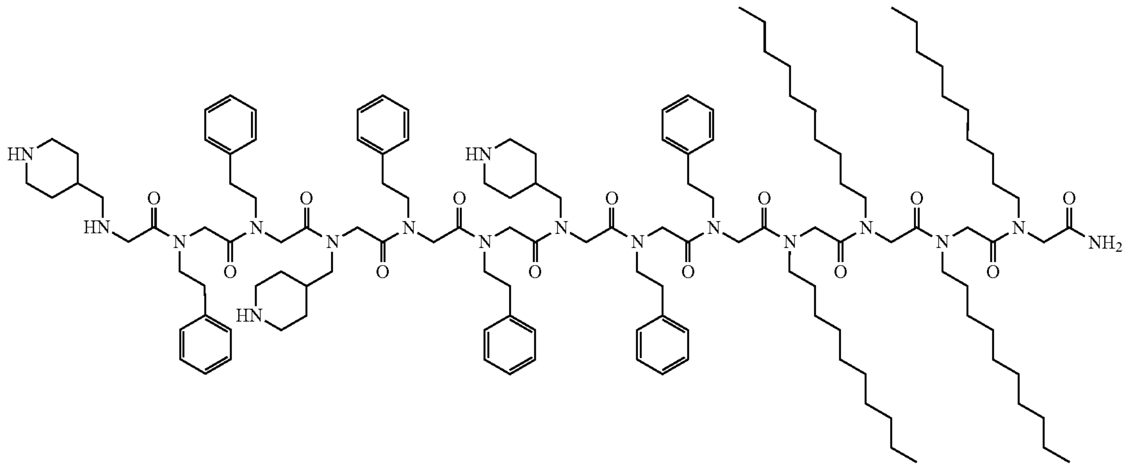 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CC1CCNCC1)C(=O)CN(CCc1ccccc1)C(=O)CN(CCc1ccccc1)C(=O)CN(CC1CCNCC1)C(=O)CN(CCc1ccccc1)C(=O)CN(CCc1ccccc1)C(=O)CNCC1CCNCC1] |
| 32 | 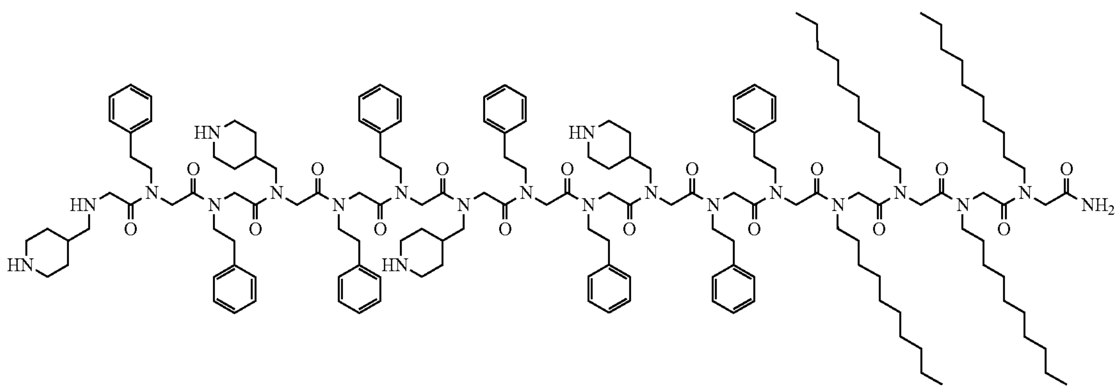 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CC1CCNCC1)C(=O)CN(CCc1ccccc1)C(=O)CN(CCc1ccccc1)C(=O)CN(CC1CCNCC1)C(=O)CN(CCc1ccccc1)C(=O)CN(CCc1ccccc1)C(=O)CN(CC1CCNCC1)C(=O)CN(CCc1ccccc1)C(=O)CN(CCc1ccccc1)C(=O)CNCC1CCNCC1] |
| 33 | 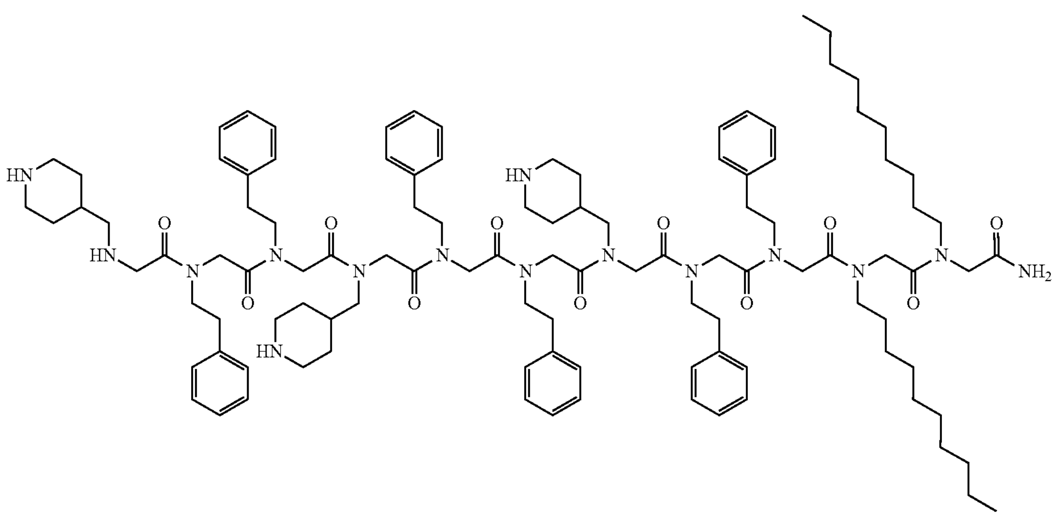 [SMILES: CCCCCCCCCCN(CC(N)=O)C(=O)CN(CCCCCCCCCC)C(=O)CN(CCc1ccccc1)C(=O)CN(CCc1ccccc1)C(=O)CN(CC1CCNCC1)C(=O)CN(CCc1ccccc1)C(=O)CN(CCc1ccccc1)C(=O)CN(CC1CCNCC1)C(=O)CN(CCc1ccccc1)C(=O)CN(CCc1ccccc1)C(=O)CNCC1CCNCC1] |

TABLE 1A-continued

| # | Compound Structure |
|---|---|
| 34 | 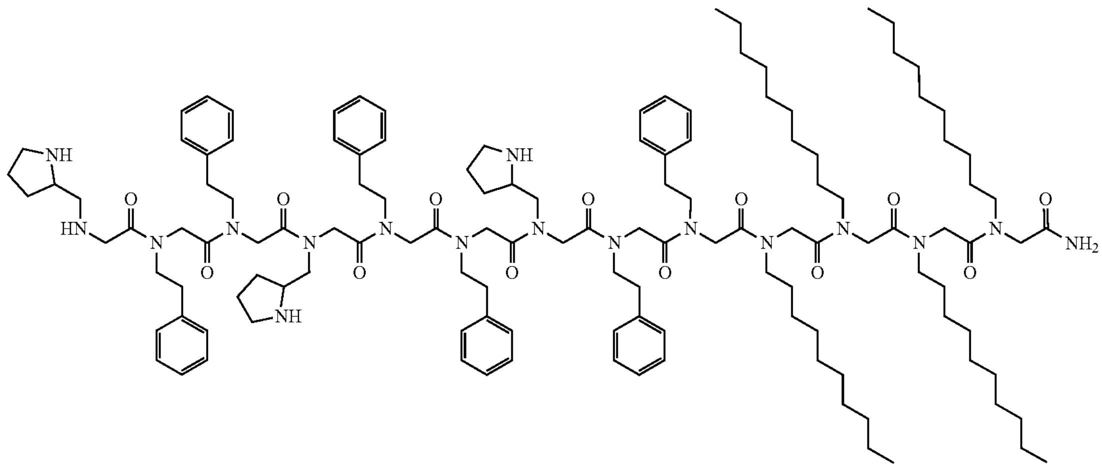 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CC1CCCN1)C(=O)CN(CCc1ccccc1)C(=O)CN(CCc1ccccc1)C(=O)CN(CC1CCCN1)C(=O)CN(CCc1ccccc1)C(=O)CN(CCc1ccccc1)C(=O)CNCC1CCCN1] |
| 35 | 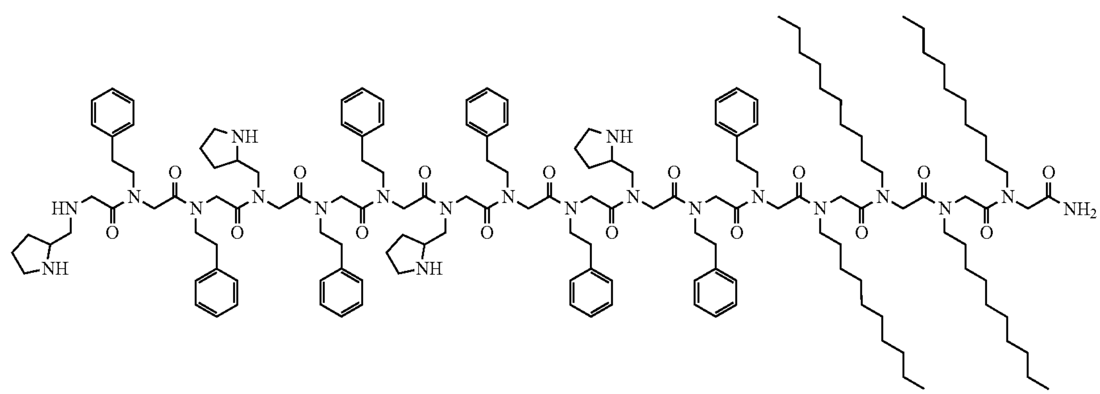 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CC1CCCN1)C(=O)CN(CCc1ccccc1)C(=O)CN(CCc1ccccc1)C(=O)CN(CC1CCCN1)C(=O)CN(CCc1ccccc1)C(=O)CN(CCc1ccccc1)C(=O)CN(CC1CCCN1)C(=O)CN(CCc1ccccc1)C(=O)CN(CCc1ccccc1)C(=O)CNCC1CCCN1] |
| 36 | 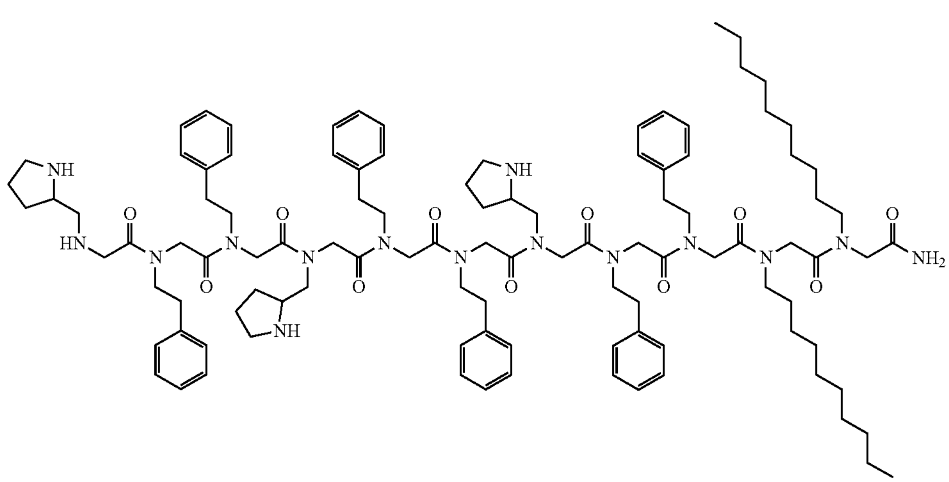 [SMILES: CCCCCCCCCCN(CC(N)=O)C(=O)CN(CCCCCCCCCC)C(=O)CN(CCc1ccccc1)C(=O)CN(CCc1ccccc1)C(=O)CN(CC1CCCN1)C(=O)CN(CCc1ccccc1)C(=O)CN(CCc1ccccc1)C(=O)CN(CC1CCCN1)C(=O)CN(CCc1ccccc1)C(=O)CN(CCc1ccccc1)C(=O)CNCC1CCCN1] |

TABLE 1A-continued
| # | Compound Structure |
|---|---|
| 37 | 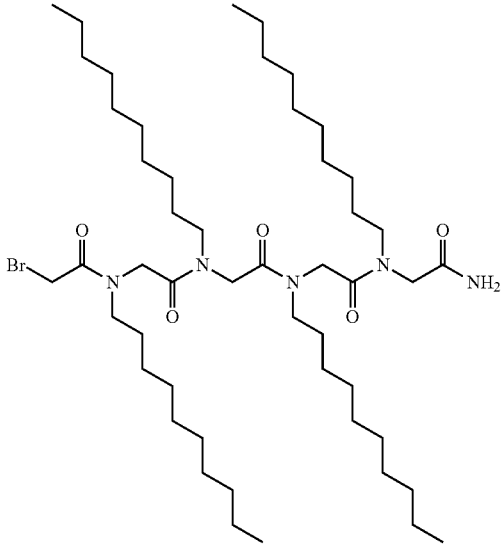 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CBr] |
| 38 | 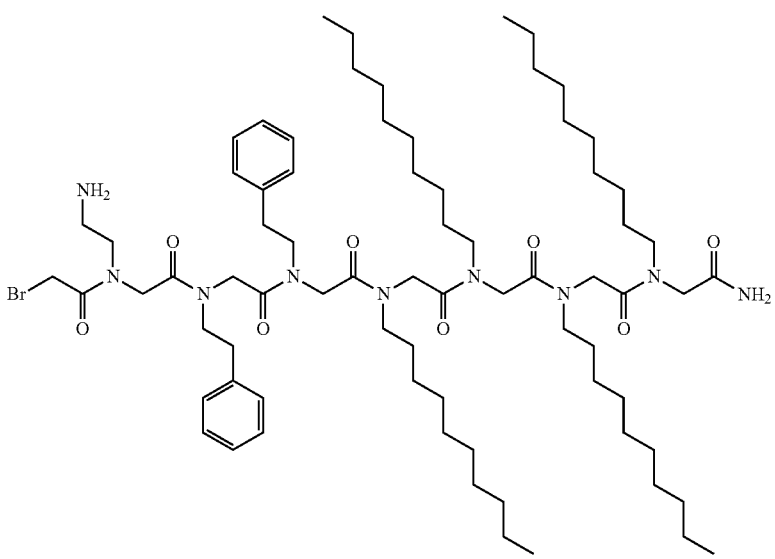 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CBr] |
| 39 | 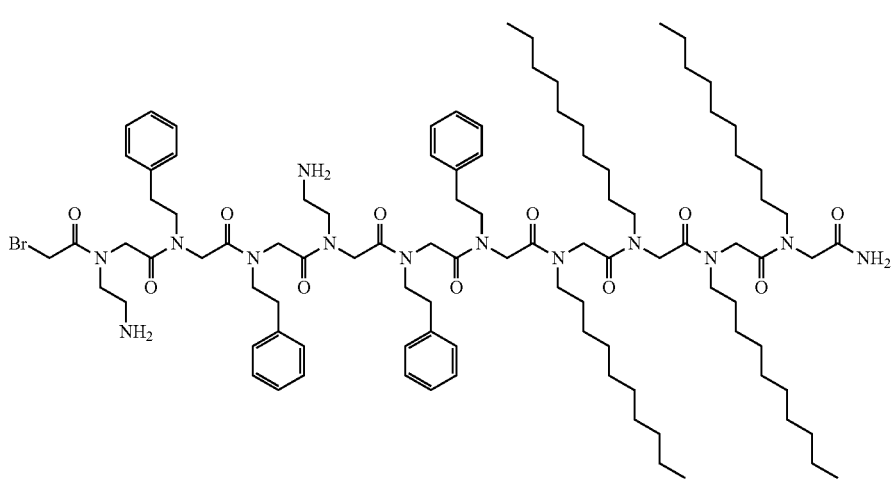 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CBr] |

TABLE 1A-continued

| # | Compound Structure |
|---|---|
| 40 | (chemical structure) |
| 41 | (chemical structure) |
| 42 | (chemical structure) |

TABLE 1A-continued

| # | Compound Structure |
|---|---|
| 43 | 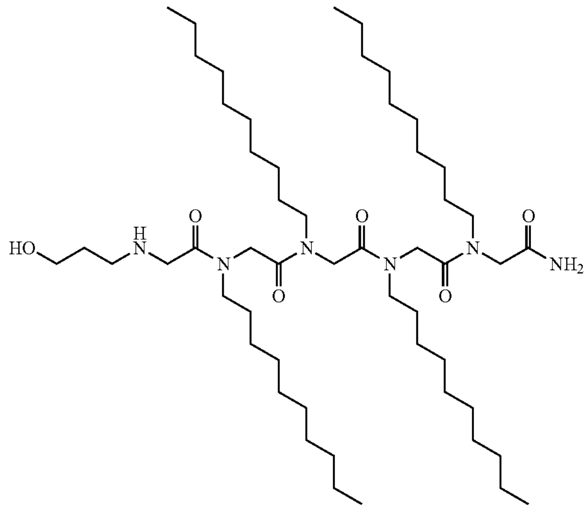 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CNCCCO] |
| 44 | 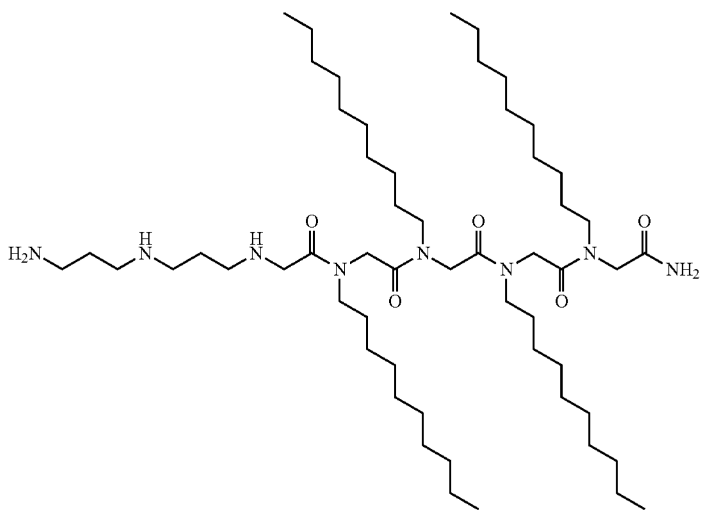 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CNCCCNCCCN] |
| 45 | 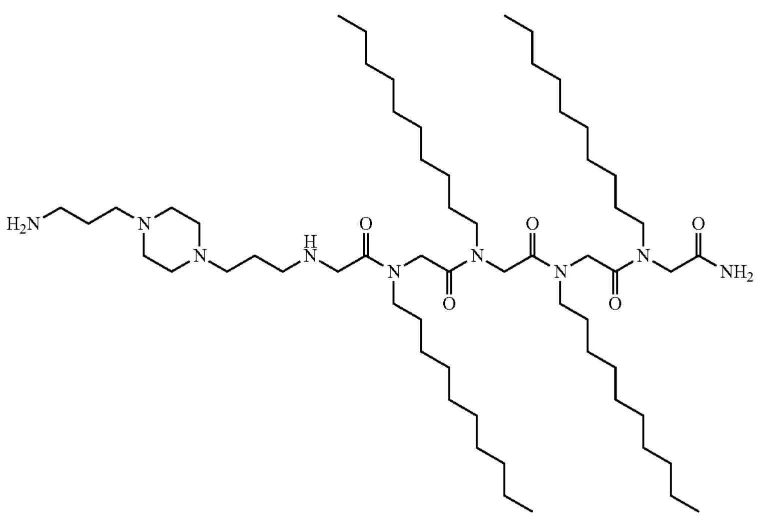 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CNCCCN1CCN(CCCN)CC1] |

TABLE 1A-continued
| # | Compound Structure |
|---|---|
| 46 | 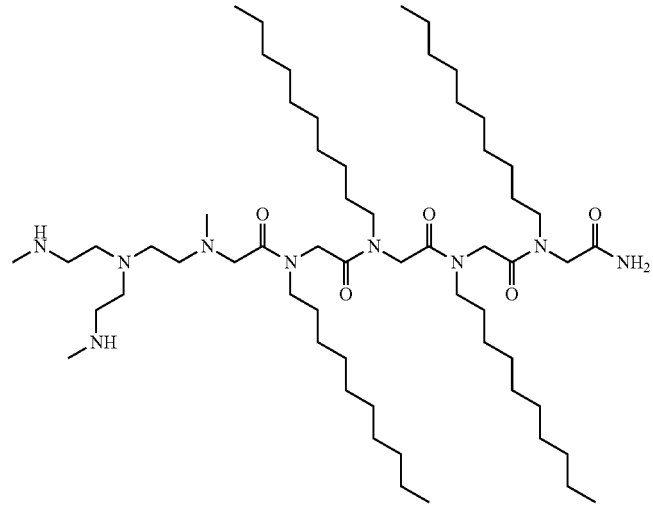 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(C)CCN(CCNC)CCNC] |
| 47 | 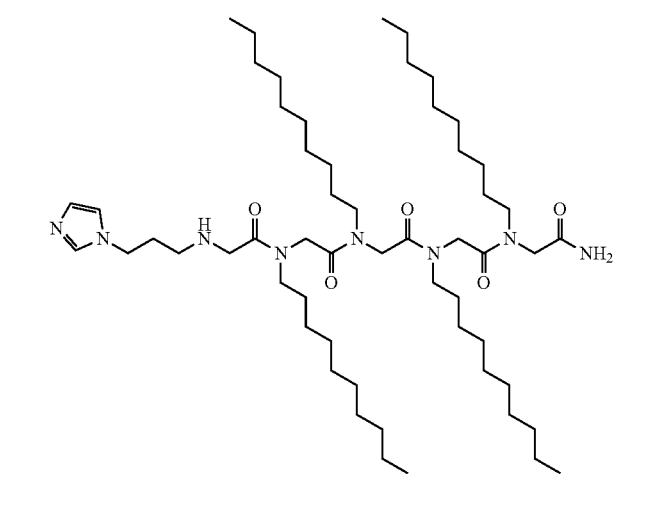 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CNCCCn1ccnc1] |
| 48 | 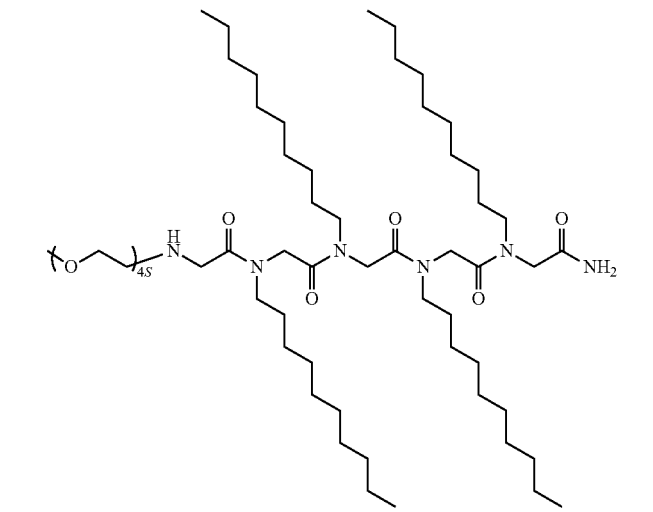 |

TABLE 1A-continued

| # | Compound Structure |
|---|---|
| 49 | 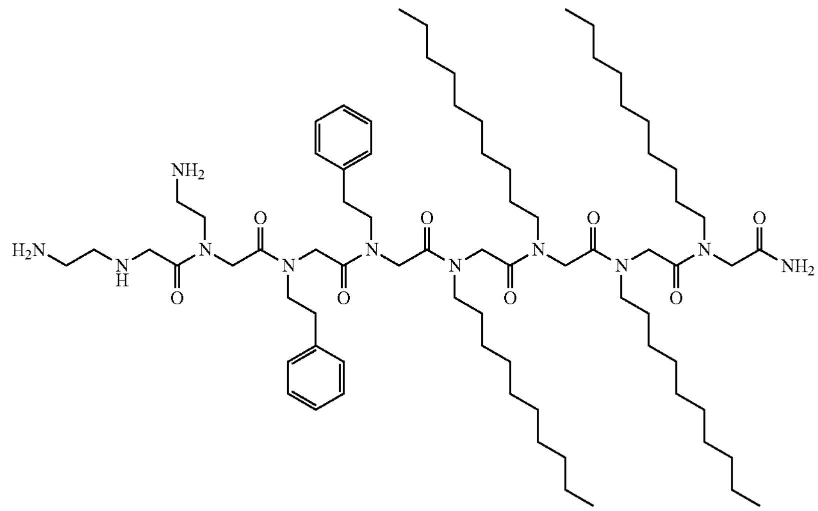 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CNCCN] |
| 50 | 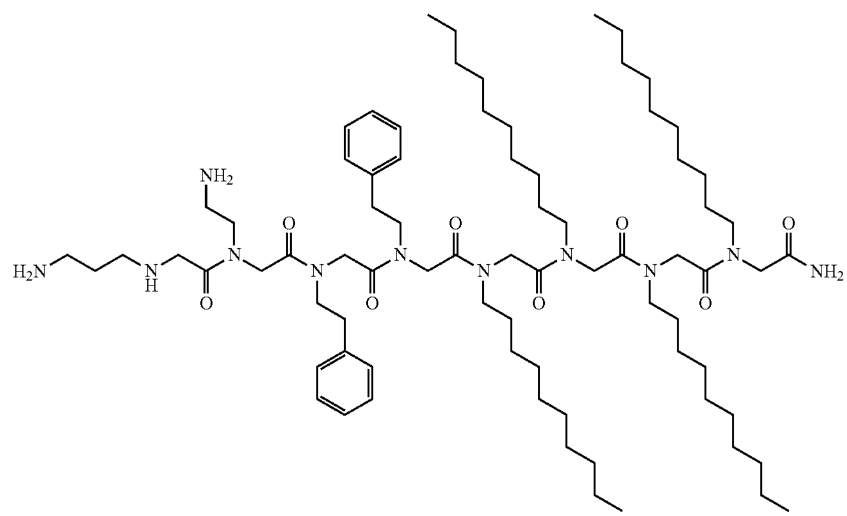 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CNCCCN] |
| 51 | 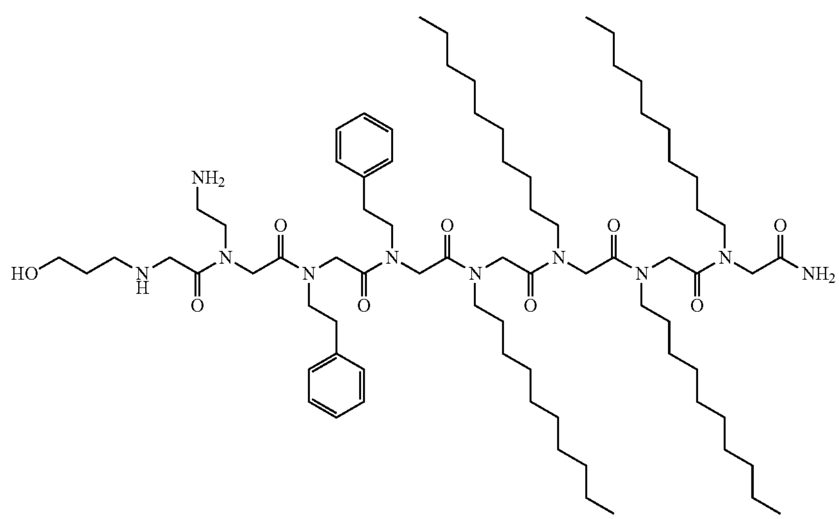 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CNCCCO] |

TABLE 1A-continued
| # | Compound Structure |
|---|---|
| 52 | 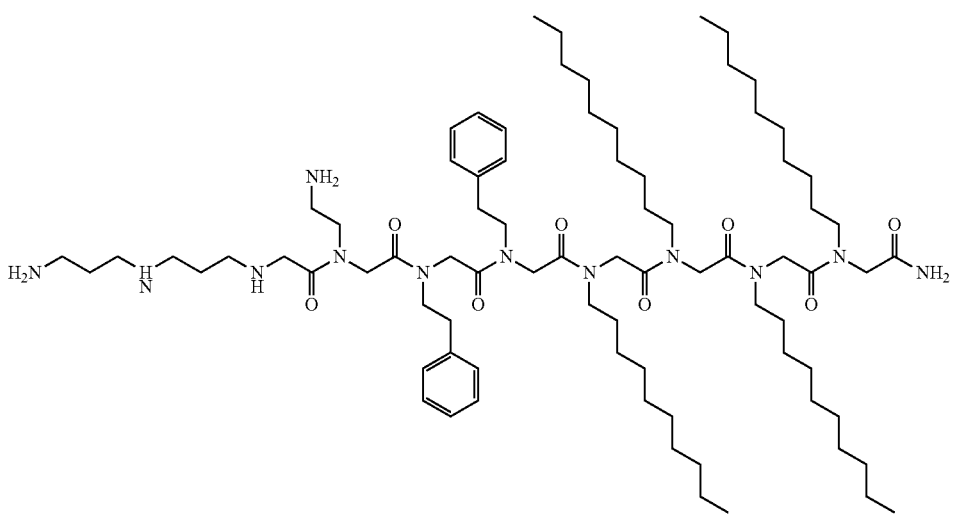 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CNCCCNCCCN] |
| 53 | 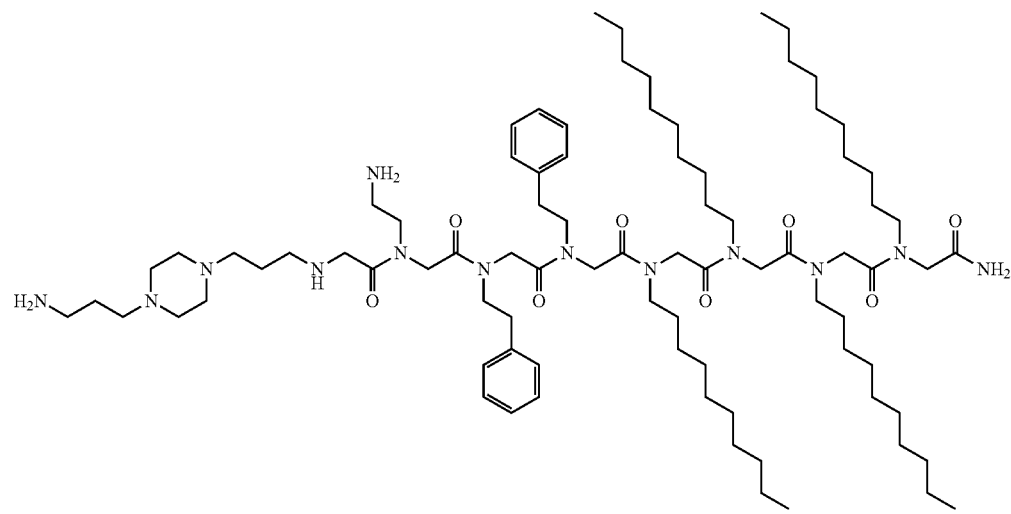 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CNCCCN1CCN(CCCN)CC1] |
| 54 | 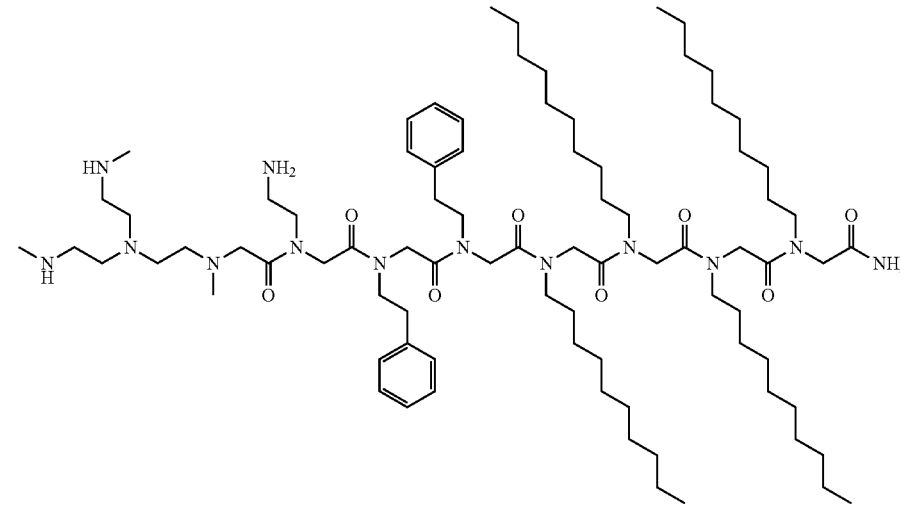 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CN(C)CCN(CCNC)CCNC] |

TABLE 1A-continued

| # | Compound Structure |
|---|---|
| 55 | 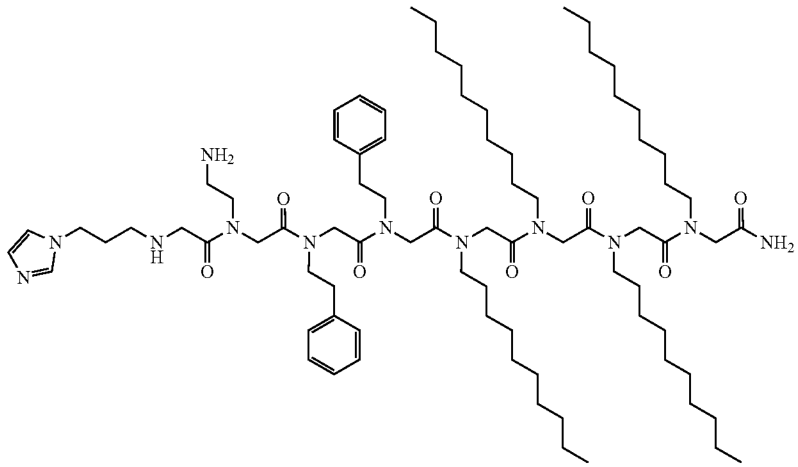 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CNCCCn1ccnc1] |
| 56 | 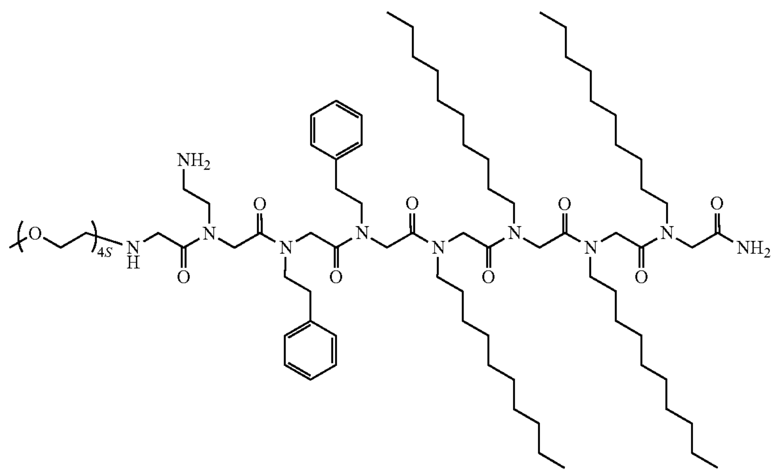 |
| 57 | 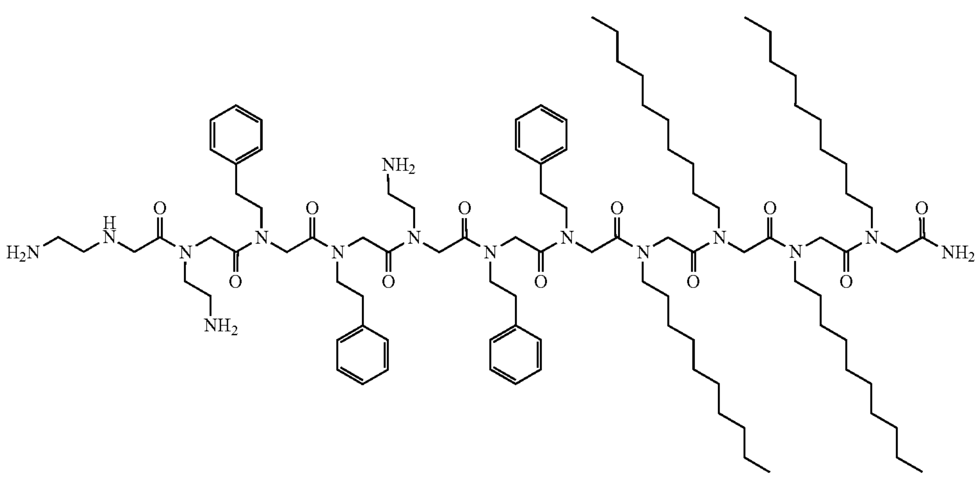 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CNCCN] |

TABLE 1A-continued

| # | Compound Structure |
|---|---|
| 58 | 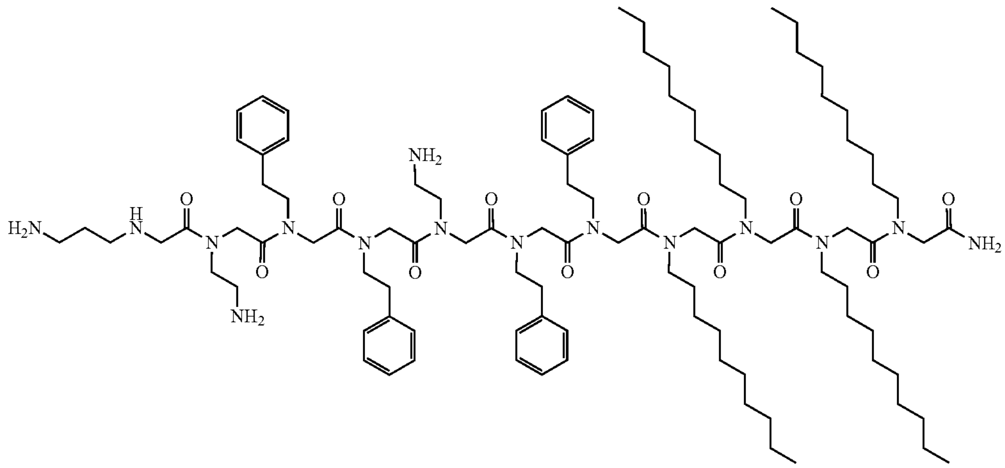 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CNCCCN] |
| 59 | 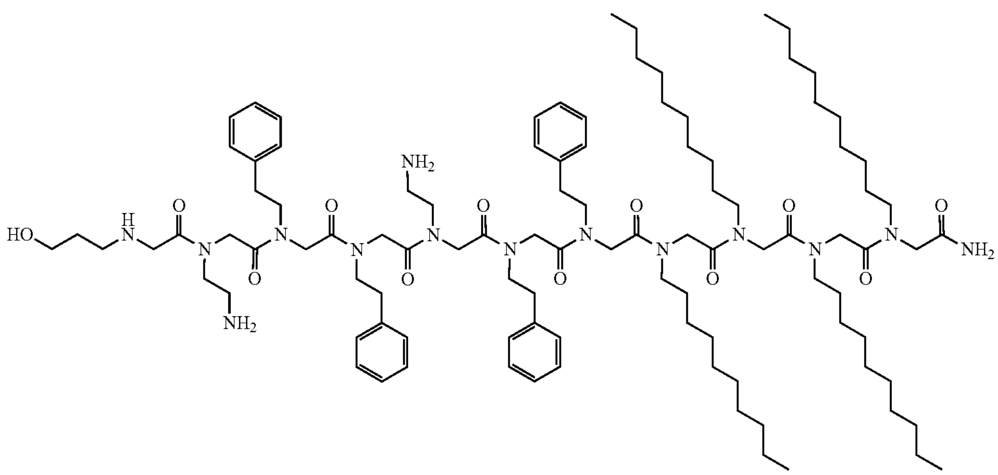 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CNCCCO] |
| 60 | 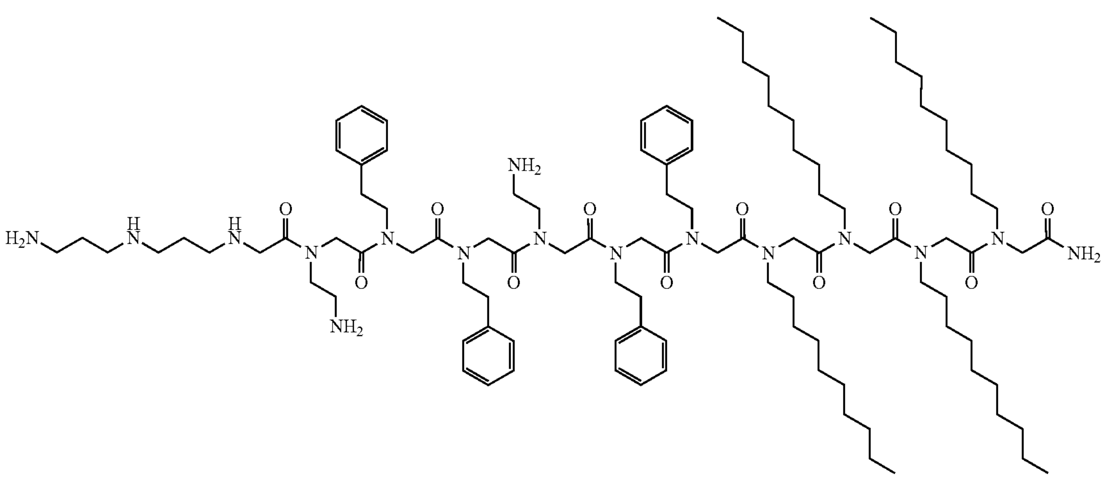 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CNCCCNCCCN] |

TABLE 1A-continued
| # | Compound Structure |
|---|---|
| 61 | 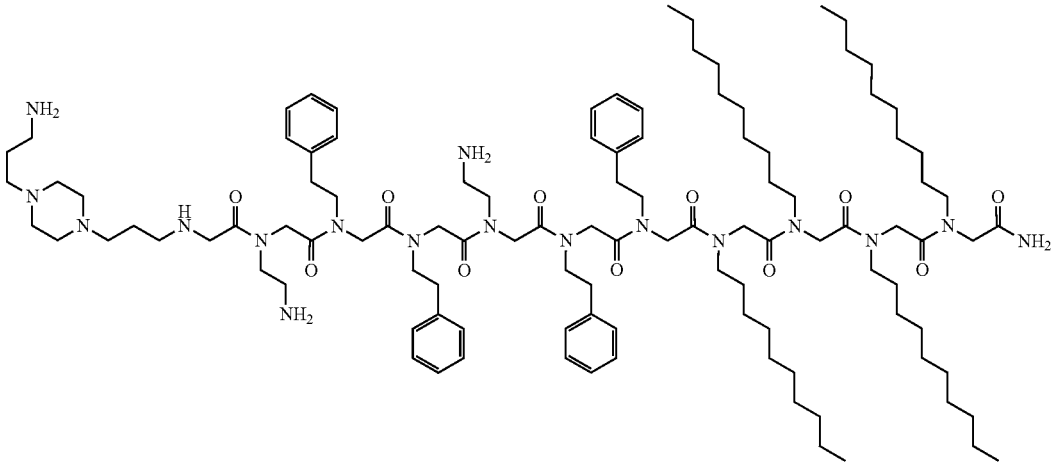 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CNCCCN1CCN(CCCN)CC1] |
| 62 | 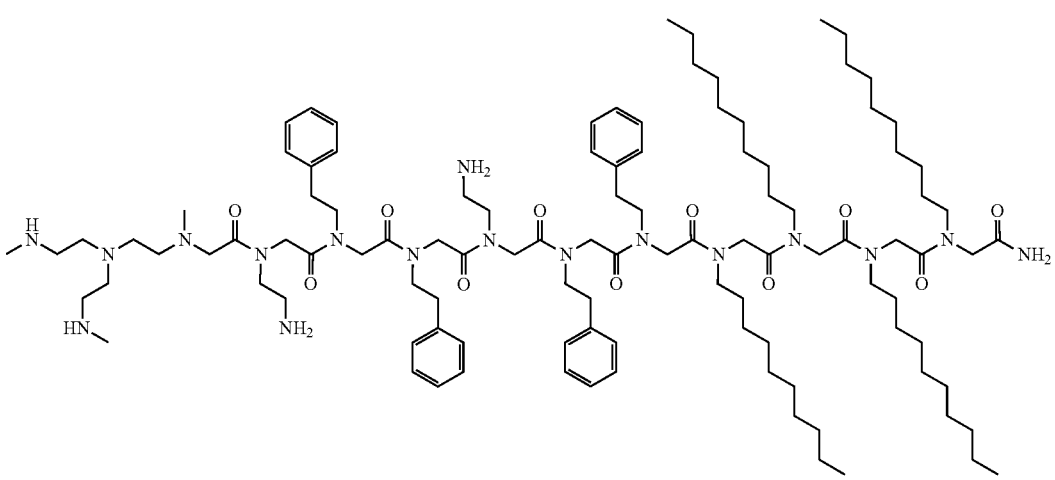 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(C)CCN(CCNC)CCNC] |
| 63 | 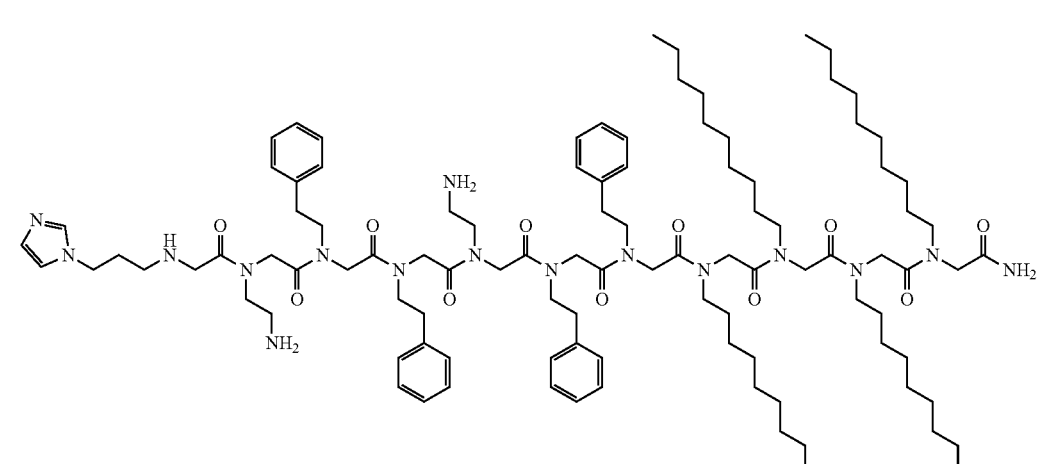 |

TABLE 1A-continued
| # | Compound Structure |
|---|---|
| 64 | 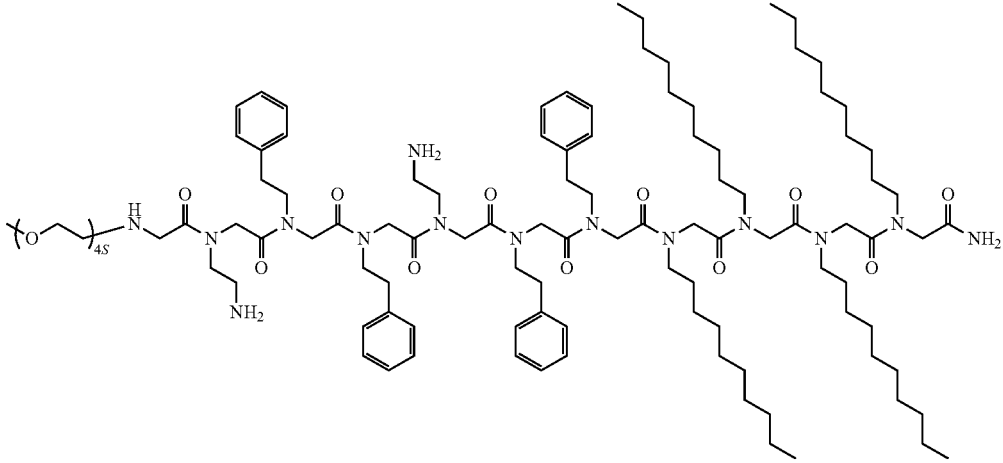 |
| 65 | 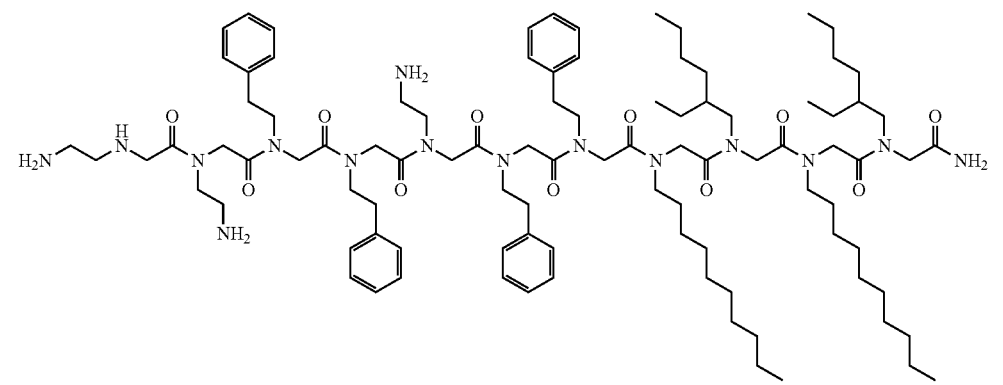 [SMILES: CCCCCCCCCCN(CC(=O)N(CC(=O)N(CCCCCCCCCC)CC(=O)N(CC(N)=O)CC(CC)CCCC)CC(CC)CCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CNCCN] |
| 66 | 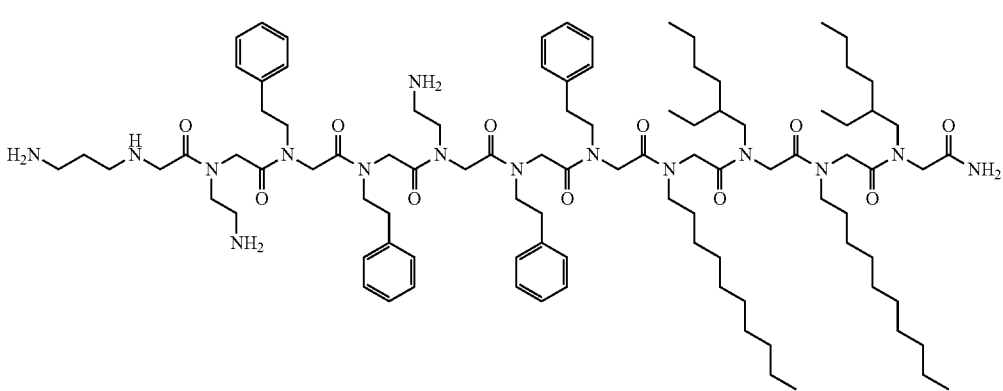 [SMILES: CCCCCCCCCCN(CC(=O)N(CC(=O)N(CCCCCCCCCC)CC(=O)N(CC(N)=O)CC(CC)CCCC)CC(CC)CCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CNCCCN] |
| 67 | 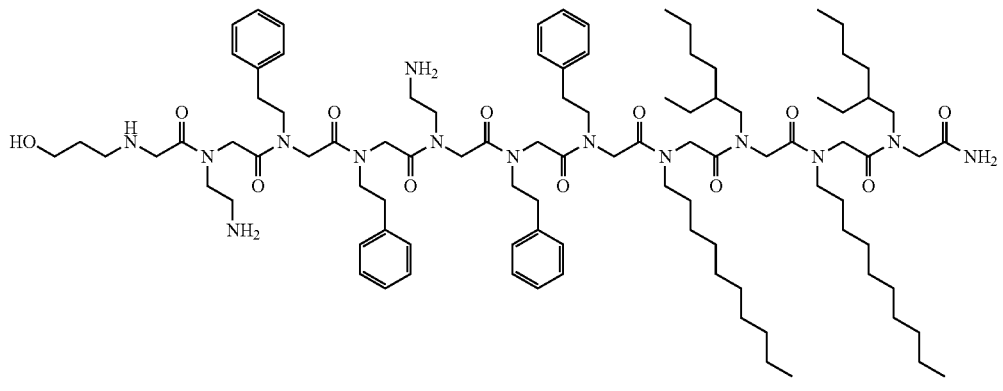 [SMILES: CCCCCCCCCCN(CC(=O)N(CC(=O)N(CCCCCCCCCC)CC(=O)N(CC(N)=O)CC(CC)CCCC)CC(CC)CCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CNCCCO] |

TABLE 1A-continued

| # | Compound Structure |
|---|---|
| 68 | 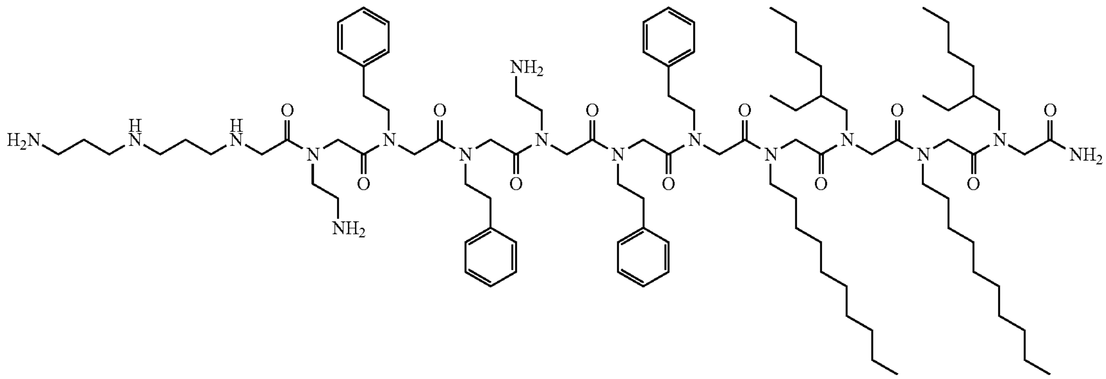 [SMILES: CCCCCCCCCCN(CC(=O)N(CC(=O)N(CCCCCCCCCC)CC(=O)N(CC(N)=O)CC(CC)CCCC)CC(CC)CCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CNCCCNCCCN] |
| 69 | 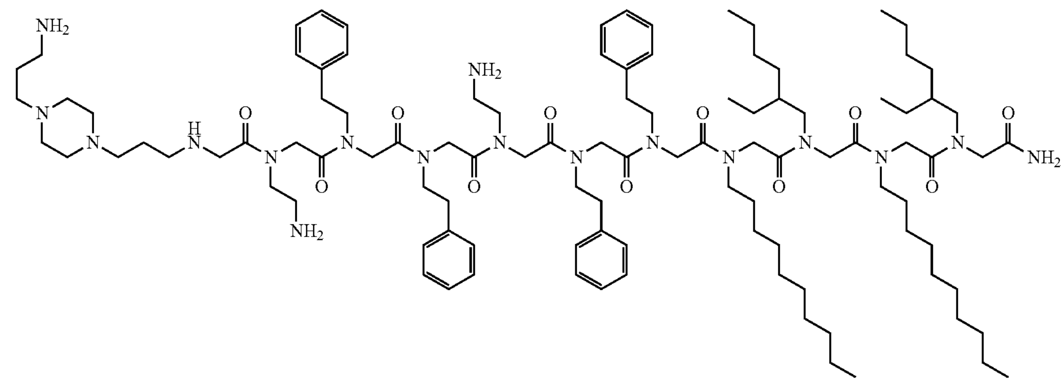 [SMILES: CCCCCCCCCCN(CC(=O)N(CC(=O)N(CCCCCCCCCC)CC(=O)N(CC(N)=O)CC(CC)CCCC)CC(CC)CCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CNCCCN1CCN(CCCN)CC1] |
| 70 | 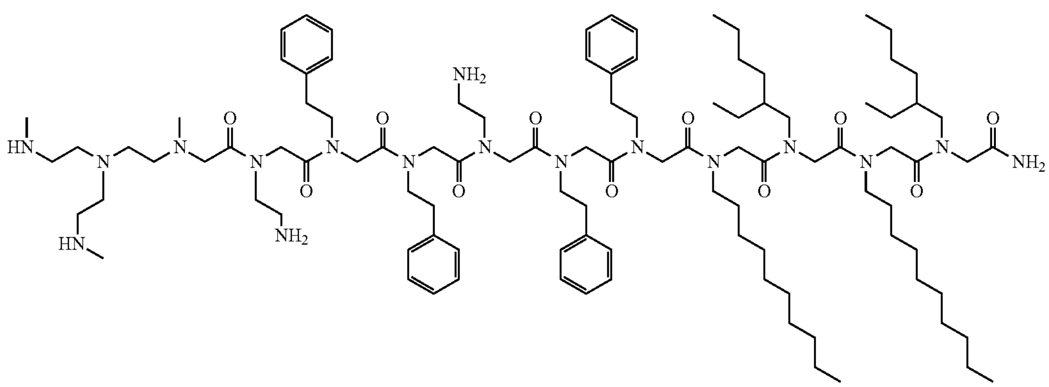 [SMILES: CCCCCCCCCCN(CC(=O)N(CC(=O)N(CCCCCCCCCC)CC(=O)N(CC(N)=O)CC(CC)CCCC)CC(CC)CCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CN(C)CCN(CCNC)CCNC] |
| 71 | 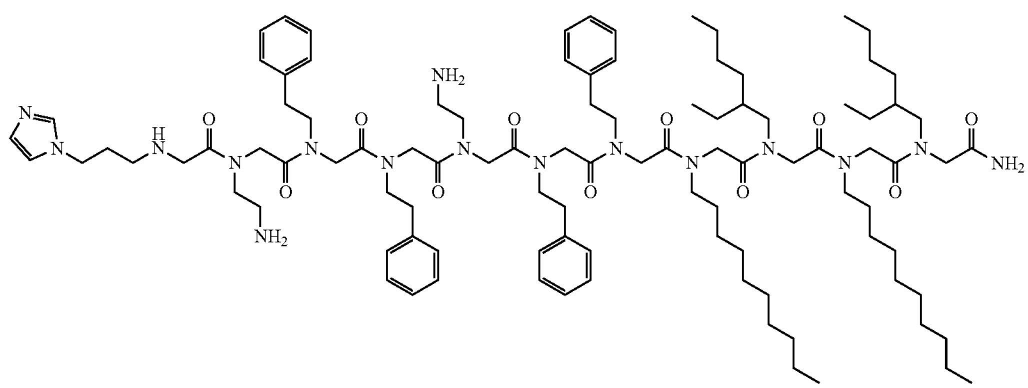 [SMILES: CCCCCCCCCCN(CC(=O)N(CC(=O)N(CCCCCCCCCC)CC(=O)N(CC(N)=O)CC(CC)CCCC)CC(CC)CCCC)C(=O)CN(CCc1ccccc1)C(=O)CN(CCc1ccccc1)C(=O)CN(CCN)C(=O)CN(CCc1ccccc1)C(=O)CN(CCc1ccccc1)C(=O)CN(CCN)C(=O)CNCCCn1ccnc1] |

TABLE 1A-continued

| # | Compound Structure |
|---|---|
| 72 | (structure image) |

TABLE 1B

| Compound # | Predicted Molecular Weight (g/mol) | Retention Time (mm) | m/z (MH) |
|---|---|---|---|
| 1 | 1623.15 | 4.43 | 1623.9 |
| 2 | 1679.26 | 4.76 | 1680.11 |
| 3 | 1735.37 | 5.03 | 1736.2 |
| 4 | 1915.53 | 4.97 | 1916.2 |
| 5 | 1903.69 | 5.88 | 1904.3 |
| 6 | 1481.94 | 4.17 | 1482.9 |
| 7 | 1876.58 | 5.32 | 1877.26 |
| 8 | 2073.91 | 5.62 | 2074.3 |
| 9 | 834.2 | 4.54 | 834.8 |
| 10 | 1256.73 | 4.67 | 1257.7 |
| 11 | 2101.79 | 4.78 | 2103.3 |
| 12 | 2524.32 | 4.81 | 2524.5 |
| 13 | 1195.65 | 4.13 | 1196 |
| 14 | 712.04 | 3.43 | 712.7 |
| 15 | 912.28 | 3.23 | 912.87 |
| 16 | 1312.76 | 3.17 | 1313.2 |
| 17 | 1679.26 | 4.6 | 1680.1 |
| 18 | 1679.26 | 4.62 | 1680.1 |
| 19 | 2271.23 | 5.96 | 2271.57 |
| 20 | 1848.7 | 6.02 | 1849.21 |
| 21 | 2693.76 | 5.88 | 2694.1 |
| 22 | 2468.55 | 6.2 | 2469.62 |
| 23 | 2665.87 | 6.42 | 2666.7 |
| 24 | 2017.8 | 5.41 | 2018.02 |
| 25 | 2115.99 | 5.63 | 2116.41 |
| 26 | 2552.54 | 5.58 | 2553.77 |
| 27 | 1721.34 | 4.76 | 1721.81 |
| 28 | 2115.99 | 5.58 | 2116.4 |
| 29 | 2552.54 | 5.52 | 2552.81 |
| 30 | 1721.34 | 4.7 | 1722.11 |
| 31 | 2236.18 | 5.54 | 2236.66 |
| 32 | 2712.8 | 5.46 | 2713.72 |
| 33 | 1841.54 | 4.64 | 1842.2 |
| 34 | 2194.1 | 5.65 | 2194.43 |
| 35 | 2656.7 | 5.6 | 2656.74 |
| 36 | 1799.46 | 4.79 | 1800.27 |
| 37 | 927.25 | 6.06 | 928.8 |
| 38 | 1349.78 | 5.98 | 1351.8 |
| 39 | 1772.31 | 5.87 | 1774.1 |
| 40 | 1716.2 | 5.66 | 1718.1 |
| 41 | 906.44 | 5.39 | 908 |
| 42 | 920.47 | 5.36 | 921.6 |
| 43 | 921.45 | 5.62 | 922.9 |
| 44 | 977.56 | 5.23 | 978 |
| 45 | 1046.67 | 5.16 | 1047.7 |
| 46 | 1034.66 | 5.23 | 1035.1 |
| 47 | 971.52 | 5.39 | 972.6 |
| 48 | 2859.78 (average) | 5.61 | 1408.8 ($MH_2^{+2}$, distribution, $\delta = 22.06$) |
| 49 | 1328.97 | 5.51 | 1330 |
| 50 | 1343 | 5.43 | 1343.9 |
| 51 | 1343.98 | 5.62 | 1345 |
| 52 | 1400.09 | 5.35 | 1401.1 |
| 53 | 1469.2 | 5.33 | 1470.2 |
| 54 | 1457.19 | 5.38 | 1457.3 |
| 55 | 1394.04 | 5.42 | 1395.1 |
| 56 | 3282.31 (average) | 5.63 | 1664.2 ($MH_2^{+2}$, distribution, $\delta = 22.08$) |
| 57 | 1751.5 | 5.51 | 1752.3 |
| 58 | 1765.53 | 5.48 | 1766.4 |
| 59 | 1766.51 | 5.61 | 1767.3 |
| 60 | 1822.62 | 5.4 | 1824.4 |
| 61 | 1891.73 | 5.38 | 1892.5 |
| 62 | 1879.72 | 5.42 | 1880.5 |
| 63 | 1816.57 | 5.47 | 1817.3 |
| 64 | 3704.84 (average) | 5.59 | 1408.8 ($MH_2^{+2}$, distribution, $\delta = 22.04$) |
| 65 | 1695.39 | 5.21 | 1697.2 |
| 66 | 1709.42 | 5.23 | 1710.3 |
| 67 | 1710.4 | 5.36 | 1711.3 |
| 68 | 1766.51 | 5.14 | 1767.3 |
| 69 | 1835.62 | 5.12 | 1836.4 |
| 70 | 1823.61 | 5.17 | 1823.4 |
| 71 | 1760.47 | 5.22 | 1761.2 |
| 72 | 3648.73 (average) | 5.37 | 1803.0 ($MH_2^{+2}$, distribution, $\delta = 22.06$) |

Example 3

Formulation of Representative Amino Lipidated Peptoids with Oligonucleotides to Form Nanoparticle Compositions The following example describes the general protocol for the formulation of the tertiary amino lipidated and/or PEGylated cationic peptide compounds of formula (I) as described herein with oligonucleotides.

In standard formulations, the tertiary amino lipidated and/or PEGylated cationic peptide compound is dissolved in anhydrous ethanol at a concentration of 0.5 mg/mL (for in vitro experiments) or 5 mg/mL (for in vivo experiments).

The resulting solutions are stable at room temperature, but should be stored at −20° C. The nucleic acid cargo is dissolved in DNAse or RNAse-free water at a final concentration of 0.2 mg/mL (for in vitro experiments) or 1 mg/mL (for in vivo experiments). These solutions should be stored at −20° C. or at −78° C. for longer time periods.

To prepare nanoparticle formulations, the tertiary amino lipidated and/or PEGylated cationic peptide compound is mixed by pipetting with nucleic acid at a mass ratio between approximately 1:1 (peptide compound:cargo) and 20:1. Prior to formulation, tertiary amino lipidated and/or PEGylated cationic peptide compounds and cargo (such as nucleic acid) are diluted in ethanol and acidic buffer (PBS adjusted to pH 5.5 with 0.1 M HCl) respectively to a volume ratio of 1:3 and to target a final cargo concentration of approximately 0.05 mg/mL to 0.2 mg/mL.

Example 4

Characterization of Physical Properties of Representative mRNA/Peptoid Formulations The exemplary amino lipidated cationic peptoids 1-36 described in Example 2 were combined with firefly luciferase (Fluc) mRNA to form nanoparticle compositions to be evaluated for therapeutic and/or prophylactic purposes in vitro or in vivo. The formulations were prepared according to the protocol of Example 3 and mixed by simple pipetting.

The mRNA/peptoid formulation at a 5:1 mass ratio of peptoid:cargo were evaluated by dynamic light scattering (DLS) in order to determine the volume average particle size/diameter (nm) of the mRNA/peptoid complex and the size polydispersity index (PDI) within the formulation. The percentage of mRNA encapsulation for each formulation of the exemplary compounds were determined by fluorescence of the Qubit RNA HS (Invitrogen) dye before and after lysis of particles by Triton X-100. The results are shown in Table 2 below.

TABLE 2

| Compound | Size (nm) | Size PDI | % Encapsulation |
|---|---|---|---|
| 1 | 356.9 | 0.047 | 90.1 |
| 2 | 150 | 0.128 | 100.3 |
| 3 | 255.3 | 0.247 | 95.9 |
| 4 | 326.7 | 0.191 | 99.0 |
| 5 | 364.7 | 0.308 | 88.3 |
| 6 | 448.6 | 0.348 | 92.4 |
| 7 | 296.7 | 0.177 | 88.4 |
| 8 | 234 | 0.077 | 82.5 |
| 9 | 367.9 | 0.122 | 73.9 |
| 10 | 157 | 0.009 | 92.6 |
| 11 | 354.9 | 0.038 | 87.8 |
| 12 | 224.4 | 0.211 | 86.5 |
| 13 | 822.6 | 0.447 | 90.4 |
| 14 | 554 | 0.233 | 77.3 |
| 15 | 1064 | 1 | 76.9 |
| 16 | 1486 | 1 | 85.4 |
| 17 | 472.8 | 0.37 | 90.3 |
| 18 | 593 | 0.762 | 88.5 |
| 19 | 276 | 0.158 | 70.9 |
| 20 | 326.6 | 0.37 | 72.2 |
| 21 | 386.5 | 0.174 | 65.4 |
| 22 | 748.2 | 0.538 | 65.4 |
| 23 | NA | NA | 3.9 |
| 24 | 161 | 0.135 | 87.0 |
| 25 | 773.3 | 0.021 | 8.4 |
| 26 | NA | NA | 35.7 |
| 27 | 438.7 | 0.606 | 50.9 |
| 28 | 308 | 0.085 | 52.0 |
| 29 | 343.4 | 0.237 | 24.8 |
| 30 | 282.8 | 0.455 | 8.4 |
| 31 | 348.5 | 0.404 | 35.7 |
| 32 | 247.5 | 0.274 | 50.9 |
| 33 | 435.7 | 0.048 | 82.0 |
| 34 | 348.4 | 0.295 | 58.0 |
| 35 | 359.8 | 0.486 | 38.0 |
| 36 | 374.4 | 0.127 | 71.5 |

NA = Sample was unsuitable for DLS measurement

Example 5

In Vitro Expression of Firefly Luciferase (Fluc) Following Treatment with Representative Fluc mRNA/Amino Lipidated Cationic Peptoid Formulations The efficacy of mRNA/amino lipidated peptoid formulations was evaluated in vitro based on their ability to deliver the firefly luciferase (Fluc) reporter gene to cultured cells. The amino lipidated cationic peptoids 1-36 of Example 2 were individually combined with Fluc mRNA at a 5:1 w/w ratio, and the resulting particles were added to cultured HeLa cells at a dose of 100 ng/well (in 100 μL total volume). The resulting luciferase expression (RLU) was measured by a luminescence plate reader after 6 hours and 24 hours of treatment. Table 3 below shows the observed luciferase expression for the Fluc mRNA/amino lipidated peptoid formulations at the two time points.

TABLE 3

In vitro expression of firefly luciferase (Fluc) following treatment with representative Fluc mRNA/amino lipidated peptoid formulations

| Compound | Luciferase Expression (RLU) 6 h | 24 h |
|---|---|---|
| 1 | 1.22E+02 | 4.00E+01 |
| 2 | 2.35E+02 | 1.35E+02 |
| 3 | 2.27E+02 | 2.99E+02 |
| 4 | 1.96E+02 | 1.13E+02 |
| 5 | 9.60E+01 | 5.36E+02 |
| 6 | 4.30E+01 | 3.60E+01 |
| 7 | 6.45E+03 | 9.71E+03 |
| 8 | 1.10E+04 | 1.33E+04 |
| 9 | 1.52E+02 | 8.57E+01 |
| 10 | 1.88E+03 | 7.01E+02 |
| 11 | 1.15E+03 | 1.22E+03 |
| 12 | 4.04E+02 | 5.71E+02 |
| 13 | 3.67E+00 | 9.67E+00 |
| 14 | 3.20E+01 | 1.43E+01 |
| 15 | 3.93E+01 | 1.90E+01 |
| 16 | 7.33E+00 | 1.67E+01 |
| 17 | 6.84E+02 | 5.63E+02 |
| 18 | 5.74E+02 | 8.49E+02 |
| 19 | 8.20E+03 | 1.09E+04 |
| 20 | 9.91E+03 | 1.55E+04 |
| 21 | 3.45E+03 | 1.24E+04 |
| 22 | 6.63E+01 | 6.77E+01 |
| 23 | 5.60E+01 | 9.47E+01 |
| 24 | 1.79E+04 | 3.43E+04 |
| 25 | 3.93E+02 | 2.07E+03 |
| 26 | 5.00E+00 | 1.07E+01 |
| 27 | 9.88E+02 | 7.40E+02 |
| 28 | 9.59E+02 | 4.97E+03 |
| 29 | 1.64E+03 | 6.72E+03 |
| 30 | 2.79E+03 | 1.29E+04 |
| 31 | 5.84E+02 | 2.93E+03 |
| 32 | 4.25E+02 | 2.00E+03 |

TABLE 3-continued

In vitro expression of firefly luciferase (Fluc) following treatment with representative Fluc mRNA/amino lipidated peptoid formulations

| Compound | Luciferase Expression (RLU) | |
|---|---|---|
| | 6 h | 24 h |
| 33 | 4.61E+03 | 1.14E+04 |
| 34 | 1.95E+03 | 2.71E+03 |
| 35 | 1.22E+03 | 1.60E+03 |
| 36 | 9.34E+03 | 7.78E+03 |

Figure 4:
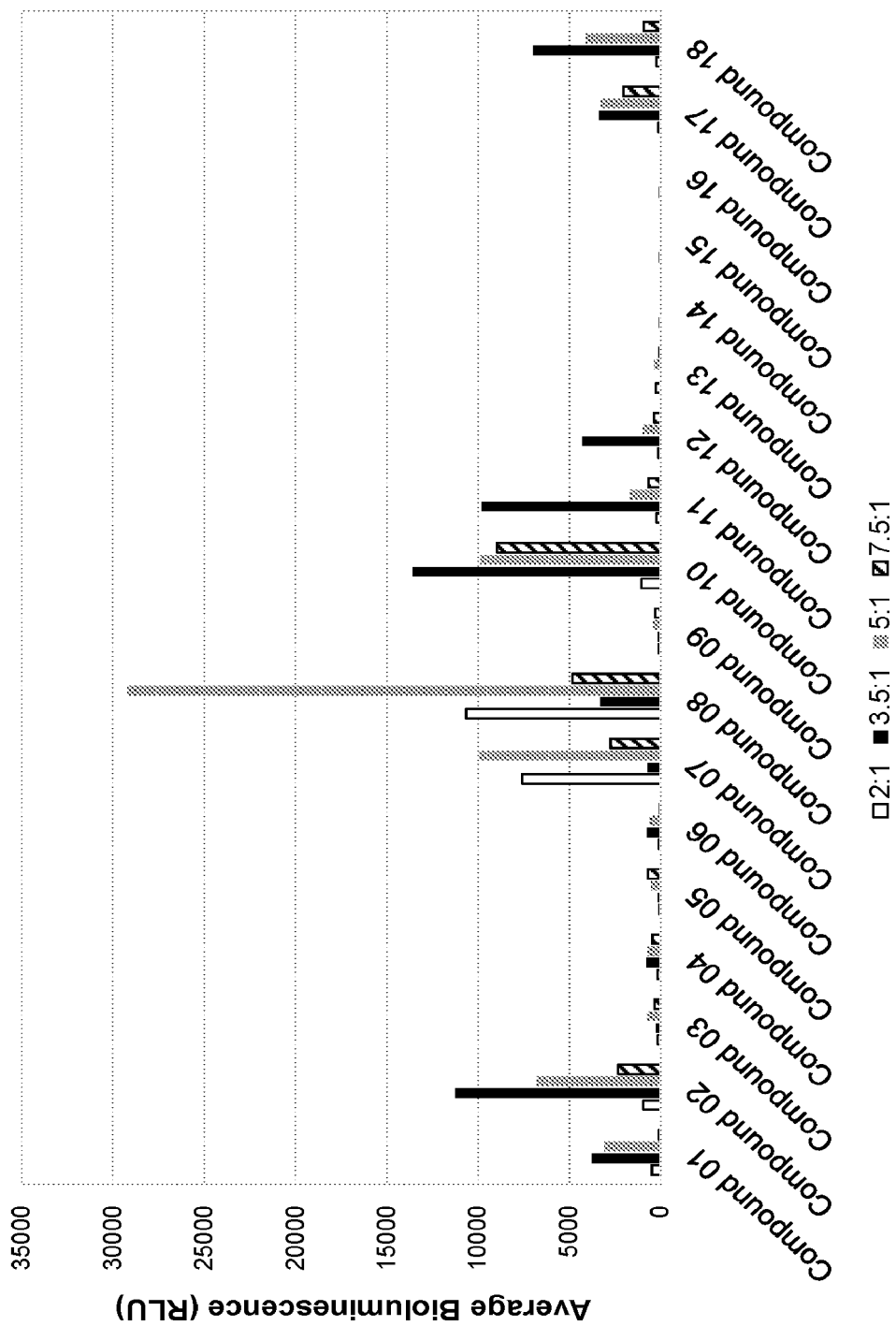
FIG. 4 depicts a graph of the average bioluminescence (RLU) results as measured for HeLa cells in vitro treated with tertiary amino lipidated peptoid compounds 1-18 individually complexed with firefly luciferase (Fluc) mRNA at peptoid:mRNA mass ratios of 2:1, 3.5:1, 5:1 and 7.5:1.

In vitro luciferase expression measurements were also carried out for exemplary amino lipidated cationic peptoid compounds 1-18 from Example 2 at peptoid:mRNA mass ratios of 2:1, 3.5:1, 5:1 and 7.5:1. The observed luciferase expression was measured by a luminescence plate reader as average bioluminescence (RLU) shown in FIG. 4.

Example 6

In Vitro Expression of Firefly Luciferase (Fluc) Following Treatment with Representative Fluc mRNA/Amino Lipidated Peptoid Complexes in Multicomponent Lipid Formulations The efficacy of mRNA/amino lipidated peptoid in multicomponent lipid formulations was evaluated based on their ability to deliver the firefly luciferase (Fluc) reporter gene to cultured HeLa cells in vitro. Three lipid formulations having different mass percentages of lipid components were prepared using cholesterol, 1,2-dioleoyl-sn-glycero-3-phosphoethanolamine (DOPE), and 2-dimyristoyl-rac-glycero-3-methoxypolyethylene glycol-2000 (DMG-PEG2000) relative to the amino lipidated peptoid (peptoid:cholesterol:DOPE:DMG-PEG2000, 50:165:32:2, 63:0:35:2 and 42:23:33:2). Each of the base formulations of the amino lipidated peptoids were then combined with mRNA at mass ratios of 7:1 or 10:1 (peptoid:cargo). The compositions of the six lipid formulations evaluated in this example are illustrated in Table 4 below. Formulations using Lipitoid 1 in place of the amino lipidated cationic peptoid compounds were prepared at the same mass percentages in Table 4 for comparison.

TABLE 4

| Component | Formulation/Mass Percentage | | | | | |
|---|---|---|---|---|---|---|
| | A | B | C | D | E | F |
| Peptoid (or Lipitoid 1) | 50 | 63 | 42 | 50 | 63 | 42 |
| Cholesterol | 16 | 0 | 23 | 16 | 0 | 23 |
| DOPE | 32 | 35 | 33 | 32 | 35 | 33 |
| DMG-PEG2000 | 2 | 2 | 2 | 2 | 2 | 2 |
| Mass ratio of peptoid to mRNA | 7:1 | 7:1 | 7:1 | 10:1 | 10:1 | 10:1 |

Cell Culture: HeLa cells were seeded at 10,000 wells in 100 µL DMEM containing 10% FBS and 1% penicillin/streptomycin, 18 hours prior to treatment and left to adhere. Immediately prior to transfection, media was replaced with 100 µL fresh serum-containing DMEM.

mRNA preparation: Fluc mRNA for transfection experiments was prepared in-house using standard in vitro transcription (IVT) methods.

mRNA Formulation: Lipid mixtures were prepared according to the above stated ratios using master stocks of the amino lipidated peptoids (compounds 2, and 6-18) or Lipitoid 1 (5 mg/mL in ethanol), cholesterol (5 mg/mL), 1,2-dioleoyl-sn-glycero-3-phosphoethanolamine (DOPE, 5 mg/mL), and 2-dimyristoyl-rac-glycero-3-methoxypolyethylene glycol-2000 (DMG-PEG2000, 0.5 mg/mL). To account for remaining volume (and adjust the effective ratio of total lipid to mRNA), 100% ethanol was added. 8 µL of this lipid mixture was then added to 24 µL of mRNA dissolved in acidified PBS (pH 5.5) at a concentration of 15 ng/µL. After mixing, 10 µL of the resulting solution was added to the corresponding well of a 96-well plate. All treatments were performed in triplicate and values expressed as the average. HeLa cells were treated with the resulting solutions for 6 hours, after which time the media was replaced with fresh DMEM. As negative controls, HeLa cells were treated with solutions of mRNA alone. For Lipo conditions, mRNA was formulated with Lipofectamine 2000 (Thermo Fisher) according to the manufacturer's directions.

Figure 5:
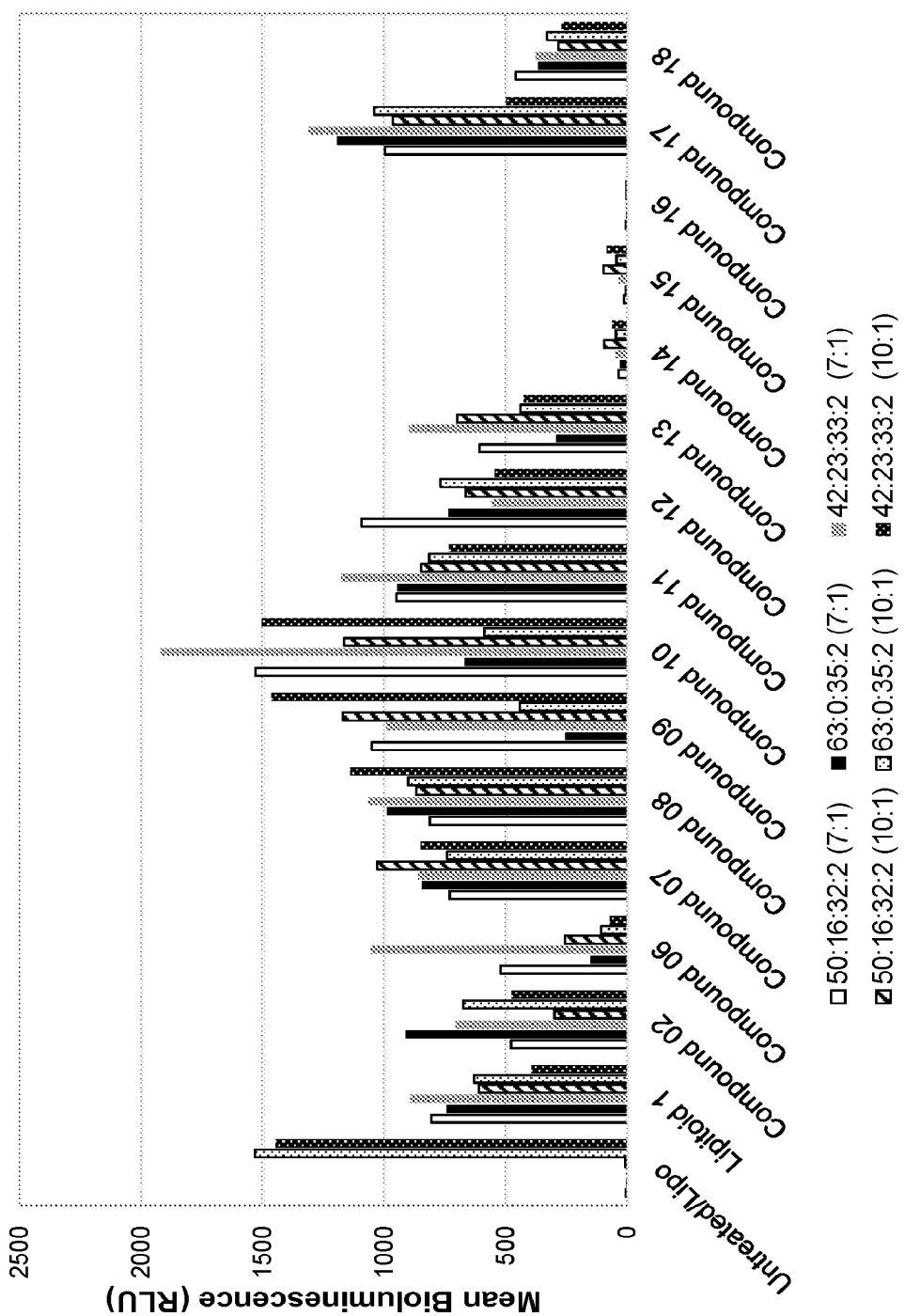
FIG. 5 shows a graph of mean bioluminescence (RLU) observed in HeLa cells in vitro treated with multicomponent lipid formulations containing Lipitoid 1 or one of a selection of amino lipidated peptoid compounds of the present disclosure. Lipitoid 1 or the selected amino lipidated peptoid compound were combined with cholesterol, 1,2-dioleoyl-sn-glycero-3-phosphoethanolamine (DOPE), and 2-dimyristoyl-rac-glycero-3-methoxypolyethylene glycol-2000 (DMG-PEG2000) at three mass ratios (50:16:32:2, 63:0:35:2 and 42:23:33:2) and further mixed with firefly luciferase (Fluc) mRNA at either a peptoid:mRNA mass ratio of 7:1 or 10:1, to provide the test formulations.

In vitro imaging: Prior to imaging, 10 µL of a 30 mg/mL solution of D-Luciferin was added to each well, followed by an incubation for 10 minutes at 37° C. After this time, the luminescence of the entire plate was measured using a SpectraMax iD3 plate reader (Molecular Devices). FIG. 5 depicts a bar chart of the observed mean bioluminescence (RLU) for each of the lipid formulations.

Example 7

In Vitro Expression Of Firefly Luciferase (Fluc) Following Treatment with Representative Fluc mRNA/Amino Lipidated Peptoid Complexes in Multicomponent Lipid Formulation Additional experiments were conducted in order to assess the in vitro delivery efficiency of formulations of amino lipidated peptoids 1-72 with cholesterol, 1,2-dioleoyl-sn-glycero-3-phosphoethanolamine (DOPE), and 2-dimyristoyl-rac-glycero-3-methoxypolyethylene glycol-2000 (DMG-PEG2000) at mass ratio of peptoid:cholesterol:DOPE:DMG-PEG2000 of 41:23:33:3 and a peptoid:Fluc mRNA ratio of 10:1 to HeLa cells.

Figure 6A:
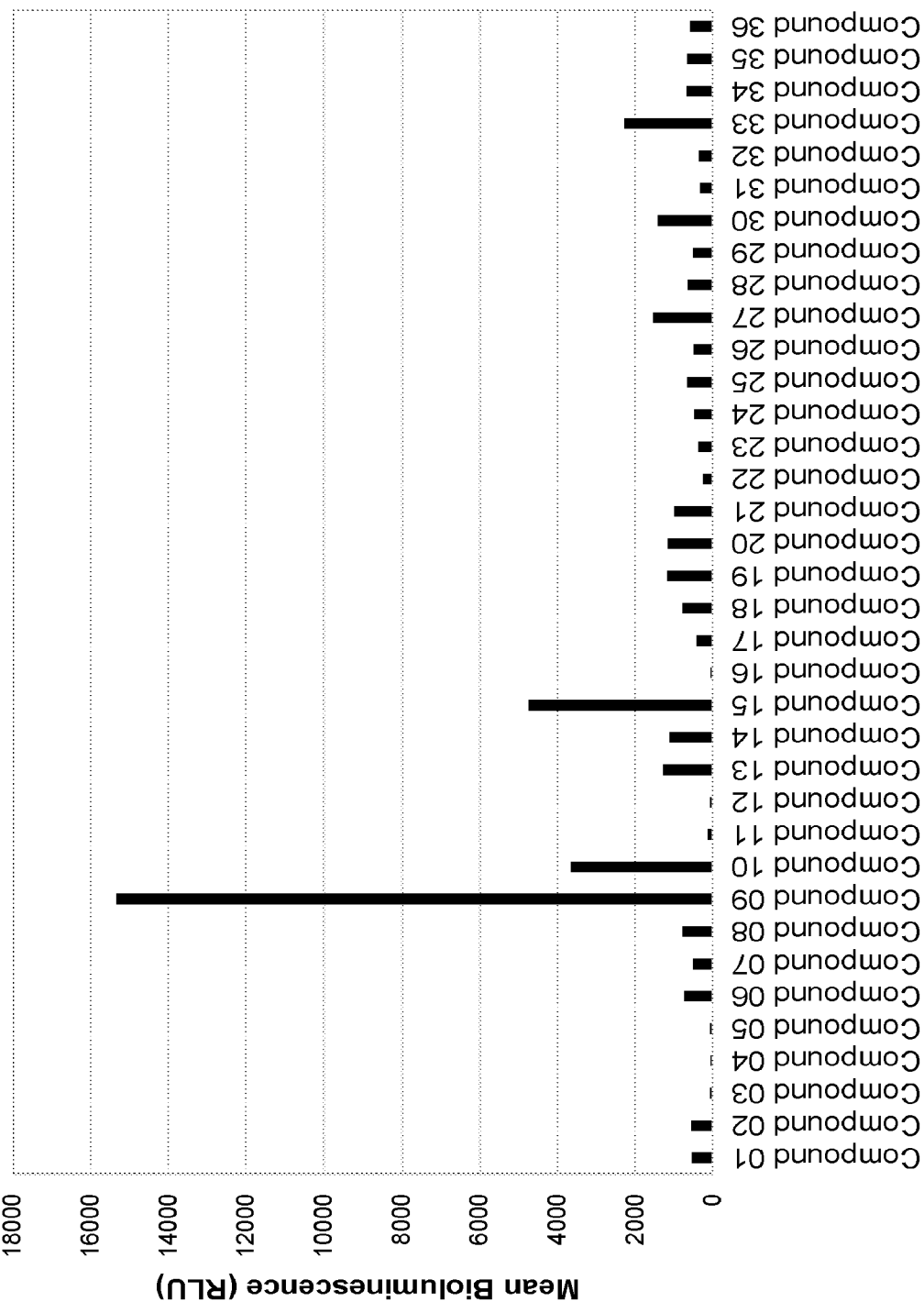
FIGS. 6A-6B show the in vitro expression of Fluc mRNA in HeLa cells treated with multicomponent lipid formulations of amino lipidated peptoids with cholesterol, DOPE and DMG-PEG2000 at a peptoid:cholesterol:DOPE:DMG-PEG2000 mass ratio of 41:23:33:3 and a peptoid:mRNA mass ratio of 10:1.
Figure 6B:
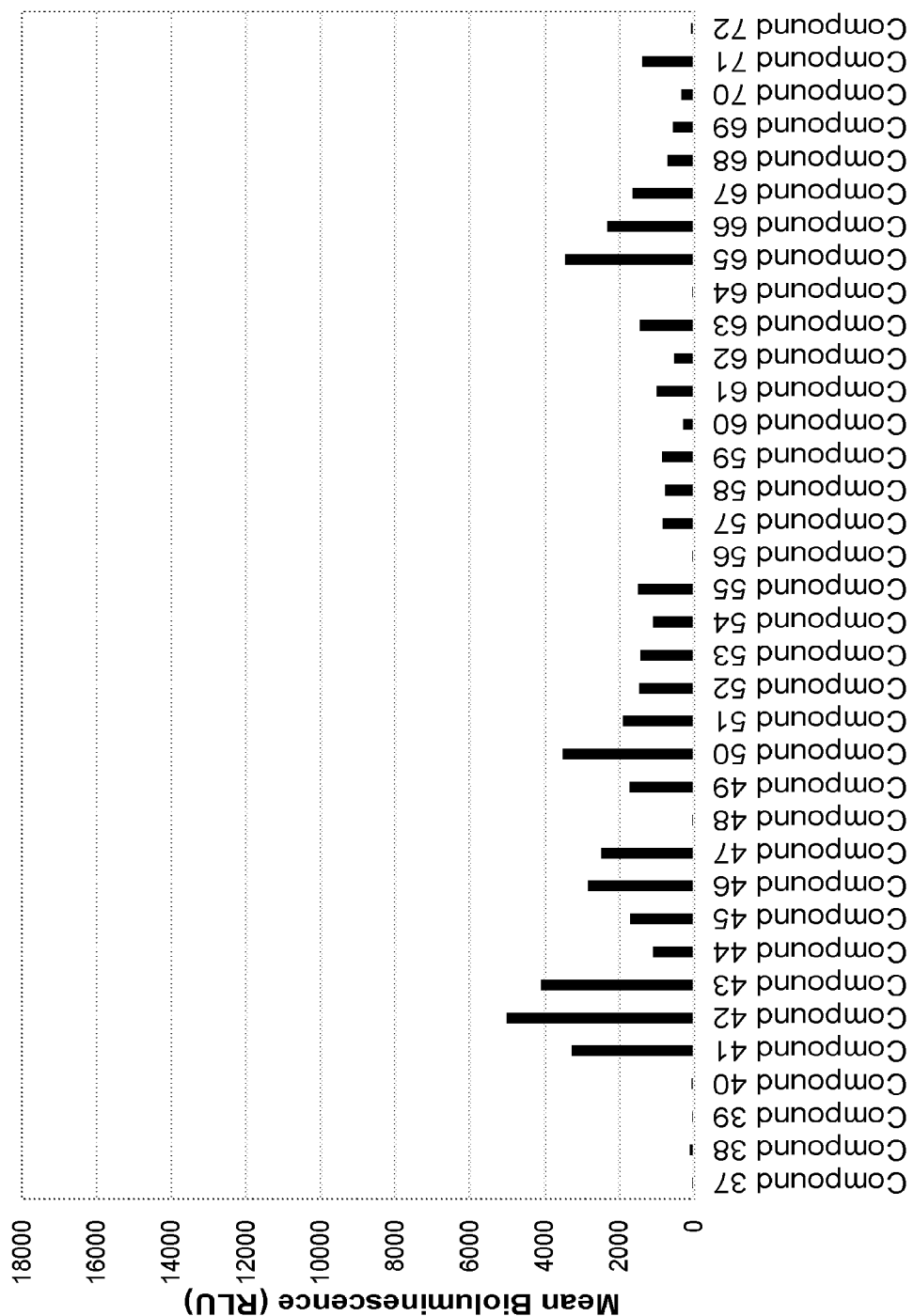

The protocol as described in Example 6 was utilized for the full panel evaluation of multicomponent lipid formulations amino lipidated peptoids 1-72. Briefly, HeLa cells were treated with the formulations for 6 hours (50 ng Fluc mRNA per well), after which time the media was replaced with fresh DMEM. Prior to imaging, 10 µL of a 30 mg/mL solution of D-Luciferin was added to each well, followed by an incubation for 10 minutes at 37° C. After this time, the luminescence of the entire plate was measured using a SpectraMax iD3 plate reader (Molecular Devices). The observed mean luminescence (RLU) for amino lipidated peptoid compounds 1-72 are shown in FIG. 6A (compounds 1-36) and FIG. 6B (compounds 37-72). All treatments were performed in triplicate and values expressed as the average.

Example 8

In Vivo Whole-Body Expression of Firefly Luciferase (Fluc) Following Subcutaneous Administration of Representative Fluc mRNA/Amino Lipidated Multicomponent Lipid Formulations Amino lipidated peptoid compounds were further evaluated for in vivo delivery efficiency of Fluc mRNA to Balb/c mice (n=3) by subcutaneous injection administration. Multicomponent lipid formulations comprising amino lipidated peptoids 1-72 with Fluc mRNA (2 μg, cholesterol, 1,2-dioleoyl-sn-glycero-3-phosphoethanolamine (DOPE), and 2-dimyristoyl-rac-glycero-3-methoxypolyethylene glycol-2000 (DMG-PEG2000) were prepared at a mass ratio of peptoid:cholesterol:DOPE:DMG-PEG2000 of 41:23:33:3 and a peptoid:Fluc mRNA ratio of 10:1. The formulations were administered at a dose of 0.1 mg/kg via a tail-vein injection (approximately 2 μg Fluc mRNA/dose), and the resulting bioluminescence was quantified after 6 hours.

Figure 7A:
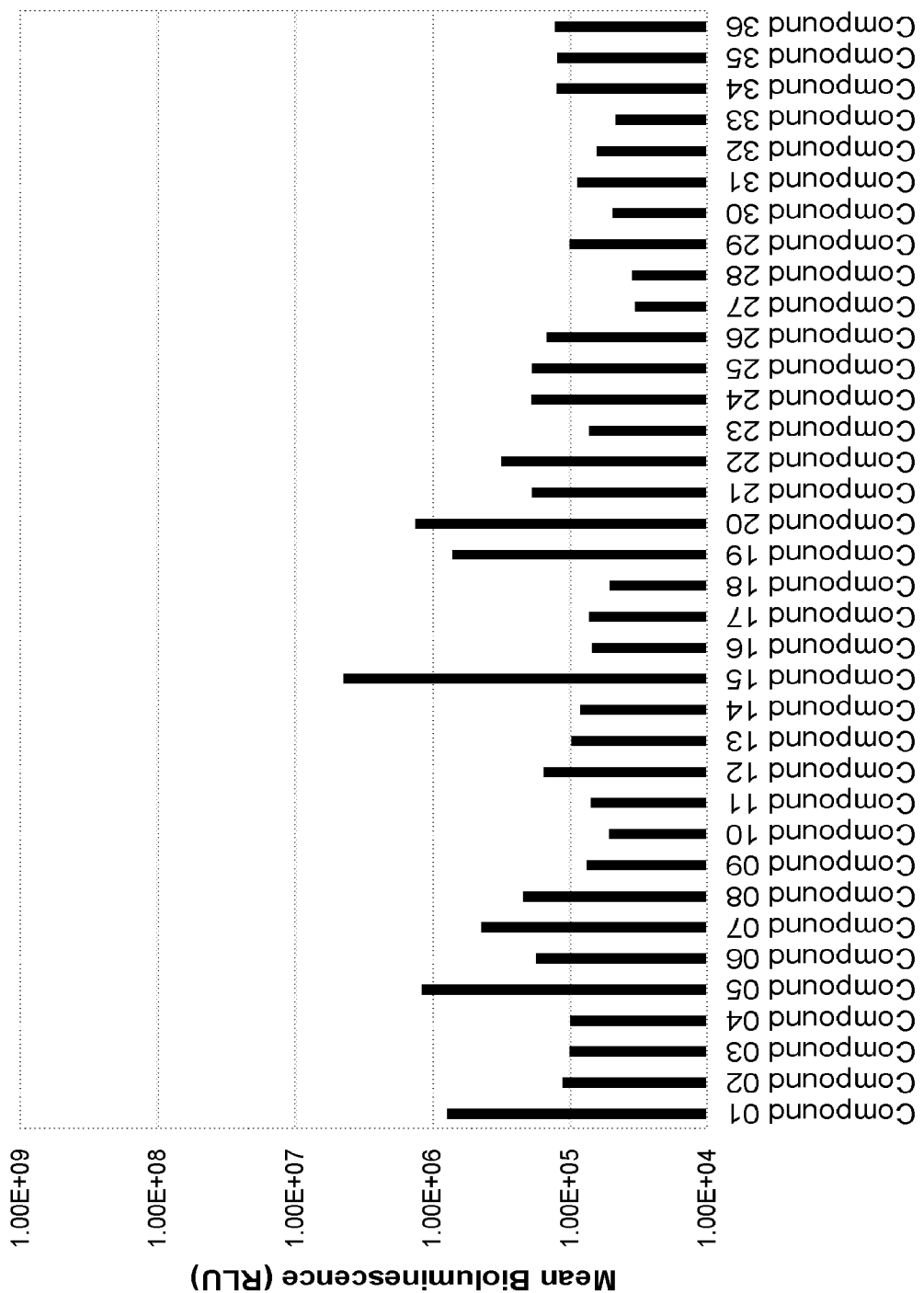
FIGS. 7A-7B show the in vivo expression of Fluc mRNA in Balb/c mice treated with subcutaneous administration of multicomponent lipid formulations of amino lipidated peptoids with cholesterol, DOPE and DMG-PEG2000 at a peptoid:cholesterol:DOPE:DMG-PEG2000 mass ratio of 41:23:33:3 and a peptoid:mRNA mass ratio of 10:1.
Figure 7B:
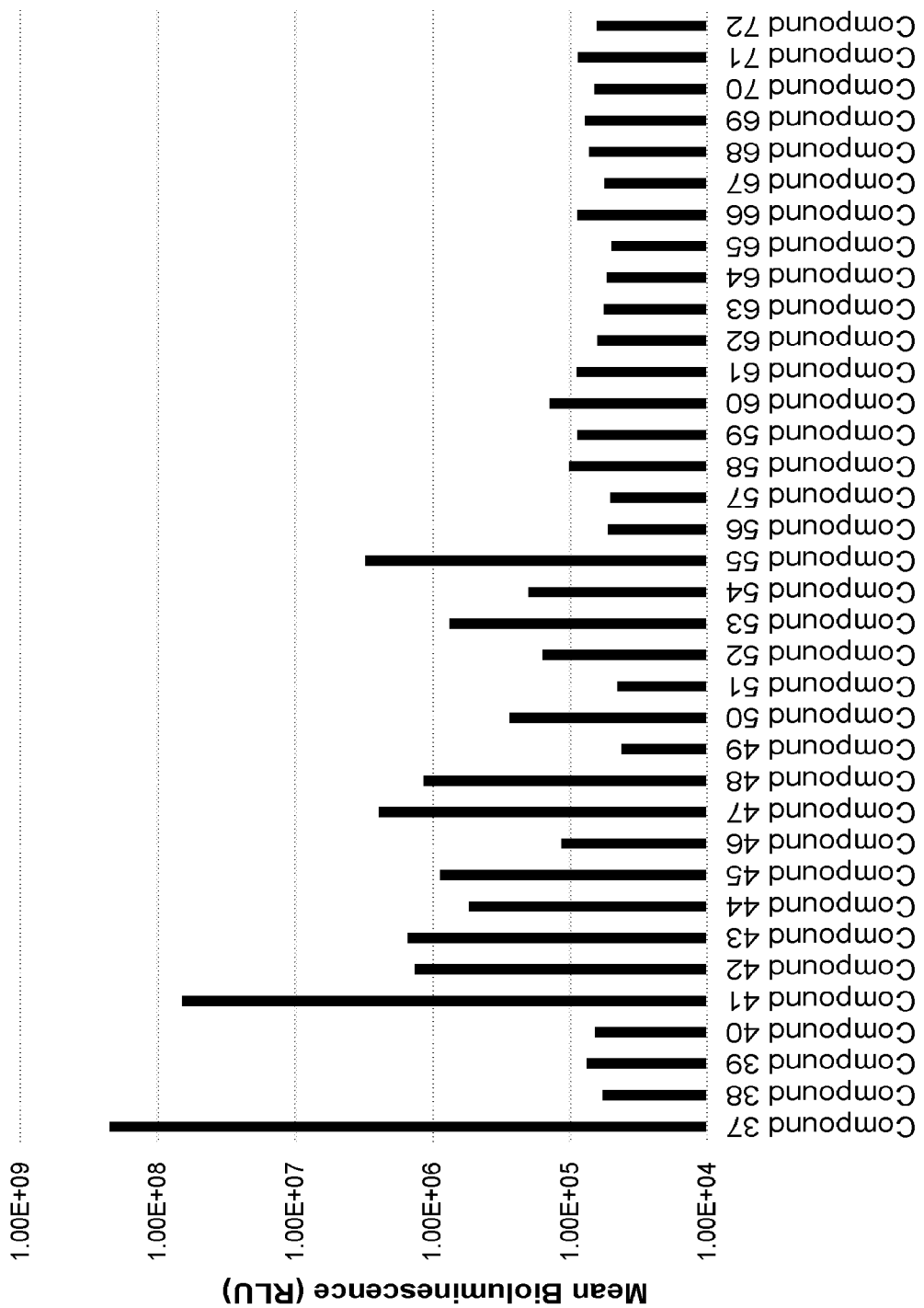

FIGS. 7A and 7B show the in vivo whole body expression of Fluc in the test mice quantified as mean bioluminescence (RLU).

Example 9

In Vitro Expression of Firefly Luciferase (Fluc) Following Administration of Representative Fluc mRNA/Lipitoid 1 Multicomponent Lipid Formulations Further experiments were carried out to evaluate the viability of multicomponent lipid formulations containing lipitoids, specifically Lipitoid 1, in combination with cholesterol, 1,2-dioleoyl-sn-glycero-3-phosphoethanolamine (DOPE), and 2-dimyristoyl-rac-glycero-3-methoxypolyethylene glycol-2000 (DMG-PEG2000) to deliver Fluc mRNA to HeLa cells.

Specifically, varying ratios of the four lipid components were assessed within the following ranges (mass percentage): 20-80% Lipitoid 1; 6-40% cholesterol; 10-53% DOPE; and ratio of total lipid components (Lipitoid 1, cholesterol, DOPE, and DMG-PEG2000) to mRNA between 5:1 and 8:1; the mass percentage of DMG-PEG2000 was held constant at 2% in these experiments. The protocol as described in Examples 6 for the preparation of multicomponent formulations and in vitro bioluminescence assays was utilized.

Ninety-six unique formulations were prepared by pre-mixing the lipid components in ethanol, and complexing the ethanolic lipid solution with an aqueous Fluc mRNA solution. The ratio of ethanol to aqueous solution volume was maintained at 3:1 aqueous:ethanol (vol/vol). The concentrations of each of the lipid components were independently adjusted within the fixed ratio of ethanol to aqueous solution.

HeLa cells were treated with the formulations for 6 hours (50 ng Fluc mRNA per well), after which time the media was replaced with fresh DMEM. Prior to imaging, 10 μL of a 30 mg/mL solution of D-Luciferin was added to each well, followed by an incubation for 10 minutes at 37° C. After this time, the luminescence of the entire plate was measured using a SpectraMax iD3 plate reader (Molecular Devices). All measurements were performed in triplicate and values expressed as the average.

FIG. 8A shows a tablet of the in vitro bioluminescence intensity (RLU) as measured for each of the 96 formulations. The different quadrants of FIG. 8A represent four different cholesterol:DOPE ratios (0.5:1 in the upper left quadrant; 1:1 in the upper right quadrant; 1.5:1 in the lower left quadrant; and 2:1 in the lower right quadrant). Based on the bioluminescence observed for each of the 96 formulations of Lipitoid 1, it was observed that specific formulations exhibited better mRNA delivery efficiency.

Two formulations were selected for further in vitro evaluation based on the results observed in the initial survey of ninety-six formulations above. One formulation was tested in the initial survey (Formulation A, at a mass ratio of lipitoid:cholesterol:DOPE:DMG-PEG2000 of 50:16:32:2 and a ratio of total lipid components to mRNA of 7:1). The second formulation was selected based upon fitting of the experimental data with a second order regression model and obtaining the global maximum (Formulation B, at a mass ratio of lipitoid:cholesterol:DOPE:DMG-PEG2000 of 63:0:35:2 and a ratio of total lipid components to mRNA of 6.12).

In the further in vitro evaluation, Lipitoid Formulations A and B were assessed for their Fluc mRNA delivery efficiency to HeLa cells relative to that of mRNA without a delivery vehicle (mRNA alone), mRNA in a commercially available lipid nanoparticle formulation (Control LNP kit), and Lipitoid 1 with mRNA alone (Lipitoid 1). The same protocols for in vitro transfection and bioluminescence measurements as described above were employed.

Figure 8B:
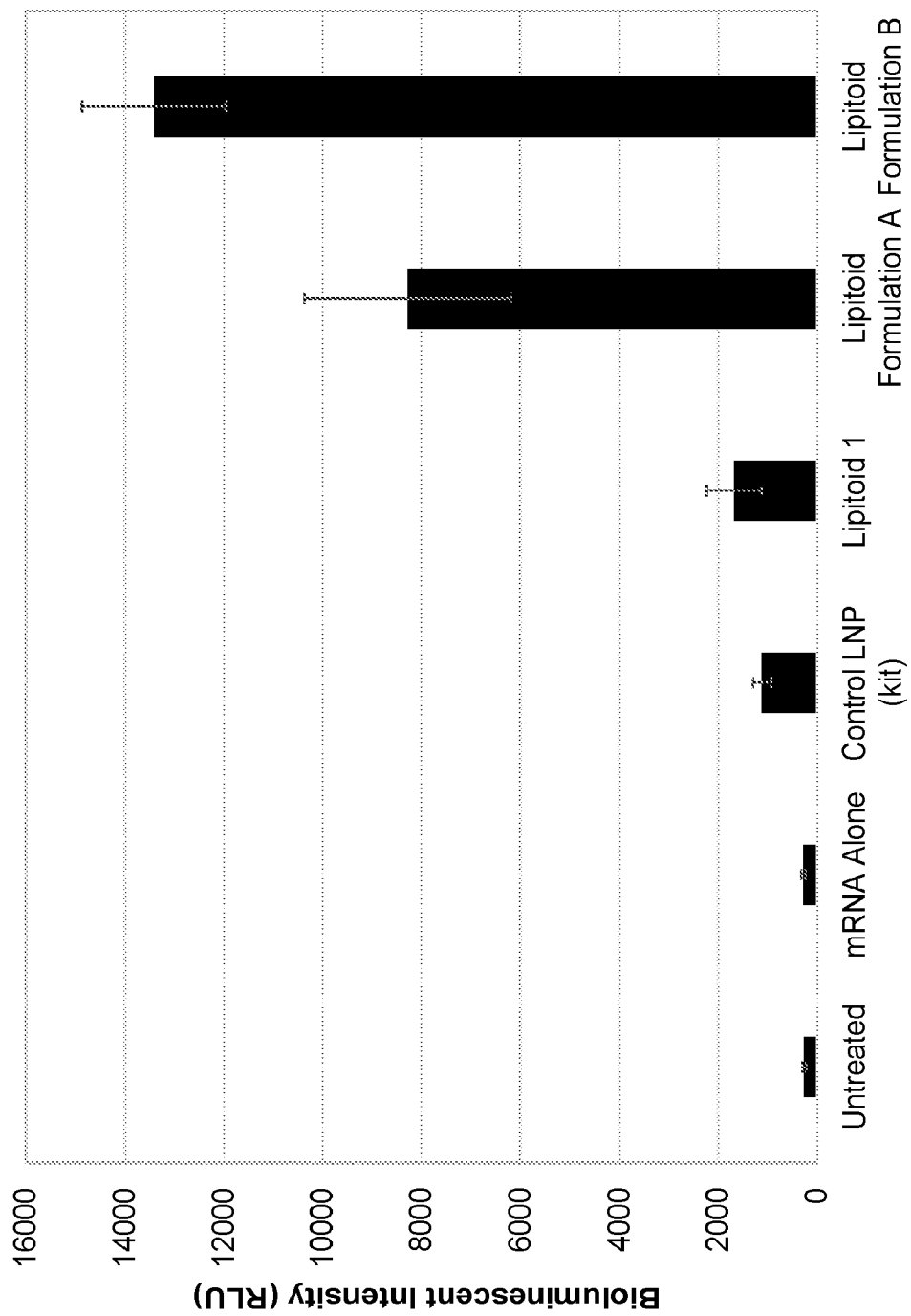

FIG. 8B depicts a bar graph of the bioluminescence intensity (RLU) recorded for each of the treatments above (mRNA alone, Control LNP kit, Lipitoid 1, Lipitoid Formulation A and Lipitoid Formulation B) as well as untreated HeLa cells as a negative control. As shown in FIG. 8B, both Lipitoid Formulation A and Formulation B exhibited greater bioluminescence intensity than Liptioid 1 alone.

What is claimed is:
1. A composition, comprising complexes of:
one or more polyanionic compounds; and
lipid components, wherein the lipid components comprise:
(i) optionally one or more structural lipids;
(ii) one or more phospholipids;
(iii) one or more shielding lipids; and
(iv) one or more tertiary amino lipidated and/or PEGylated cationic peptide compounds of formula (I) or salts thereof:

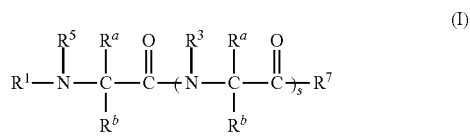

(I)

wherein:
s is an integer from 1 to 5;
$R^1$ is —H;
each $R^3$ is independently selected from $C_8$-$C_{24}$alkyl;
$R^5$ is selected from aminoalkyl, aminoalkylaminoakyl, and hydroxyalkyl;
$R^7$ is —$NH_2$; and
each $R^a$ and $R^b$ are independently.

2. The composition of claim 1, comprising 40-80% w/w compounds of formula (I) of the total weight of the lipid components.

3. The composition of claim 1, wherein s is 3 or 4.

4. The composition of claim 1, wherein each $R^3$ is independently selected from the group consisting of

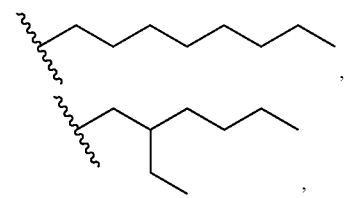

,

-continued

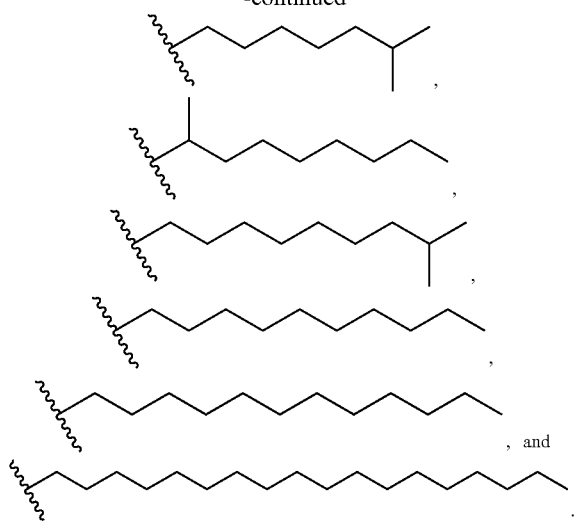
, and

5. The composition of claim 1, wherein $R^5$ is aminoalkyl or aminoalkylaminoakyl.

6. The composition of claim 5, wherein $R^5$ is

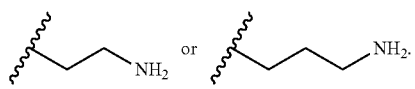

7. The composition of claim 1, comprising 0-40% w/w one or more structural lipids of the total weight of the lipid components.

8. The composition of claim 1, wherein the one or more structural lipids are selected from the group consisting of cholesterol, fecosterol, sitosterol, ergosterol, campesterol, stigmasterol, brassicasterol, tomatidine, ursolic acid, alpha-tocopherol, and mixtures thereof.

9. The composition of claim 1, comprising 10-60% w/w one or more phospholipids of the total weight of the lipid components.

10. The composition of claim 1, wherein the one or more phospholipids are selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-0-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C 16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and any mixtures thereof.

11. The composition of claim 1, comprising 1-5% w/w one or more shielding lipids of the total weight of the lipid components.

12. The composition of claim 1, wherein the one or more shielding lipids are one or more PEG lipids selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

13. The composition of claim 1, wherein the lipid components comprise by total weight of the lipid components:
(i) 40-70% w/w one or more tertiary amino lipidated cationic peptide compounds;
(ii) 0-25% w/w cholesterol;
(iii) 20-40% w/w 1,2-dioleoyl-sn-glycero-3-phosphoethanolamine (DOPE); and
(iv) 1-5% w/w 1,2-dimyristoyl-rac-glycero-3-methoxypolyethylene glycol-2000 (DMG-PEG2000).

14. The composition of claim 1, wherein the one or more polyanionic compounds comprise a nucleic acid.

15. The composition of claim 1, wherein the one or more polyanionic compounds comprise a nucleic acid and wherein the nucleic acid is an mRNA encoding a polypeptide.

16. The composition of claim 1, wherein the mass ratio of the lipid components to the one or more polyanionic compounds is between 2:1 and 25:1.

17. The composition of claim 1, wherein s is 4 and:
(a) two $R^3$ are

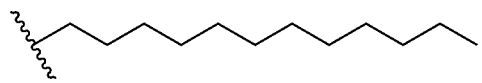

and two $R^3$ are

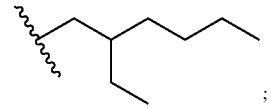 [SMILES: *CC(CC)CCCC]

or
(b) each $R^3$ is

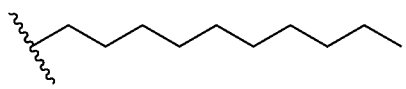

18. The composition of claim 1, wherein $R^5$ is a hydroxyalkyl.

19. The composition of claim 18, wherein $R^5$ is

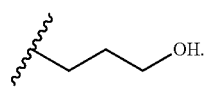 [SMILES: *CCCO]

20. The composition of claim 1, wherein s is 4; each $R^3$ independently is

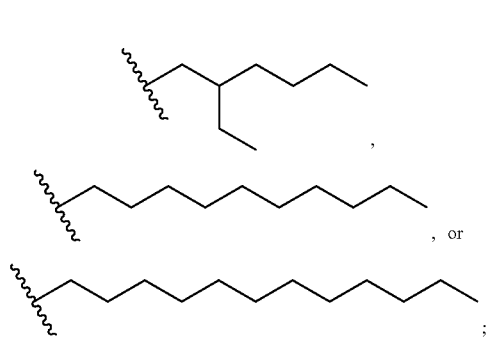

, or $R^5$ is

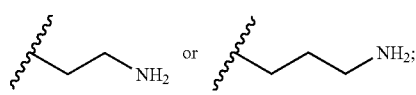

$R^7$ is $NH_2$; and each $R^a$ and $R^b$ independently is H.

21. The composition of claim 20, wherein two $R^3$ are

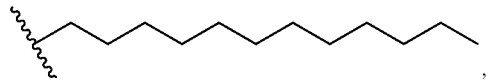 [SMILES: *CCCCCCCCCCCC]

and two $R^3$ are

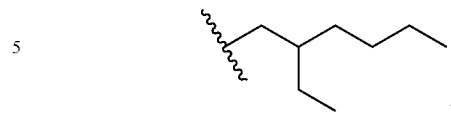

22. The composition of claim 1, wherein s is 4; each $R^3$ independently is

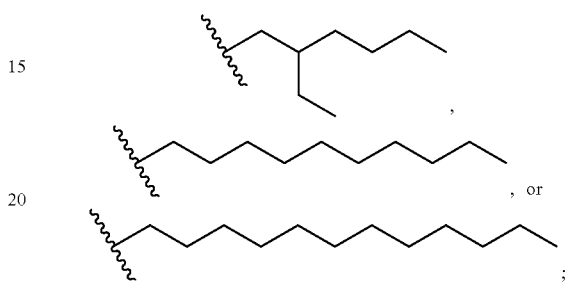

, or $R^5$ is hydroxyalkyl; $R^7$ is $NH_2$; and each $R^a$ and $R^b$ independently is H.

23. The composition of claim 22, wherein each $R^3$ independently is

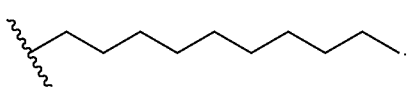 [SMILES: *CCCCCCCCCC]

24. The composition of claim 1, wherein the compound of formula (I) is

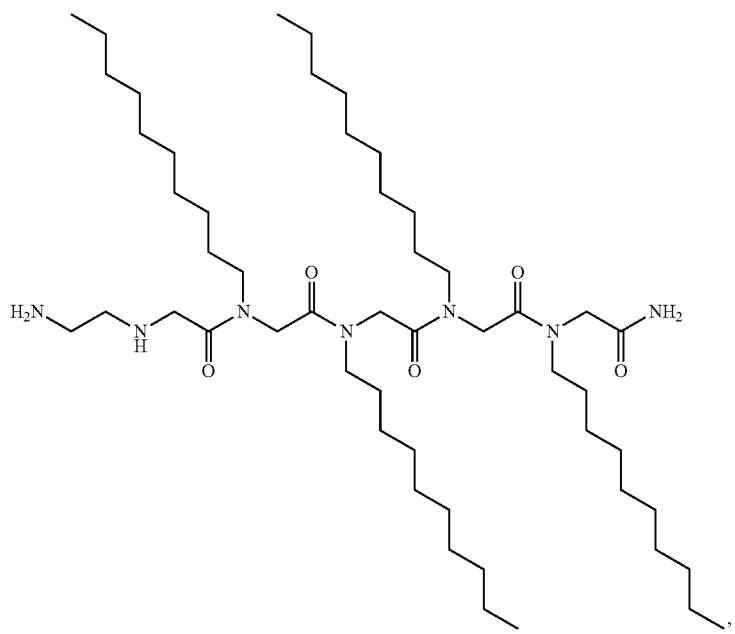

-continued
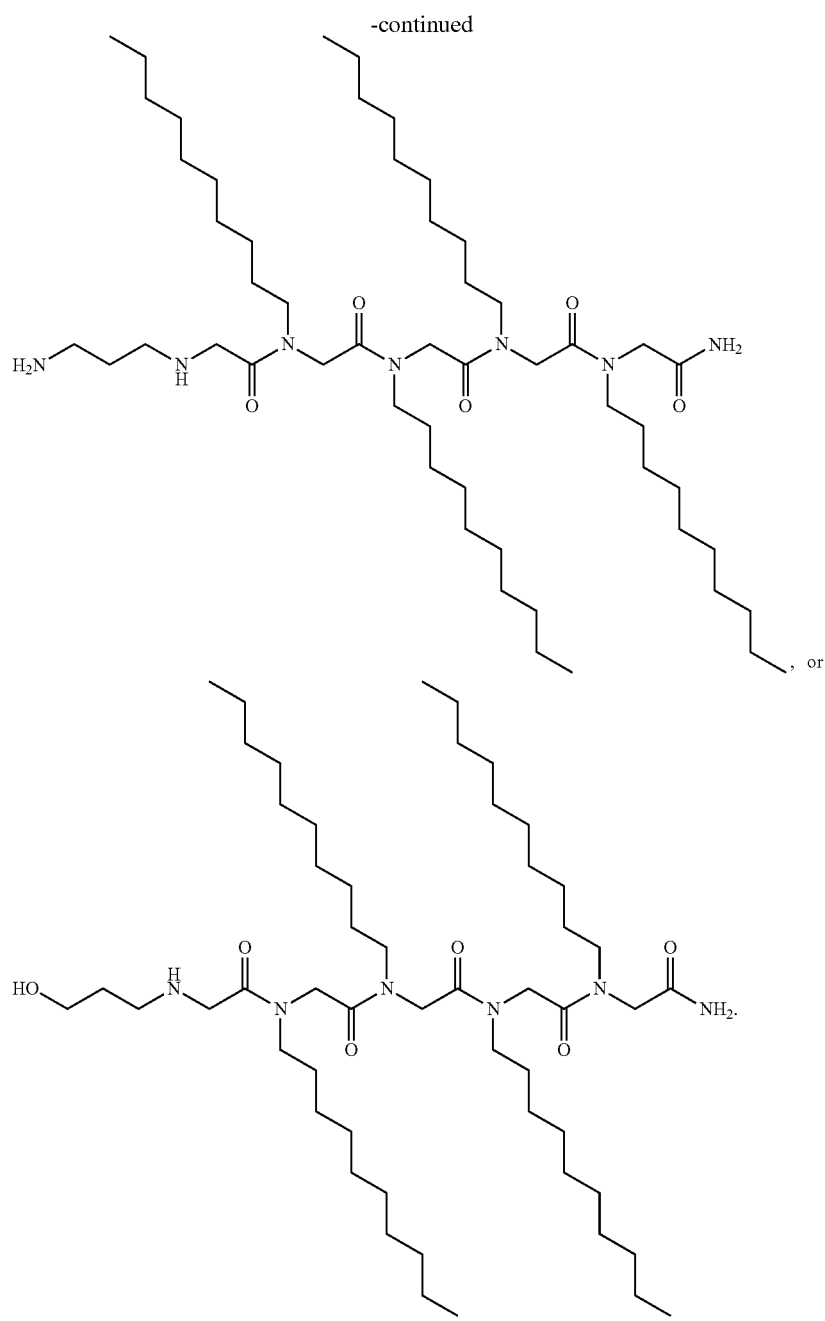
, or
25. A method of delivering a polyanionic compound to a cell comprising contacting the cell with the composition of claim 1.
26. The method of claim 25, wherein the polyanionic compound comprises a nucleic acid which is a mRNA encoding a polypeptide and the cell expresses the polypeptide after being contacted with the complex.
* * * * *